(12) United States Patent
Takahashi

(10) Patent No.: US 6,868,735 B2
(45) Date of Patent: Mar. 22, 2005

(54) METHOD FOR NONDESTRUCTIVELY EVALUATING AGED DETERIORATION OF FERROMAGNETIC CONSTRUCTION MATERIALS

(75) Inventor: Seiki Takahashi, Morioka (JP)

(73) Assignee: Iwate University, Iwate Pref. (JP)

( * ) Notice: Subject to any disclaimer, the term of this patent is extended or adjusted under 35 U.S.C. 154(b) by 0 days.

(21) Appl. No.: 10/680,279

(22) Filed: Oct. 7, 2003

(65) Prior Publication Data

US 2004/0112140 A1 Jun. 17, 2004

(30) Foreign Application Priority Data

Oct. 9, 2002 (JP) .......................... 2002-296381
Apr. 15, 2003 (JP) .......................... 2003-110407

(51) Int. Cl.$^7$ .......................... G01D 7/02; G01R 33/00
(52) U.S. Cl. .......................... 73/789; 324/224
(58) Field of Search .......................... 73/862.333, 862.336, 73/789; 702/38; 324/209, 227, 223, 224; 493/730

(56) References Cited

U.S. PATENT DOCUMENTS

| | | | | |
|---|---|---|---|---|
| 4,931,730 A | * | 6/1990 | Olsen et al. ............ | 324/209 |
| 5,008,621 A | * | 4/1991 | Jiles ...................... | 324/227 |
| 5,059,903 A | * | 10/1991 | Otaka et al. ........... | 324/223 |
| 5,134,368 A | * | 7/1992 | Otaka et al. ........... | 324/224 |
| 5,142,227 A | * | 8/1992 | Fish ...................... | 324/209 |
| 5,313,405 A | * | 5/1994 | Jiles et al. ............. | 702/38 |
| 6,448,764 B2 | * | 9/2002 | Noe et al. .............. | 324/209 |
| 6,631,647 B2 | * | 10/2003 | Seale ..................... | 73/789 |

* cited by examiner

Primary Examiner—Edward Lefkowitz
Assistant Examiner—Octavia Davis
(74) Attorney, Agent, or Firm—Knobbe Martens Olson & Bear, LLP

(57) ABSTRACT

Aged deterioration of ferromagnetic construction materials is nondestructively evaluated by applying to an evaluating material a magnetic field whose magnetic field amplitude is rather low, distinguishing various lattice defects, and quantifying them separately. A method includes obtaining a stress-strain relation in advance by a tensile test, evaluating a minor hysteresis loop (reference minor loop) while applying an applied stress ($\sigma$) thereto, obtaining correlation between physical quantities for evaluating aged deterioration, obtaining a subject minor hysteresis loop (subject minor loop) by a tensile test, obtaining measured values of the physical quantities from the loop, and evaluating aged deterioration of the evaluating material from the measured values.

20 Claims, 42 Drawing Sheets

METHOD FOR NONDESTRUCTIVELY EVALUATING AGED DETERIORATION OF FERROMAGNETIC CONSTRUCTION MATERIALS

BACKGROUND OF THE INVENTION

1. Field of the Invention

The present invention relates to a method for nondestructively measuring and quantitatively evaluating deterioration of material strength due to aging, in ferromagnetic construction materials, or in structures comprised of such materials.

2. Description of the Related Art

Conventional nondestructive inspection methods for aged material deterioration had generally aimed at investigating of initiation and growth of cracks in the material in almost every case. And thus, the direction of development in present nondestructive inspection methods lies in finding out produced cracks as minute as possible. Accordingly, with such a conventional nondestructive inspection method, it is practically impossible to inspect nondestructively aged deterioration of materials before the initiation of cracks.

By the way, another type of previous method is known for nondestructively measuring material strength deteriorated with age in ferromagnetic construction materials or structures comprised in such construction materials. In this measuring method, the coercive force and magnetic susceptibility in the range approaching to saturation magnetization of a measuring object are measured.

However, in the above-mentioned conventional method, a magnetic field that is far larger than the coercive force of materials has to be applied for the magnetizing until the magnetization is saturated. Consequently, it is necessary for using a large magnetizing yoke and allowing a large magnetizing current to flow through the magnetizing coil. Therefore a measuring machine incorporating such a large magnetic yoke and a large capacity magnetizing power source for energizing the magnetic yoke is not only expensive, but also makes the entire system heavy and large in size to require a noticeable installation space.

Consequently, in order to solve these problems, the Inventor proposed a method for evaluating aged deterioration in evaluating ferromagnetic construction materials, or in structures comprised of such ferromagnetic construction materials, which is based on relationships between the stress $\sigma$ and the susceptibility coefficient c ($=\chi_c H^3$) obtained from the magnetic susceptibility $\chi_c$ and the magnetic field intensity H of an evaluating material (see, for example, Japanese Examined Patent Publication No. 158182), and another method for the same purpose which is based on relationships between the ratio of the coercive force of an evaluating material against its magnetic susceptibility, and the coercive force (see, for example, Japanese Examined Patent Publication No. 3300810).

However, it has been impossible to obtain detailed information regarding the aged deterioration of ferromagnetic construction materials by using such methods as mentioned above which are dependent on the measurement of the coercive force and magnetic susceptibility of the material. The reason is as follows. Both the coercive force and the ratio of the coercive force against the magnetic susceptibility obtained from hysteresis loops, give the information which appears according to the maximum force which the magnetic domain walls receive from a lattice defect in the movements of the magnetic domain walls, in the state in which the maximum of the magnetic field intensity applied to that material reaches saturation magnetic field intensity, and the domain walls inside that material becomes the most ready to move out.

The susceptibility coefficient c also is the information in a limited range of magnetization of the evaluating ferromagnetic material. Accordingly, these parameters provide limited information about the aged deterioration of an evaluating ferromagnetic material. Therefore, according to the above-mentioned conventional methods, although information regarding the aged deterioration of a material by using the coercive force is obtained from a maximum potential energy for domain wall movements in the material, it is impossible to account for an overall image of the potential energy. Any one of the above-mentioned methods can hardly specify, with regard to the aged deterioration of the evaluating ferromagnetic material, individual defects in terms of the internal structure of the evaluating material responsible for the deterioration.

Moreover, in the case of evaluating the aged deterioration of an evaluating ferromagnetic material using the ratio of its coercive force against its magnetic susceptibility, it is necessary to apply, to the evaluating material, the comparatively high magnetic field intensity more than its coercive force of the evaluating material. Further, to exactly determine the aged deterioration of an evaluating ferromagnetic material by the method dependent on the susceptibility coefficient c, in order to evaluate the aged deterioration of ferromagnetic materials more correctly, obtaining an ideally shaped hysteresis loop of the material is desirable. For this reason, it is difficult to make the maximum level of the magnetic field intensity still lower. Thus, with both methods, if the externally applied magnetic field is lower than specified above, it is hardly possible to obtain precise and detailed information about the aged deterioration of an evaluating ferromagnetic material.

SUMMARY OF THE INVENTION

In view of above, the object of the present invention is to provide a method for precisely and comprehensively evaluating the aged deterioration of ferromagnetic construction materials or of structures comprised of such materials, by more finely evaluating the type and quantity of lattice defects under a magnetic field with a less intensity than it has been observed with conventional methods.

The invention provides a method for nondestructively and quantitatively evaluating aged deterioration of evaluating ferromagnetic construction materials comprising an evaluation information acquiring step of obtaining a stress-strain relation in advance by a tensile test with respect to a test piece which is made of the same evaluating ferromagnetic construction material (evaluating material), evaluating a minor hysteresis loop (reference minor loop) of the test piece while applying an applied stress $\sigma$ thereto, the stress $\sigma$ being appropriately determined according to the stress-strain relation, and obtaining correlation between physical quantities for evaluating aged deterioration of the evaluating material; a measurement step of obtaining a subject minor hysteresis loop (subject minor loop) by a tensile test with respect to the evaluating material and obtaining measured values of said physical quantities from the loop; an evaluation step of evaluating aged deterioration of the evaluating material from said measured values of said physical quantities obtained in the measurement step, according to said correlation between said physical quantities obtained in the foregoing evaluation information acquiring step, wherein the minor hysteresis loops are obtained from the evaluating material, by applying a magnetic field to the material and increasing the intensity H of the magnetic field to a maximum $H_a$ which is lower than the saturation intensity while following the change of magnetic flux density B of the material and repeating the same process changing the $H_a$ in a stepwise manner, and provide changes of magnetic flux density B as a function of magnetic field intensity H with the magnetic field amplitude $H_a$ of magnetic field being varied.

According to the method for nondestructively evaluating aged deterioration of ferromagnetic construction materials of the above present invention, as mentioned later, all of physical quantities obtained from a minor hysteresis loop are sensitive to the quantity of lattice defects, such as dislocations, and the physical quantities obtained from a minor hysteresis loop excel the physical quantities such as the coercive force obtained from the conventional major hysteresis loops in terms of sensitivity or accuracy.

For example, a correlation between physical quantities obtained from minor hysteresis loop, e.g., the correlation between the pseudo coercive force Hc* and the reciprocal of pseudo susceptibility $1/\chi_H^*$ which varies according to changing the value of magnetic field amplitude $H_a$ gives an overall view of the potential energy of domain wall movements. Therefore, it is possible by resorting to such correlation to obtain more detailed information regarding the aged deterioration of ferromagnetic construction materials and distinguish various lattice defects involved in fatigue of a material.

Moreover, a minor hysteresis loop is obtained from an evaluating material by applying, to the material, a magnetic field whose maximum value of magnetic field amplitude $H_a$ is lower than the saturation intensity while following the magnetic flux density B of the material, and by plotting the magnetic flux measurements as a function of magnetic field intensity H. This process is repeated with the magnetic field amplitude varied in a stepwise manner so that a series of minor hysteresis loops are obtained in the material.

Thus, according to the evaluating method of the present invention, it is possible to more minutely distinguish various lattice defects responsible for aged deterioration of ferromagnetic construction materials or structures comprised of such materials than it is possible with conventional methods, and to more precisely quantify the involvement of individual factors using minor hysteresis loops obtained in the material under a magnetic field whose maximum value of magnetic field amplitude is kept lower, and thus to evaluate aged deterioration of the material more minutely, precisely and comprehensively.

The method for nondestructively evaluating aged deterioration of ferromagnetic construction materials of the present invention is characterized by that said correlation between physical quantities includes the first relation of the relation between the pseudo coercive force Hc* and magnetic field amplitude $H_a$ applied to the measured object, the pseudo coercive force Hc* being the magnetic field intensity H at the point where the magnetic flux density B is zero, and the second relation of the relation between the reciprocal $1/\chi_H^*$ of the pseudo susceptibility $\chi_H^*$ being the gradient of a reference minor hysteresis loop at the point where the magnetic field intensity H is equal to the pseudo coercive force Hc* and magnetic field amplitude $H_a$; and the physical quantities obtained via said measurement step comprise the pseudo coercive force Hc* being the magnetic field intensity H at the point where the magnetic flux density B is zero, and the reciprocal $1/\chi_H^*$ of the pseudo susceptibility $\chi_H^*$ being the gradient of said subject minor hysteresis loop at the point where the magnetic field intensity H is equal to the pseudo coercive force Hc*.

DETAILED DESCRIPTION OF THE INVENTION

Figure 1A:
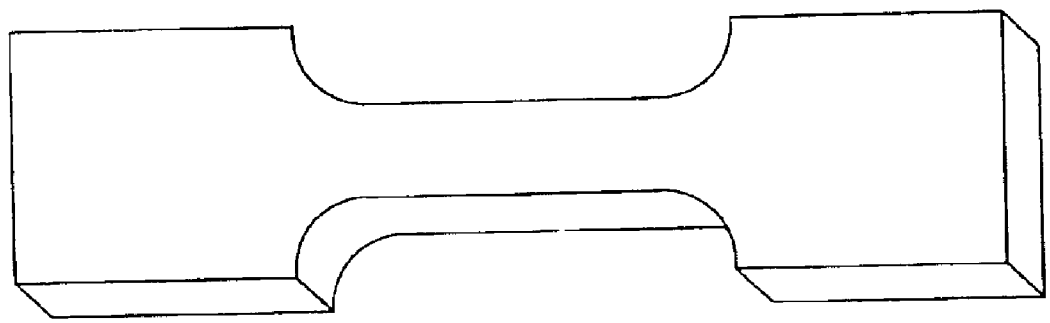
FIGS. 1a and 1b are perspective views showing the shape of samples to be submitted to the tensile test and the minor hysteresis loop measurement.
Figure 1B:
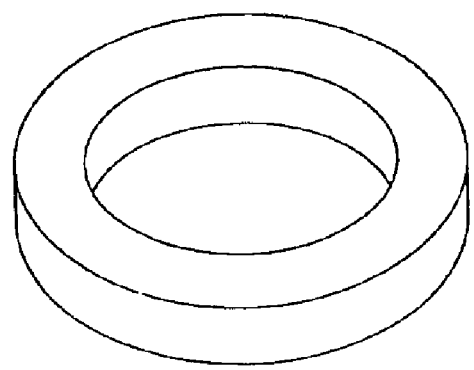

How to execute the evaluating method of the present invention and what advantages can be obtained from the method will be described with reference to data obtained from tests actually carried out. To elucidate the interrelationship between the mechanical and magnetic properties of steel materials, evaluating materials were prepared which consist of polycrystalline pure iron and a low-alloy steel A533B having an average grain size of 37 μm. The low-alloy steel A533B is a material used for constructing the pressure vessel of nuclear reactor furnaces. These evaluating materials were formed into samples having shapes as shown in FIGS. 1a and 1b, respectively, which are to be subjected to tensile test and hysteresis loop measurement. The material formed into a sample as shown in FIG. 1a was used for the tensile test, while the material formed into a sample as shown in FIG. 1b was used for the hysteresis loop measurement. Table 1 below shows the composition of the low-alloy steel A533B submitted to the test.

TABLE 1

| A533B | C | Si | Mn | P | S | Cu | Ni | Mo | Al |
|---|---|---|---|---|---|---|---|---|---|
| Wt. % | 0.18 | 0.15 | 1.5 | 0.004 | 0.001 | 0.03 | 0.66 | 0.56 | 0.01 |

Figure 2:
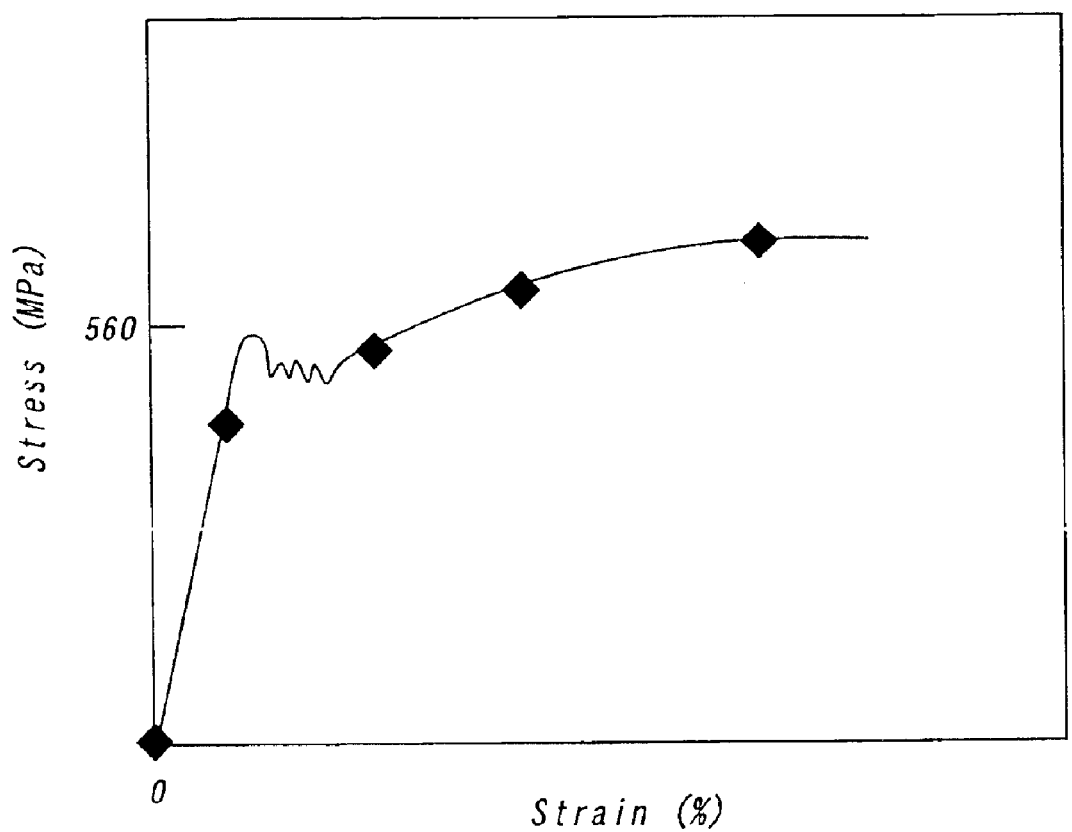
FIG. 2 is a stress-strain diagram of a low-alloy steel A533B samples obtained from the tensile test.

FIG. 2 shows a stress-strain curve derived from data obtained from a tensile test applied to a test sample made of low-alloy steel A533B. The tensile test demonstrated that the test sample was broken at the point where the stress a exceeded 663 MPa.

Incidentally, the "magnetization test for obtaining a minor hysteresis loop or minor hysteresis loop measurement" used herein refers to a magnetization test for obtaining a minor hysteresis loop where magnetic field amplitude $H_a$ applied to a test sample is definitely smaller (or is equal to the magnetic field intensity about two times as high as the coercive force of the test sample) than the magnetic field intensity required to magnetize the test sample to a saturation level. The applicants of the invention introduced the term "minor hysteresis loop measurement" to conveniently distinguish the present magnetization test from the conventional magnetization test where the magnetic field intensity (magnetic field intensity within the limits of about several to 10 times of the coercive force) is increased up to a level to saturate the magnetization tendency of a test sample for obtaining a conventional hysteresis loop (major hysteresis loop). In this specification, a physical quantity derived from a minor hysteresis loop of a test sample corresponding with a coercive force obtained from a major hysteresis loop, that is, the magnetic field intensity H at the point where the magnetic flux density B is zero will be called a pseudo coercive force Hc*.

Figure 3:
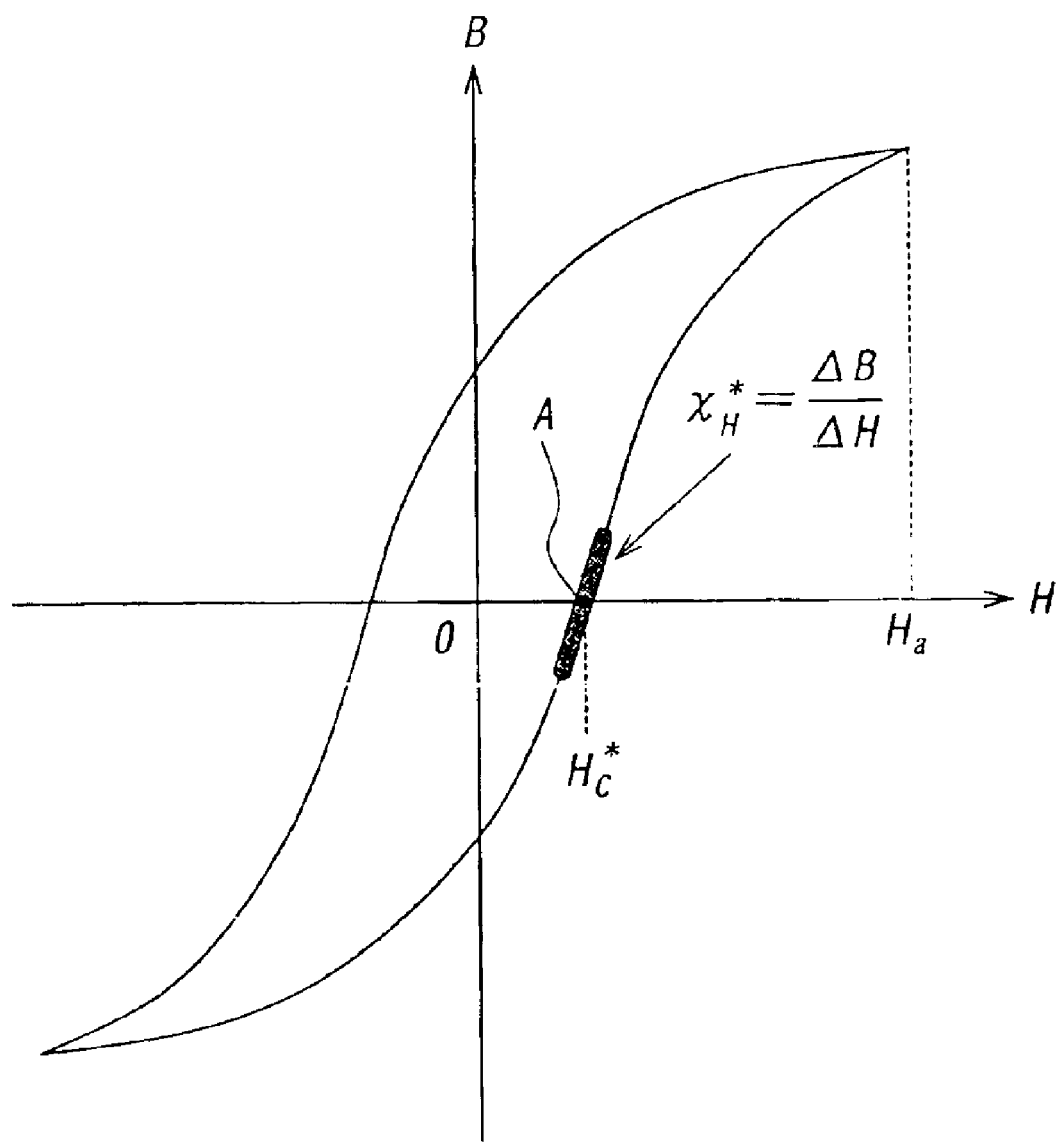
FIG. 3 is a minor hysteresis loop showing by an example of magnetic field amplitude $H_a$, pseudo coercive force Hc*, pseudo susceptibility $\chi_H^*$ at the pseudo coercive force Hc* obtained.

In the same manner, a parameter derived from the minor hysteresis loop corresponding to a susceptibility coefficient or the ratio of flux increment against magnetic field intensity increment at the point of H=Hc* (gradient of the minor hysteresis loop at H=Hc*) will be called a pseudo susceptibility coefficient at the pseudo coercive force $\chi_H^*$ (=ΔB/ΔH) (see FIG. 3). Both the pseudo coercive force and the pseudo susceptibility coefficient of a test sample change as a function of the magnetic field intensity H, and, if the intensity H is sufficiently high, they will correspond to the coercive force and the susceptibility coefficient determined for the test sample from its major hysteresis loop, respectively.

Then, appropriate applied stresses were determined for a test sample based on the result of the foregoing tensile test. The load was applied to the test sample to deform it, which was then subjected to a magnetization test for obtaining a minor hysteresis loop where the magnetic field was allowed to have certain magnetic field amplitude $H_a$. The same test was repeated a number of times with magnetic field amplitude $H_a$ being varied in a stepwise manner. A series of minor hysteresis loops were obtained from these tests.

Figure 4:
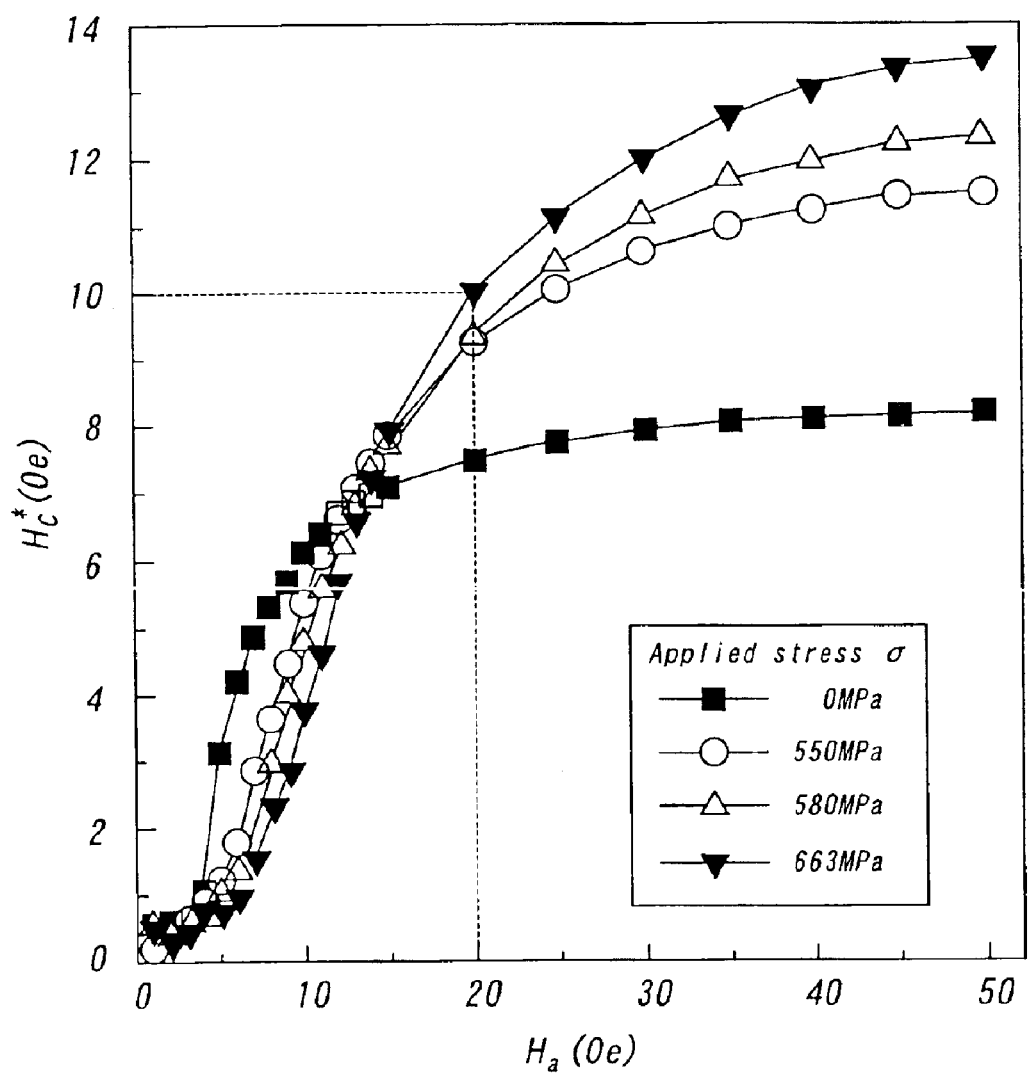
FIG. 4 is graphs showing the relation between the pseudo coercive force Hc* and magnetic field amplitude $H_a$ obtained from minor hysteresis loops of low-alloy steel A533B samples.
Figure 5:
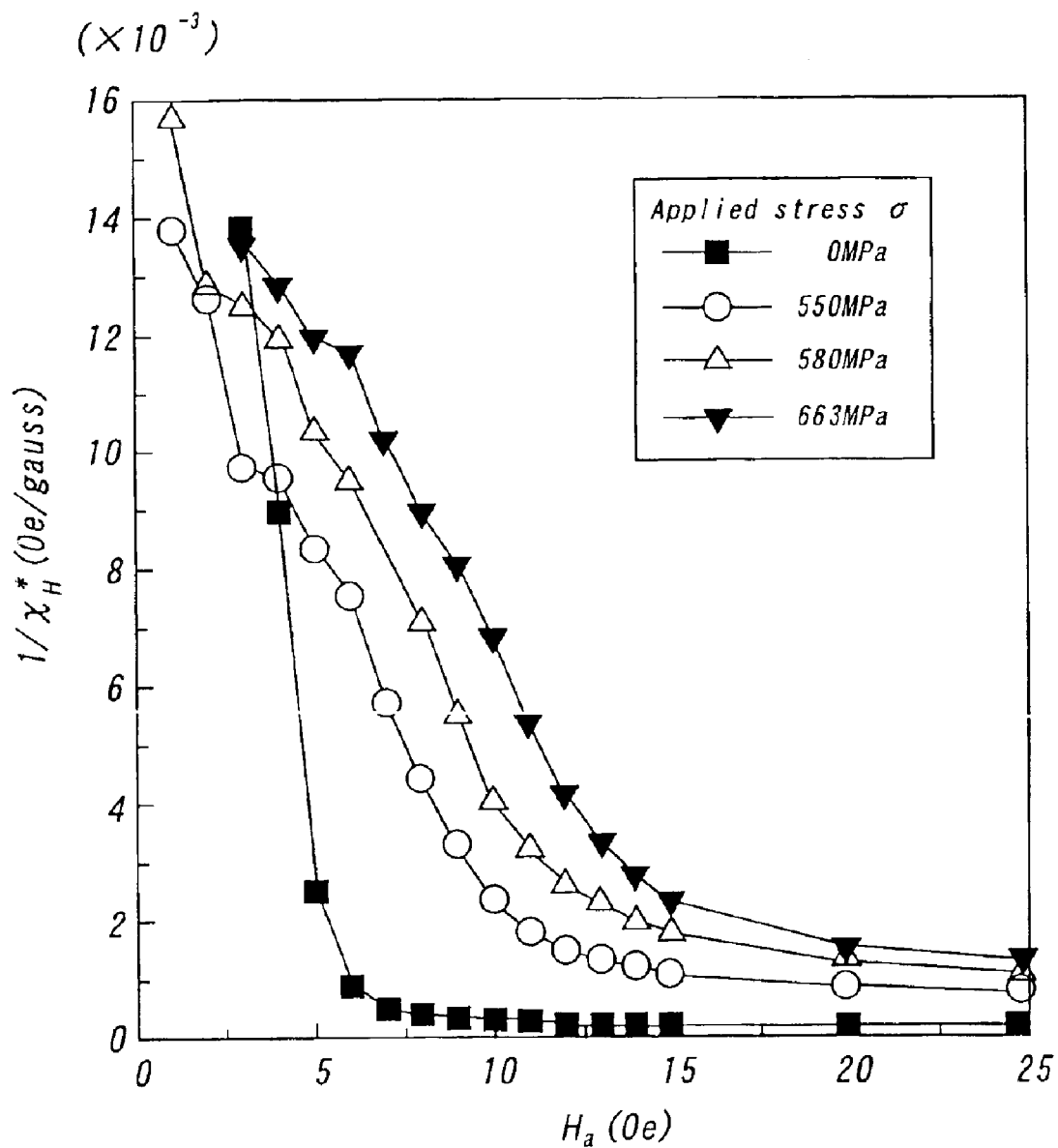
FIG. 5 is graphs showing the relation between the reciprocal $1/\chi_H^*$ of pseudo susceptibility $\chi_H^*$ at the pseudo coercive force Hc* and magnetic field amplitude $H_a$ obtained from minor hysteresis loops of low-alloy steel A533B samples.

FIGS. 4 and 5 show the relationship obtained from minor hysteresis loop measurements performed on a low-alloy steel A533B sample with stresses being applied. The results were obtained from the test sample prior to application of stress (σ=0 MPa) and after application of stresses (σ=550, 580 and 663 MPa). FIG. 4 shows that the relation between the pseudo coercive force Hc* and magnetic field amplitude $H_a$ changes depending on the externally applied stress. Likewise, FIG. 5 shows that the relation between the reciprocal of pseudo susceptibility at pseudo coercive force $(1/\chi_H^*)$, and magnetic field amplitude $H_a$ depending on the externally applied stress. The applied stress was chosen to be equal to 0 MPa and to the stress that develops just before breakage (σ=663 MPa), both of which had been obtained from a preparatory tensile test, and to intermediate values between the two values (σ=550 and 580 MPa). The solid squares (■), open circles (○), open triangles (△), and solid triangles (▼) represent the test results at the point where the applied stress was σ=0, 550, 580 and 663 MPa, respectively.

Incidentally, these results of minor hysteresis loop measurements were obtained at the point of magnetic field amplitude $H_a$ was varied from 0 to 60 Oe in a stepwise manner. However, magnetic field amplitude $H_a$ may vary at most up to about 10 Oe depending on a given test sample. To estimate aged deterioration of a construction material for a reactor pressure vessel using the hysteresis data of the material, it is necessary to use a magnetic field whose maximum value of magnetic field amplitude $H_a$ ranges from 50 to 100 Oe according to a conventional method.

However, according to the method of the present invention, magnetic field amplitude $H_a$ up to about 60 Oe is preferred in order to obtain precise and detailed data about aged deterioration of the same evaluating material. Even magnetic field amplitude $H_a$ up to only 20 Oe employed according to the present method can provide more detailed information about aged deterioration of the evaluating material than magnetic field amplitude $H_a$ usually employed in a conventional method as described later. In the tests described here, the stepwise increment of magnetic field amplitude $H_a$ was chosen to be 1 Oe. However, the stepwise increment of magnetic field amplitude $H_a$ may be smaller than this, and, needless to say, the smaller the stepwise increment of magnetic field amplitude is, the more detailed information about aged deterioration of an evaluating material will be obtained.

Figure 6:
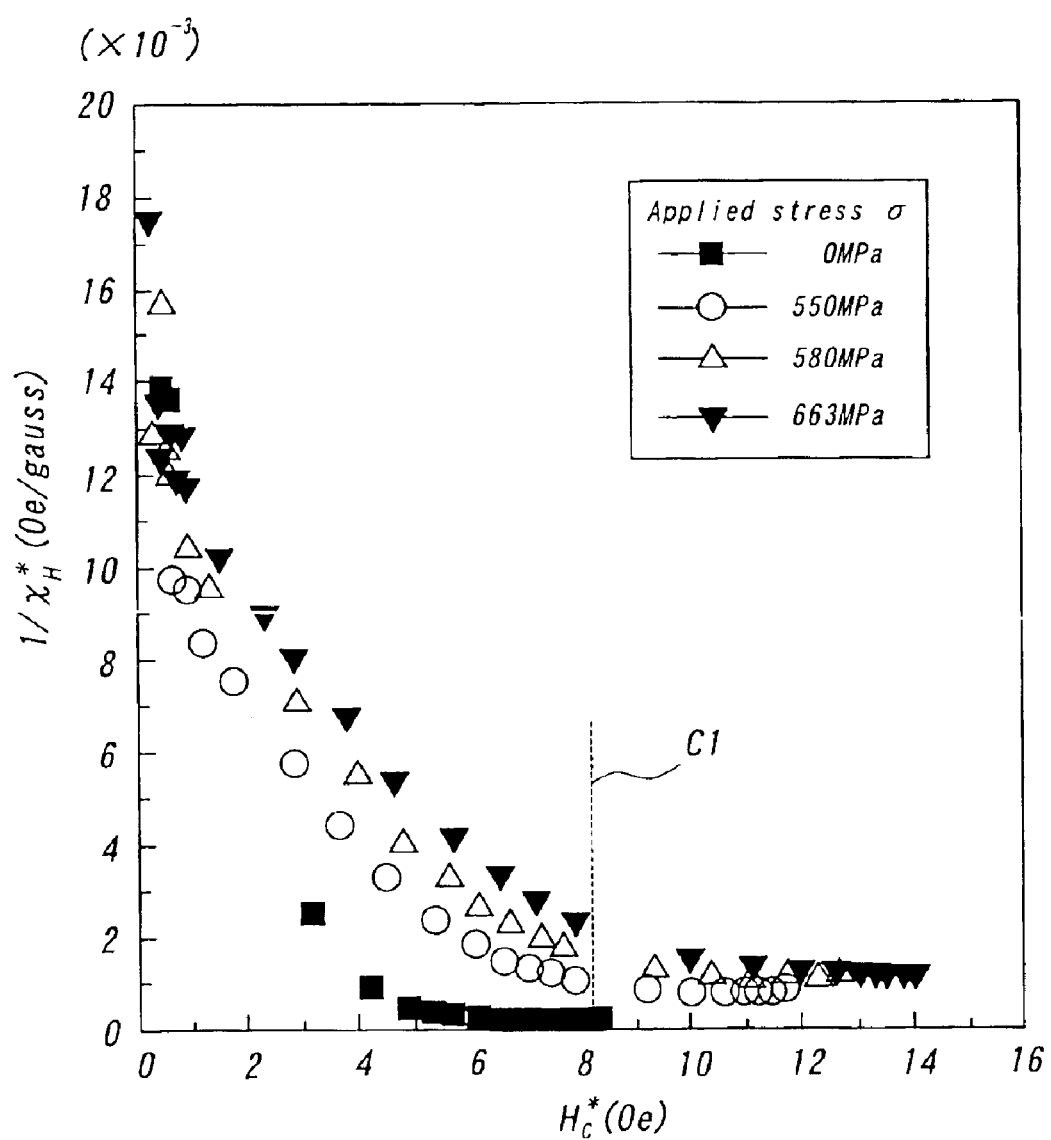
FIG. 6 is graphs showing the relation between the reciprocal $1/\chi_H^*$ at pseudo susceptibility $\chi_H^*$ and the pseudo coercive force Hc* obtained from minor hysteresis loops of low-alloy steel A533B samples after the stresses of 0 MPa, 550 MPa, 580 MPa and 663 MPa, respectively.
Figure 7:
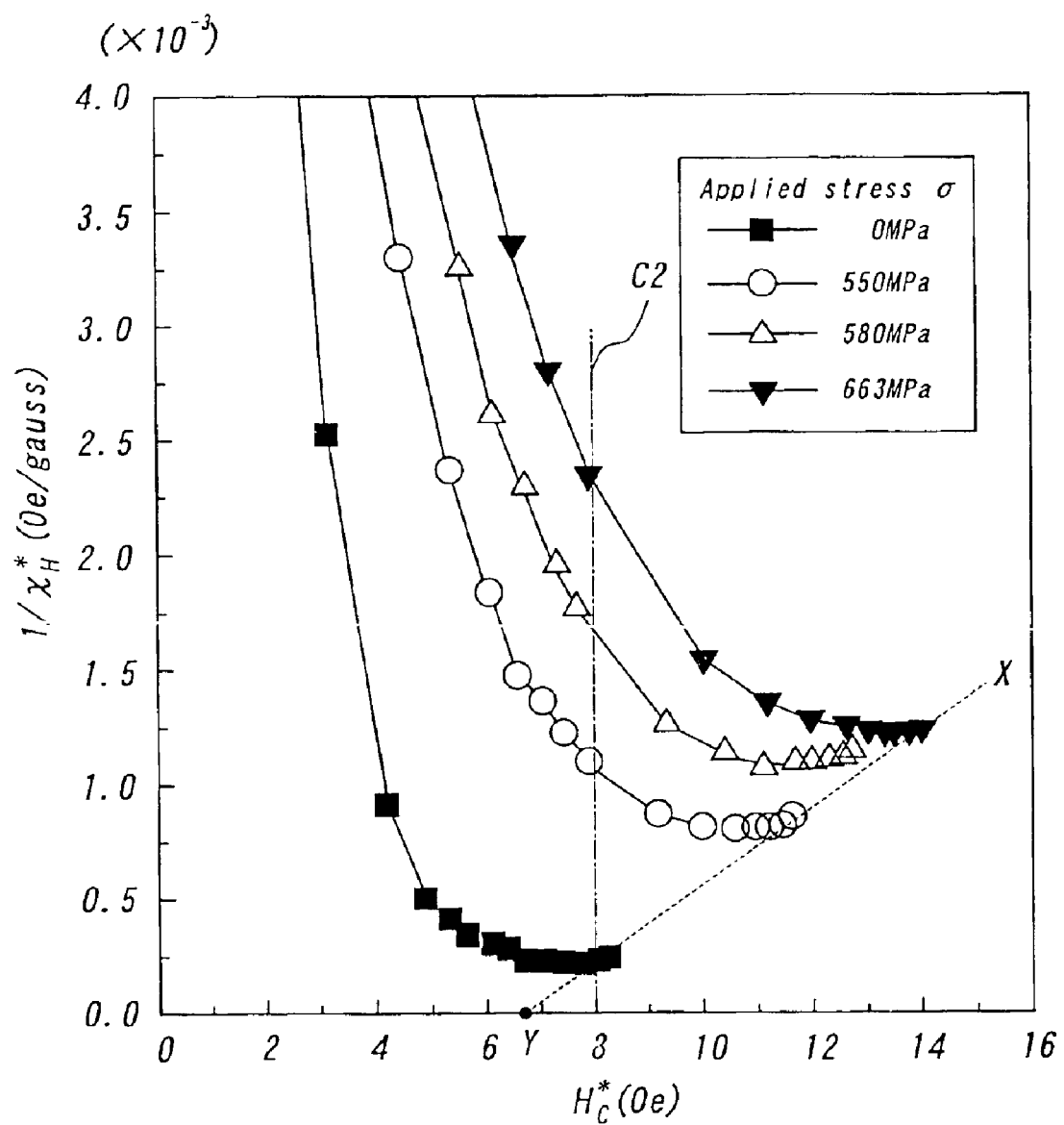
FIG. 7 is an enlarged graph of an interest part of the curves shown in FIG. 6.

FIG. 6 illustrates the relation between the reciprocal $1/\chi_H^*$ of pseudo susceptibility $\chi_H^*$ at pseudo coercive force Hc* and the pseudo coercive force Hc*, the pseudo susceptibility data being obtained from the results of FIGS. 4 and 5. FIG. 7 puts a focus on a lower range (0 to 4 Oe/gauss) of the reciprocal $1/\chi_H*$ of pseudo susceptibility $\chi_H*$ at pseudo coercive force Hc* as depicted in FIG. 6, and the curves are enlarged in the range. The symbols in FIGS. 6 and 7 have the same meanings as those of FIGS. 4 and 5: the solid squares, open circles, open triangles and solid triangles represent results at the points where the applied stresses σ=0, 550, 580 and 663 MPa, respectively.

As seen from FIGS. 6 and 7, the relation between the reciprocal $1/\chi_H*$ of pseudo susceptibility $\chi H*$ at pseudo coercive force Hc* and the pseudo coercive force Hc* changes with the increase of applied stress σ. It should be noted that in FIGS. 6 and 7, the relation between the reciprocal $1/\chi_H*$ of pseudo susceptibility $\chi_H*$ at pseudo coercive force Hc* and the pseudo coercive force Hc* represented by solid triangles is derived from a sample at the threshold of breakage. As shown in FIG. 7, the terminal (lowest) ends of curves under different stresses obtained at magnetic field amplitude $H_a$ ($H_a$ being 60 Oe in this particular example) form, at the points where connected together, a straight line represented by the line X-Y in the figure, as long as the curves are obtained from samples of the alloy of the same kind.

This research by the present Inventor revealed that there exists an intimate correlation between the externally applied stress (which may be replaced with internal stress), and the relation between the reciprocal $1/\chi_H*$ of pseudo susceptibility $\chi_H*$ at pseudo coercive force Hc* and the pseudo coercive force Hc*.

It was revealed by further experiments that the externally applied stress exerts a similar effect on the relation here concerned even in the case that other ferromagnetic construction materials than those made of low-alloy steel A533B were used as test samples, and that the effect is ascribed to the increased dislocations as a result of externally applied stress and changes depending on the grain size constituting the steel material, precipitates and addition of trace elements.

Figure 8:
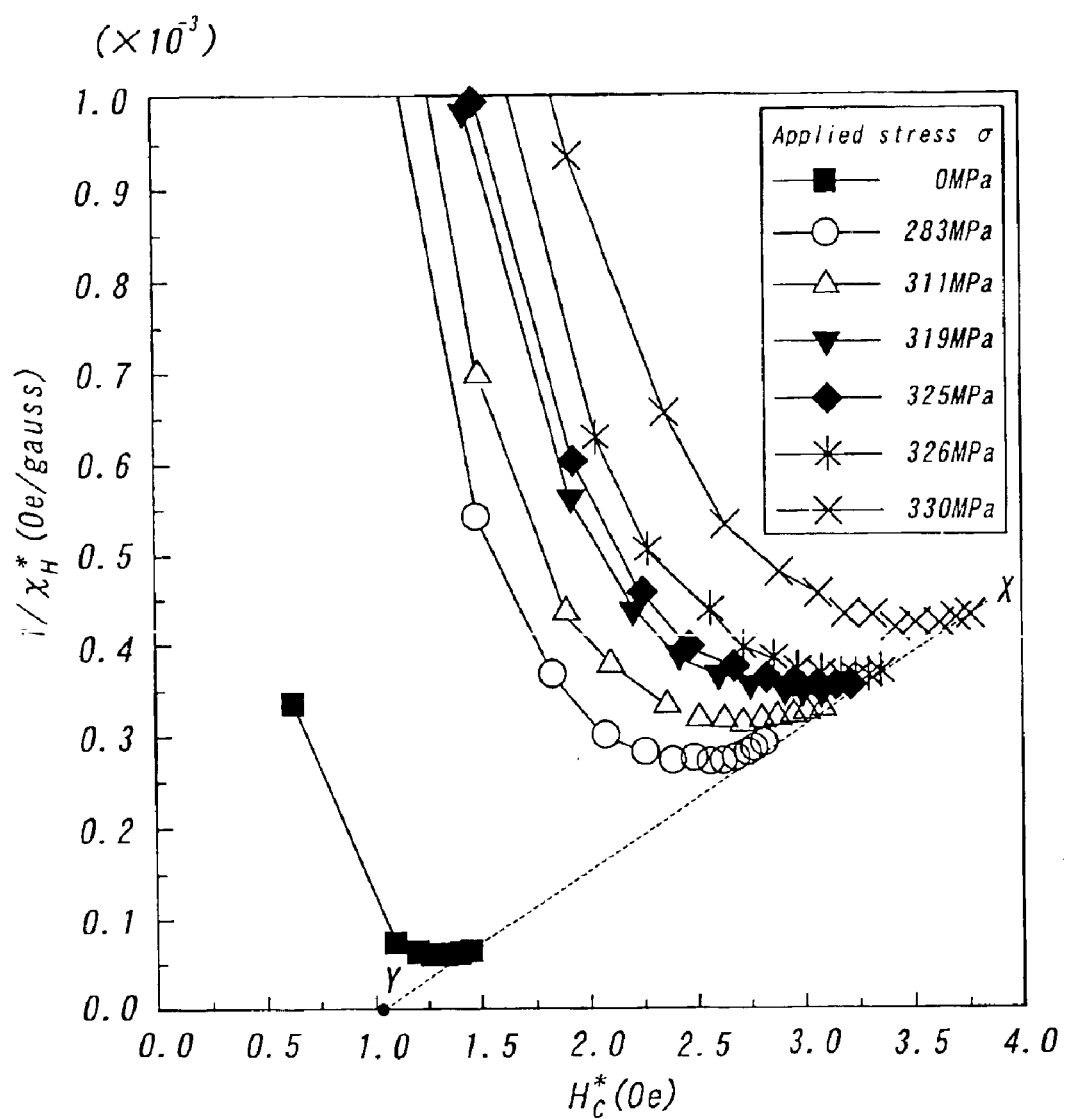
FIG. 8 is graphs showing the relation between the reciprocal $1/\chi_H^*$ of pseudo susceptibility $\chi_H^*$ and pseudo coercive force Hc* obtained from minor hysteresis loops of pure iron samples with an average grain size of 37 μm, after plastic deformation.

FIG. 8 shows the results of minor hysteresis loop measurements performed on a pure iron sample having an average grain size of 37 µm. The figure shows graphs relating the reciprocal of pseudo susceptibility at pseudo coercive force $1/\chi_H*$ with the pseudo coercive force Hc*. Based on a preliminary tensile test, the externally applied stresses σ were chosen to be 0 MPa and between 283 and 330 MPa. The results obtained at the point where the applied stresses σ=0, 283, 311, 319, 325, 326 and 330 MPa were plotted by solid squares, open circles, open triangles, solid triangles, solid diamonds, asterisks, and crosses, respectively. The maximum value of magnetic field amplitude $H_a$ was 15 Oe.

As shown in FIG. 8, the terminal (lowest) ends of curves under different stresses obtained at the fully large magnetic field amplitude $H_a$ ($H_a$ being 15 Oe in this particular example) form, where connected together, a straight line represented by the line X-Y in the figure, as long as the curves are obtained from the same kind of alloy sample with the same grain size. As described above with regard to the sample made of low-alloy steel A533B, FIG. 8 also shows that the corresponding plots obtained at magnetic field amplitude $H_a$ from the test sample with a certain grain size, where connected, a straight line represented by the line X-Y.

Moreover, the straight line obtained from a pure iron sample shown in FIG. 8 is different from the counterpart obtained from a low-alloy steel A533B sample shown in FIG. 7: its gradient and intercept (point Y) on the abscissa (representing the magnitude of pseudo coercive force Hc*) are different from those of the latter, for example. By detailed research of the Inventor, it found that the point Y takes a larger value as the grain size becomes smaller. Therefore, it is possible to predict the grain size or crystallizing substances of an evaluating material or to classify evaluating materials according to their grain size by performing a minor hysteresis loop measurement on the evaluating material under various stresses, and evaluating the point Y based on the test results.

In the evaluating method of the present invention, an applied stress σ, i.e. a deformation stress is used as parameter for inspecting the changes of the density and distribution of dislocations in materials before the initiation of cracks. This is based on conventional observation that the deformation stress has an intimate correlation with the dislocation density in that material. To put it more specifically, at the initial stage of deformation, the dislocation density increases in proportion with the applied stress. And at the intermediate and later stage of deformation, the applied stress increases in proportion with the square root of the dislocation density. At the final stage of deformation, the dislocation density reaches a maximum and cracks are initiated in the evaluating sample. Finally, the evaluating sample leads to the breakage of the sample. As seen from above it is possible to follow change of the dislocation density by utilizing the dependence of the relation between the reciprocal $1/\chi_H*$ of pseudo susceptibility $\chi_H*$ at pseudo coercive force Hc* and the pseudo coercive force Hc* on applied stresses.

As seen from inspection of the relation between the reciprocal $1/\chi_H*$ of pseudo susceptibility $\chi_H*$ at pseudo coercive force Hc* and the pseudo coercive force Hc* in FIGS. 7 and 8, a similar relation which can be used for evaluating aged deterioration of an evaluating sample may be obtained without resorting to the above minor hysteresis loop measurement.

In this simplified method, smaller Hc* values are used for evaluating aged deterioration of an evaluating sample. For example, to obtain curves as shown in FIGS. 6 and 7, the magnetic field was allowed to have a magnetic field amplitude $H_a$ as high as 60 Oe. However, even when the maximum value of magnetic field amplitude $H_a$ is, for example, 20 Oe or lower, a similar relation between the reciprocal $1/\chi_H*$ of pseudo susceptibility $\chi_H*$ at pseudo coercive force Hc* and the pseudo coercive force Hc* can be obtained by plotting corresponding points on the left side of the dotted line C1 of FIG. 6 or of the dot-dash line C2 of FIG. 7. The evaluation results obtained by the simplified method were found satisfactory.

Figure 9:
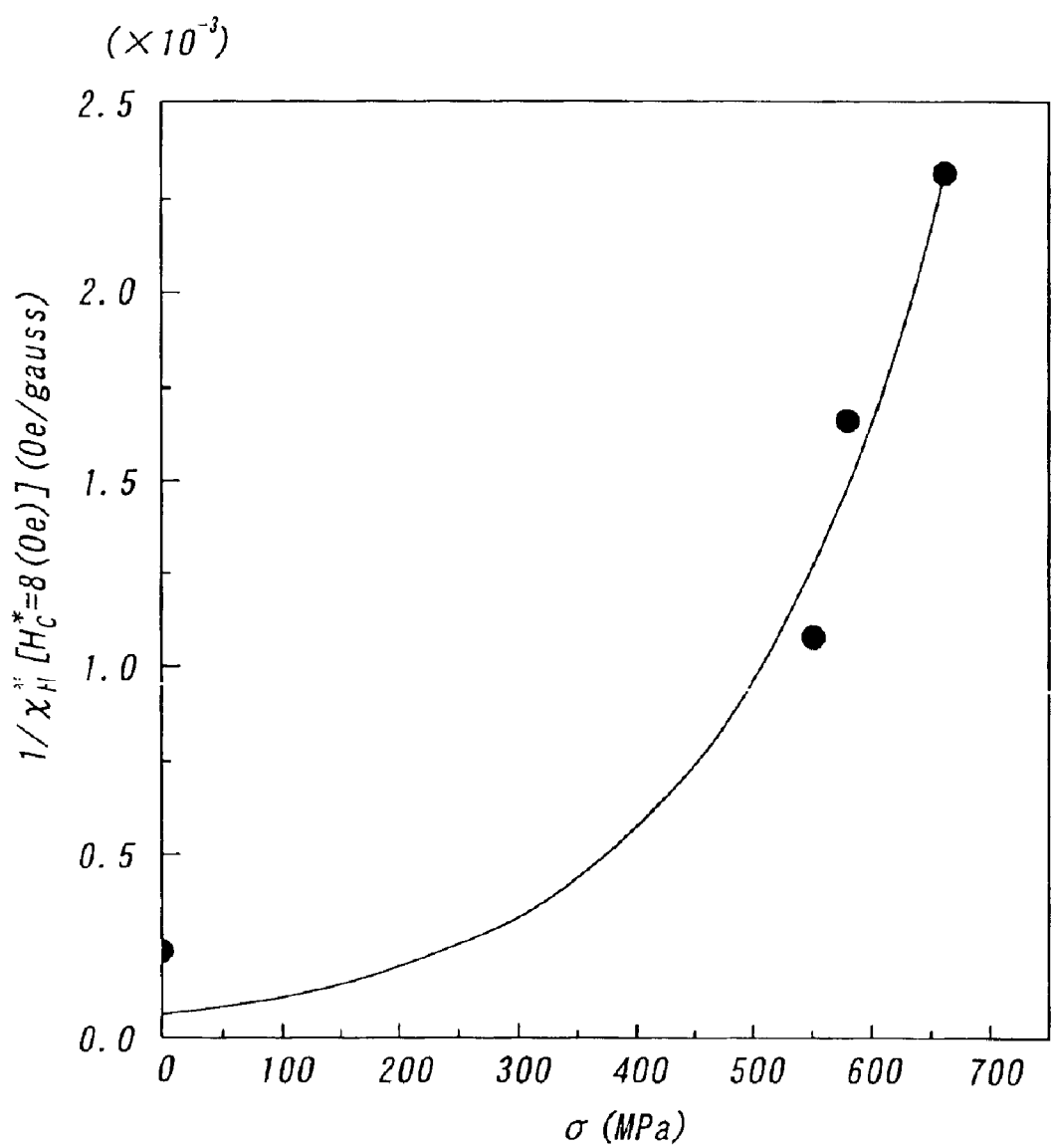
FIG. 9 is a graph showing the relation between the deformation stress (applied stress) σ and the reciprocal $1/\chi_H^*$ of pseudo susceptibility $\chi_H^*$ at the pseudo coercive force Hc*=8 Oe obtained from minor hysteresis loops of low-alloy steel A533B samples.

FIG. 9 illustrates the relation between the reciprocal $1/\chi_H*$ of pseudo susceptibility $\chi_H*$ at pseudo coercive force Hc* and the deformation stress σ (in MPa) at the point where an evaluating sample had a pseudo coercive force Hc*=8 Oe obtained from the results shown in FIGS. 6 and 7 (corresponding points being arranged along the dashed line C1 of FIG. 6 and the dot-dash line C2 of FIG. 7). According to the curve shown in FIG. 9, it is possible to follow the change of the extent of aged deterioration of an evaluating sample or of the dislocation density in the sample, by performing a minor hysteresis loop measurement on the sample with magnetic field amplitude being kept comparatively low, and by evaluating the reciprocal $1/\chi_H*$ of pseudo susceptibility $\chi_H*$ at pseudo coercive force Hc* based on the minor hysteresis loop data. This means, it is possible to satisfactorily evaluate aged deterioration of an evaluating sample by referring to information obtained from a minor hysteresis loop measurement where magnetic field amplitude is kept comparatively low.

The reciprocal of a susceptibility $1/\chi_H^*$ obtained from minor hysteresis loop data represents the reluctance of movements of domain walls, and the pseudo coercive force of the same hysteresis data represents the threshold at which domain walls start to move. It is known that the potential energy of domain wall movements is determined by dislocations, grain boundaries, precipitations, and other lattice defects. In contrast, the applicants of the invention confirmed that the pseudo coercive force Hc* and the reciprocal $1/\chi_H^*$ of pseudo susceptibility $\chi_H^*$ at pseudo coercive force Hc* of a sample correspond to the coercive force Hc and susceptibility obtained from a major hysteresis loop of the sample, respectively. Therefore, it is possible to obtain an overview of the potential energy of domain wall movements of an evaluating sample by varying magnetic field amplitude $H_a$ applied to the evaluating sample.

According to the evaluating method of the present invention described above, the evaluation information acquiring step consists of obtaining the first relation (relation as represented, for example, in FIG. 4) between the pseudo coercive force Hc* and magnetic field amplitude $H_a$, and the second relation between the reciprocal $1/\chi_H^*$ of pseudo susceptibility $\chi_H^*$ at pseudo coercive force Hc* and magnetic field amplitude $H_a$ (relation as represented, for example, in FIG. 5). The magnitude and distribution of forces to which domain walls are exposed are derived from the information obtained by the evaluation information acquiring step. Therefore, it is possible according to the present method to distinguish various lattice defects involved in the development of aged deterioration of a material, and to quantify the involvement of individual defects.

Thus, it is possible to evaluate aged deterioration of ferro-magnetic construction materials used for constructing a reactor pressure vessel as well as to distinguish various lattice defects of the material responsible for its aged deterioration, and to separately quantify involved individual defects, by evaluating the pseudo coercive force Hc* and the reciprocal $1/\chi_H^*$ of pseudo susceptibility $\chi_H^*$ at pseudo coercive force Hc*, and obtaining the first and second relations via the evaluation information acquiring step. Namely, it is possible according to the present method to evaluate aged deterioration of a material more minutely, precisely and comprehensively than it is possible with conventional methods. Moreover, both the evaluation information acquiring step and the measurement step concern with acquisition of pseudo coercive forces Hc* and pseudo susceptibilities $\chi_H^*$ at pseudo coercive force Hc* from obtained minor hysteresis loops under a magnetic field whose maximum value of magnetic field amplitude $H_a$ is about two times as high as that of the coercive force, that is, according to the present method necessary information can be obtained using a magnetic field whose maximum value of magnetic field amplitude $H_a$ is comparatively low.

According to conventional methods, to obtain a major hysteresis loop, it is necessary to apply a magnetic field whose maximum value of magnetic field amplitude is comparatively high, that is, 50–100 Oe. However, according to the present method, sufficient information about aged deterioration of an evaluating material can be obtained by applying to the material a magnetic field whose maximum value of magnetic field amplitude is about 20 Oe or less.

Alternatively, according to the present evaluating method, the evaluation information acquiring step may comprise obtaining the third relation of the relation between the reciprocal $1/\chi_H^*$ of susceptibility $\chi_H^*$ at pseudo coercive force Hc* and the pseudo coercive force Hc* as represented, for example, in FIGS. 7 and 8 from the first and second relations, and the evaluation may comprise evaluating aged deterioration of an evaluating ferromagnetic construction material using the third relation. The curve representing the third relation (e.g., those of FIGS. 7 and 8) suggests the form and magnitude of potential energy of domain wall movements, and thus it is possible to precisely and easily evaluate aged deterioration of the evaluating material based on the curve.

It should be noted here that the pseudo susceptibility $\chi_H^*$ at pseudo coercive force Hc* and pseudo coercive force Hc* are quantities defining the magnetic properties of an evaluating material. More specifically, the relation between the pseudo susceptibility $\chi_H^*$ at pseudo coercive force Hc* and pseudo coercive force Hc* do not involve external parameters such as the magnetic field amplitude $H_a$. Therefore the relation is determined solely by internal factors. Accordingly, the relation involving the pseudo susceptibility $\chi_H^*$ at pseudo coercive force Hc* and pseudo coercive force Hc* solely based on those quantities provides information about the internal factors of the evaluating material including lattice defects, and is independent of external factors.

Alternatively, according to the present evaluating method, the evaluation information acquiring step may comprise obtaining the fourth relation of the relation between the reciprocal $1/\chi_H^*$ of susceptibility $\chi_H^*$ at pseudo coercive force Hc* and the applied stress σ (as represented, for example, in FIG. 9) from the first, second and third relations, and the evaluation step may comprise evaluating aged deterioration of an evaluating ferromagnetic construction material using the fourth relation.

According to this method, it is possible to quantitatively determine the values of deformation stress between a state prior to aged deterioration and a state at initiation of cracks, by obtaining the pseudo susceptibility $\chi_H^*$ of the evaluating material and evaluating the reciprocal of pseudo susceptibility at pseudo coercive force $1/\chi_H^*$. Thus, it is possible, for a given ferromagnetic material, to more precisely evaluate its aged deterioration and predict its expectable life than it is possible with the foregoing methods. It is further possible to appreciate change of the dislocation density from the values of deformation stress obtained via the evaluation information acquiring step.

Alternatively, according to the method for nondestructively evaluating aged deterioration of ferromagnetic construction materials of the present invention, the evaluation information acquiring step may comprise obtaining the fifth relation of the relation between the pseudo hysteresis loss $W_F^*$ and magnetic field amplitude $H_a$, the pseudo hysteresis loss $W_F^*$ being defined as an area enclosed by a minor hysteresis loop, in addition to the first relation of the relation between the pseudo coercive force Hc* and magnetic field amplitude $H_a$, and the measurement step may comprise measuring the pseudo coercive force Hc* which is the magnetic field intensity H at the point where the magnetic flux density B is zero, and the pseudo hysteresis loss $W_F^*$ which is an area enclosed by a minor hysteresis loop.

Figure 10:
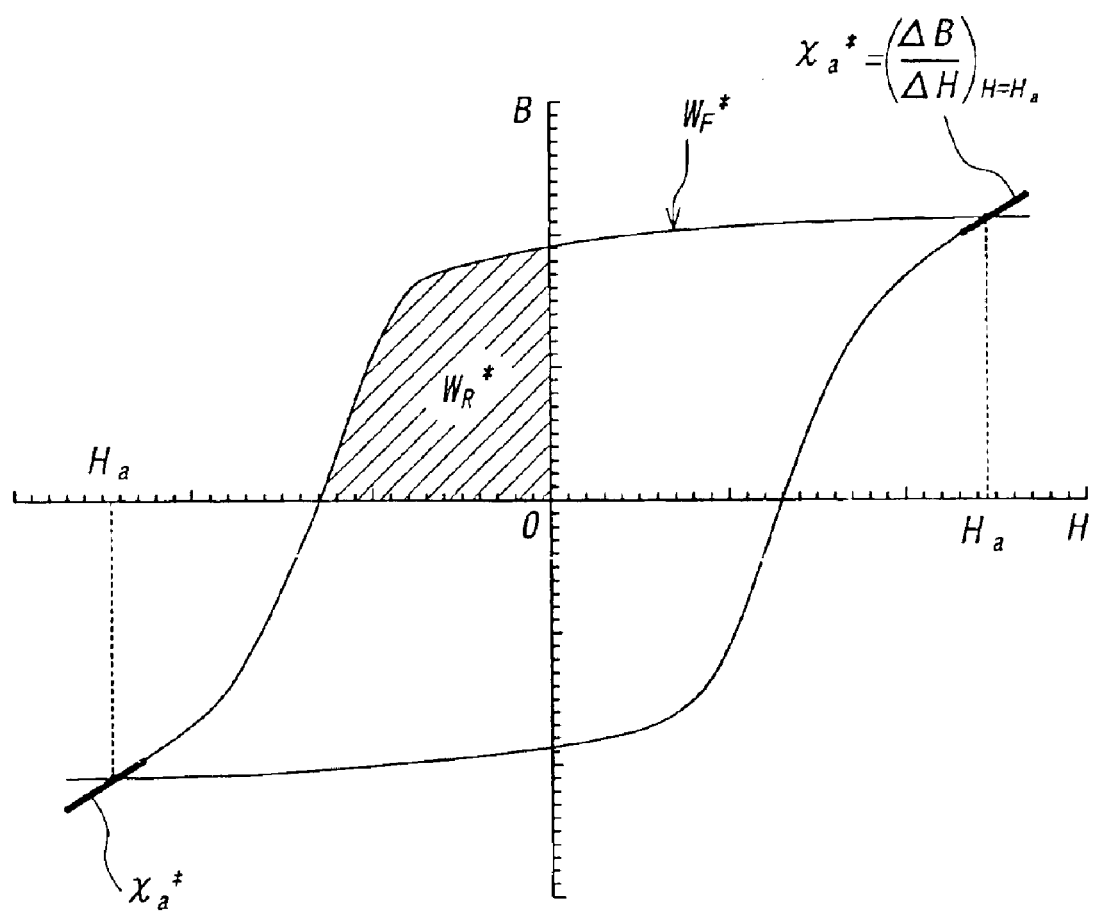
FIG. 10 is a minor hysteresis loop exemplifying how a pseudo hysteresis loss $W_F^*$ and a pseudo remanence work $W_R^*$.

According to this version of the evaluating method of the present invention, similarly to the foregoing methods, stresses appropriately chosen according to the results of a previous tensile test are applied to an evaluating ferromagnetic material; the stresses are removed and the deformed evaluating material is exposed to a magnetic field whose maximum value of magnetic field amplitude is varied in a stepwise manner to obtain thereby minor hysteresis loops. In this specification, as shown in FIG. 10, the area enclosed by a minor hysteresis loop is defined as a pseudo hysteresis loss $W_F^*$, and the fractional area (shaded area in FIG. 10) belonging to the second quadrant of pseudo hysteresis loss $W_F^*$ is defined as a pseudo remanence work $W_R^*$ which is described later.

Effects and advantages obtained from the evaluating method as described above will be described below with reference to minor hysteresis loop data obtained from a test sample made of low-alloy steel A533B.

Figure 11:
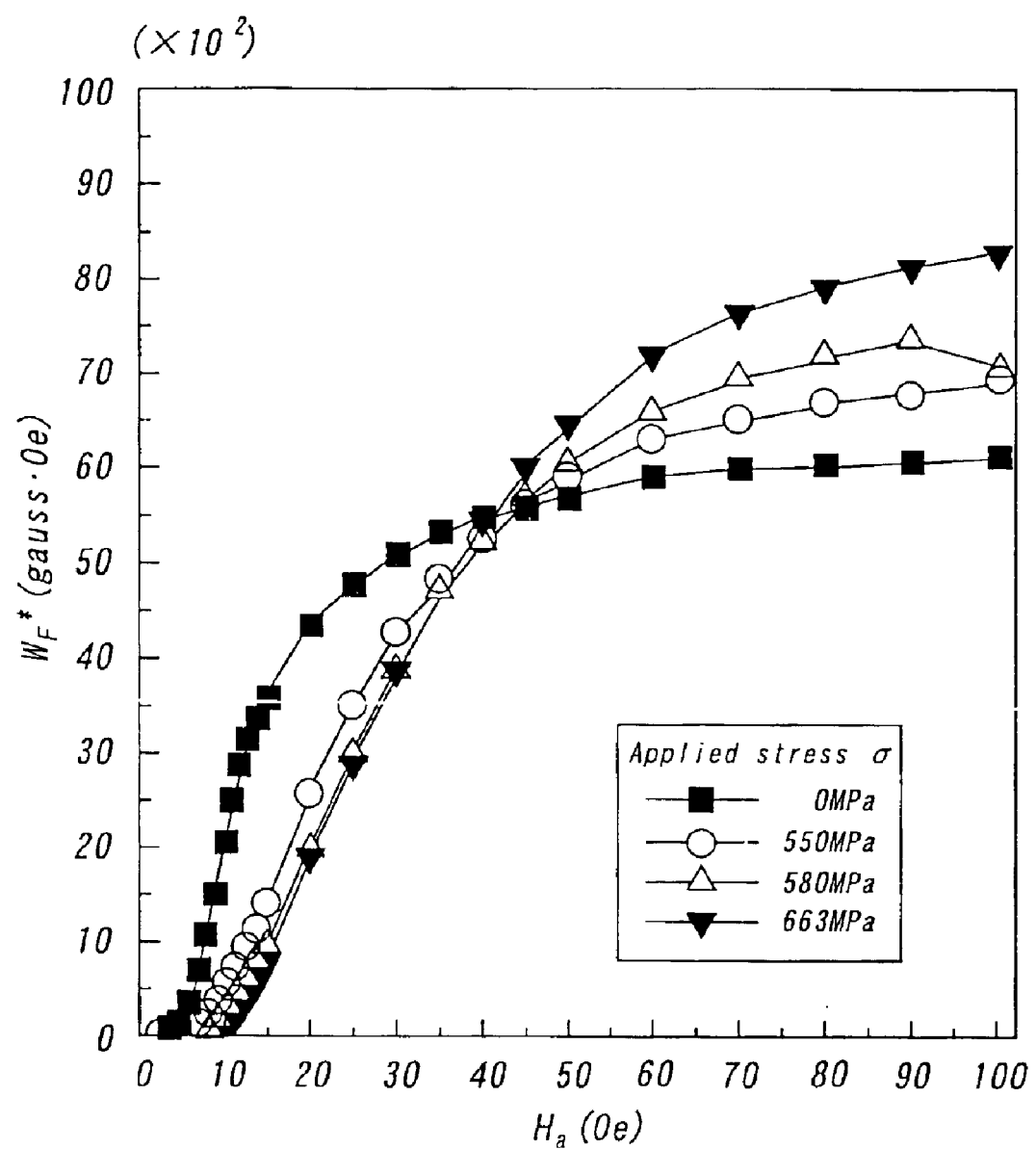
FIG. 11 is graphs exemplifying the dependence of the relation between the pseudo hysteresis loss $W_F^*$ and magnetic field amplitude $H_a$ (fifth relation) on stresses concomitantly applied, obtained from minor hysteresis loops of low-alloy steel A533B samples.

The first relation of the relation between the pseudo coercive force Hc* and magnetic field amplitude $H_a$ (or the relation obtained by the foregoing method and represented in FIG. 4) and the fifth relation of the relation between the pseudo hysteresis loss $W_F^*$ and magnetic field amplitude $H_a$ were obtained from a minor hysteresis loop measurement performed on an evaluating sample. FIG. 4 shows the dependence of the first relation on applied stresses while FIG. 11 shows the dependence of the fifth relation on applied stresses. Applied stresses used for obtaining curves of FIG. 11 were chosen, as done for obtaining the curves of FIG. 4, according to the results of a previous tensile test, that is, zero stress ($\sigma$=0 MPa), the stress at the threshold of breakage ($\sigma$=663 MPa) and intermediate stresses between the two extreme values ($\sigma$=550 and 580 MPa). In FIG. 11, the results obtained at the points where the applied stress $\sigma$=0, 550, 580 and 663 MPa were plotted by solid squares, open circles, open triangles, and solid triangles, respectively.

Figure 12:
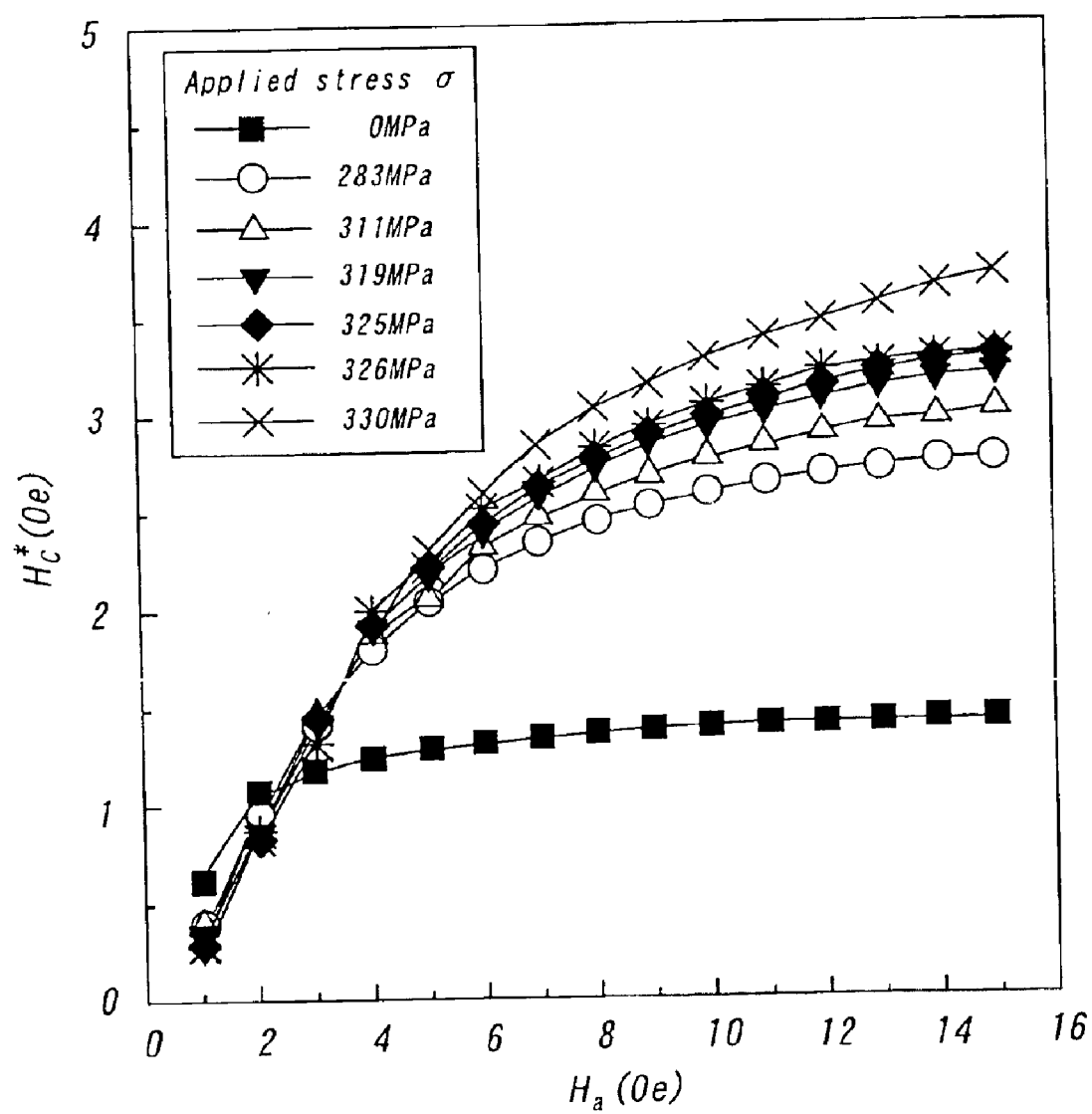
FIG. 12 is graphs exemplifying the dependence of the relation between the pseudo coercive force Hc* and magnetic field amplitude $H_a$ (first relation) on stresses concomitantly applied, obtained from minor hysteresis loops of polycrystalline pure iron samples (average grain diameter of 37 μm)
Figure 13:
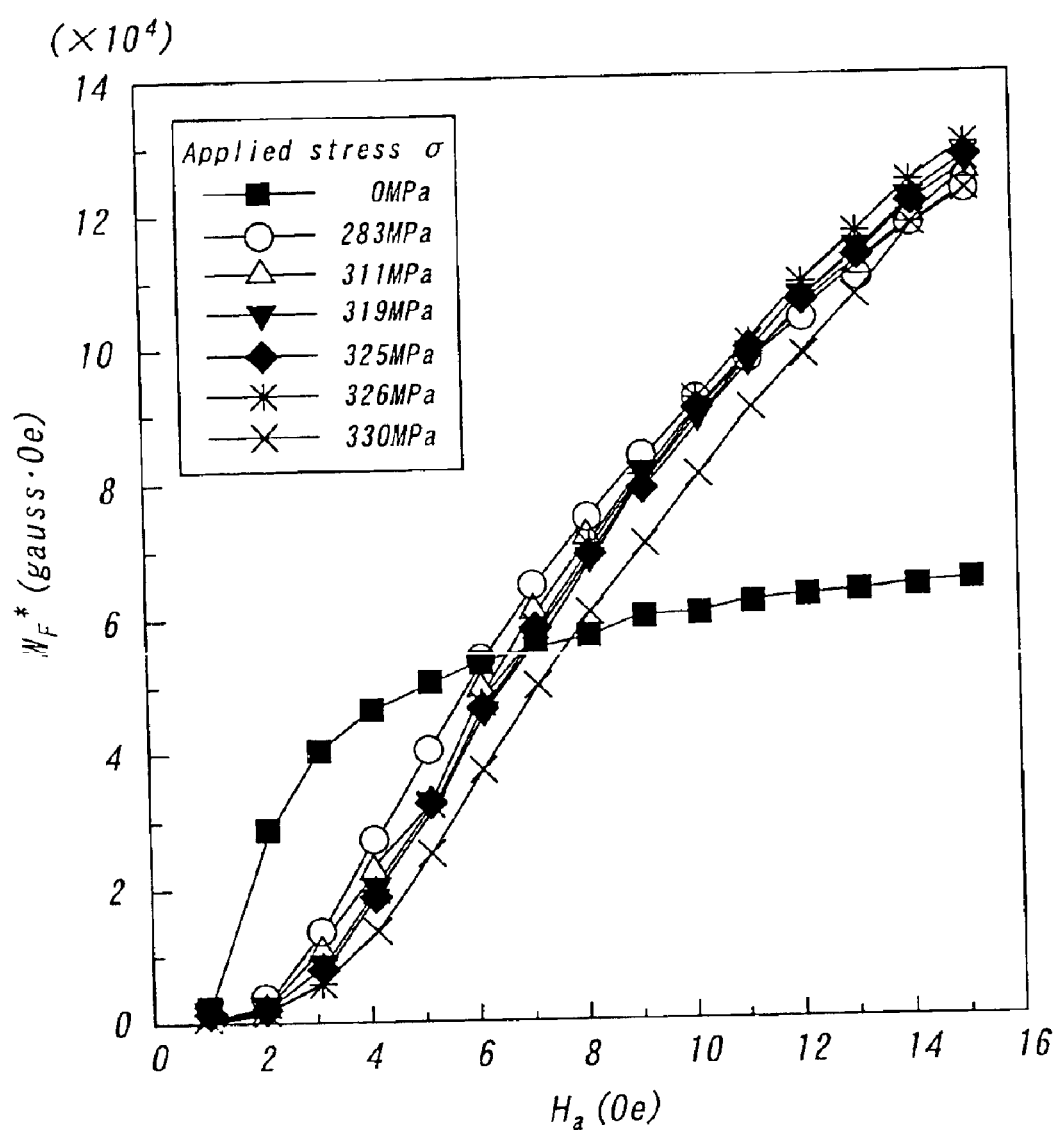
FIG. 13 is graphs exemplifying the dependence of the relation between the pseudo hysteresis loss $W_F^*$ and magnetic field amplitude $H_a$ (fifth relation) on stresses concomitantly applied, obtained from minor hysteresis loops of polycrystalline pure iron samples (average grain diameter of 37 μm)

Similarly, evaluating samples made of polycrystalline pure iron (average grain size being 37 $\mu$m) were subjected to tensile test and minor hysteresis loop measurement, and the relation between the pseudo coercive force Hc* and magnetic field amplitude $H_a$ (first relation), and the relation between the pseudo hysteresis loss $W_F^*$ and magnetic field amplitude $H_a$ (fifth relation) derived from the tests were obtained and shown in FIGS. 12 and 13, respectively. The curves of the figures show the dependence of both relations on applied stresses. The applied stresses were chosen, based on the results of the tensile test, to take intermediate values between the two extreme values of 0 and 330 MPa with the two extreme values included. Thus, in FIGS. 12 and 13, the results obtained at the points where the applied stresses $\sigma$=0, 283, 311, 319, 325, 326, and 330 MPa were plotted by solid squares, open circles, open triangles, solid triangles, solid diamonds, asterisks, and crosses, respectively.

Figure 14:
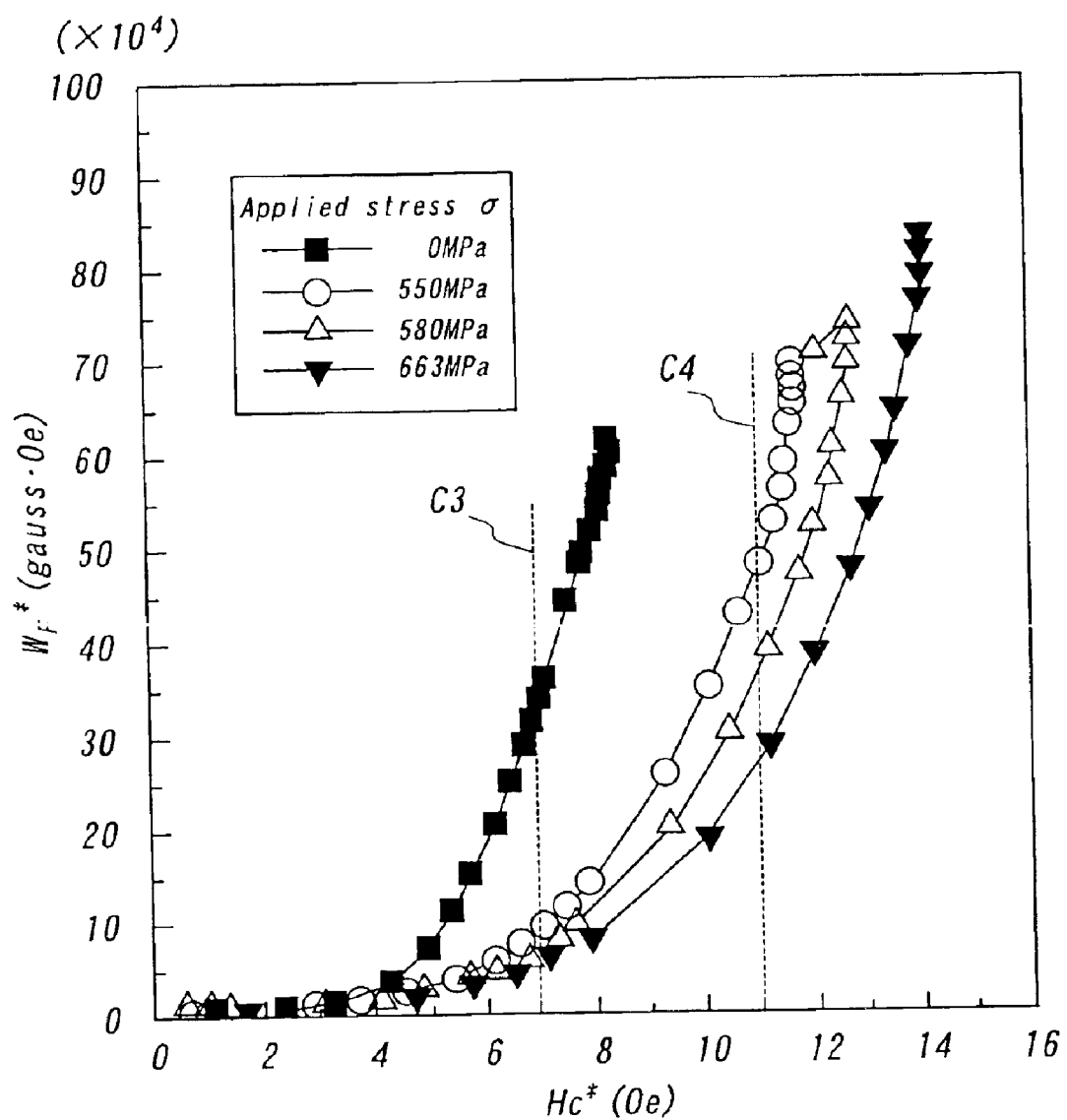
FIG. 14 is graphs exemplifying the dependence of the relation between the pseudo hysteresis loss $W_F^*$ and the pseudo coercive force Hc* (sixth relation) on stresses concomitantly applied, obtained from minor hysteresis loops of low-alloy steel A533B samples.
Figure 15:
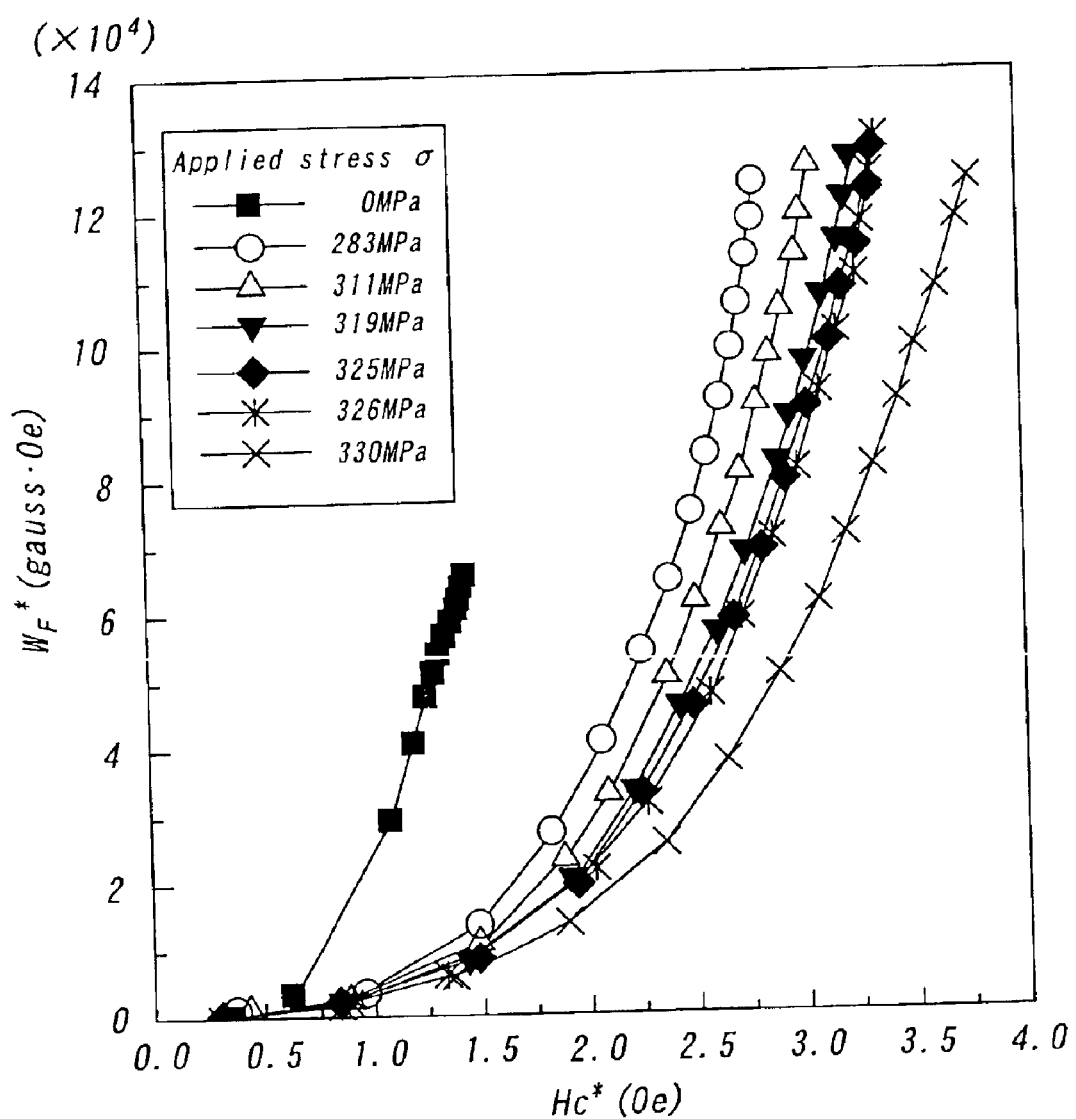
FIG. 15 is graphs exemplifying the dependence of the relation between the pseudo hysteresis loss $W_F^*$ and the pseudo coercive force $Hc^*$ (sixth relation) on stresses concomitantly applied, obtained from minor hysteresis loops of polycrystalline pure iron samples (average grain diameter of 37 $\mu$m)

FIG. 14 illustrates the sixth relation of the relation between the pseudo hysteresis loss $W_F^*$ and the pseudo coercive force Hc* obtained from the first relation as depicted in FIG. 4 and the fifth relation as depicted in FIG. 5. FIG. 15 illustrates the sixth relation of the relation between the pseudo hysteresis loss $W_F^*$ and the pseudo coercive force Hc* for an evaluating sample made of polycrystalline pure iron obtained from the fifth relation as depicted in FIG. 12 and the fifth relation as depicted in FIG. 13.

As seen from FIGS. 14 and 15, the pseudo hysteresis loss $W_F^*$ expressed as a function of pseudo coercive force Hc* increases with the increase of applied stress $\sigma$. It should be noted that the relation between the pseudo hysteresis loss $W_F^*$ and the coercive force Hc* obtained at an applied stress $\sigma$=663 MPa represents the state of an evaluating sample exposed to a breaking stress.

The applicants of this invention demonstrated from the results that there is an intimate correlation between the applied stress (which may be replaced with internal stress) and the sixth relation of the relation between pseudo hysteresis loss $W_F^*$ and pseudo coercive force Hc*. Moreover, because the sixth relation of the relation between the pseudo hysteresis loss $W_F^*$ and the pseudo coercive force Hc* may vary depending on evaluating materials, it is possible to distinguish the evaluating materials from each other using data of the sixth relation.

As seen from the relations between pseudo hysteresis loss $W_F^*$ and pseudo coercive force Hc* shown in FIGS. 14 and 15, it is possible to evaluate aged deterioration of an evaluating material without resorting to curves extending over a full range.

Namely, it is possible to follow the aged deterioration of an evaluating material by comparing curves in comparatively low pseudo coercive forces Hc*. Take, for example, the curves of FIG. 14 at a pseudo coercive force Hc*=7 Oe (dashed line C3 in the figure) and at a pseudo coercive force Hc*=11 Oe (dashed line C4 in the figure). It is possible to evaluate aged deterioration of the evaluating material by plotting pseudo hysteresis losses $W_F^*$ at different applied stresses $\sigma$ and comparing the two kinds of plots. Specifically, with regard to the curve obtained from data at the lower pseudo coercive force Hc* (dashed line C3 of FIG. 14), the pseudo hysteresis loss $W_F^*$ changes markedly in the range where the applied stress $\sigma$ is low, suggesting the material is very sensitive to plastic deformation at its initial stage of deformation. In contrast, with regard to the curve obtained from data at the higher coercive force Hc (dashed line C4 of FIG. 14), the pseudo hysteresis loss $W_F^*$ changes considerably in the range where the applied stress $\sigma$ is high, suggesting the material is sensitive to plastic deformation at the advanced stage of its deformation. This observation also applies to the curves of FIG. 15.

Figure 16:
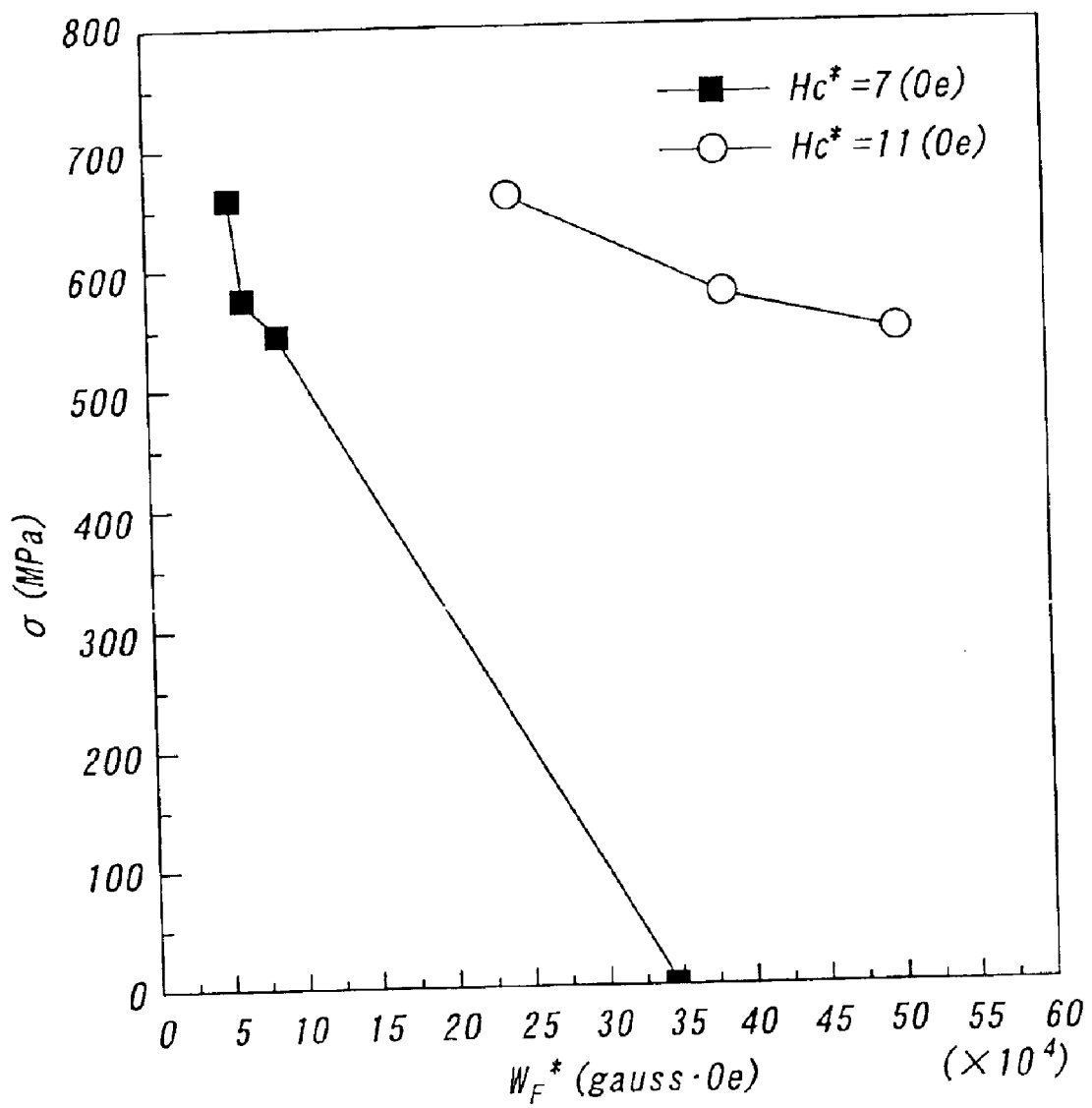
FIG. 16 is a graph exemplifying the relations (seventh relation) between applied stresses $\sigma$ and pseudo hysteresis losses $W_F^*$ at the pseudo coercive force $Hc^*=7$ and 11 Oe obtained from minor hysteresis loops of low-alloy steel A533B samples.

FIG. 16 shows the relation (seventh relation) between pseudo hysteresis loss $W_F^*$ and the applied stress $\sigma$ (MPa) at the point where the pseudo coercive force Hc*=7 Oe (dashed line C3 of FIG. 14) and 11 Oe (dashed line C4 of FIG. 14). In FIG. 16, the results obtained at the point where the pseudo coercive force Hc*=7 Oe are plotted by solid squares while the corresponding results at the point where the pseudo coercive force Hc*=11 Oe plotted by open circles.

Figure 17:
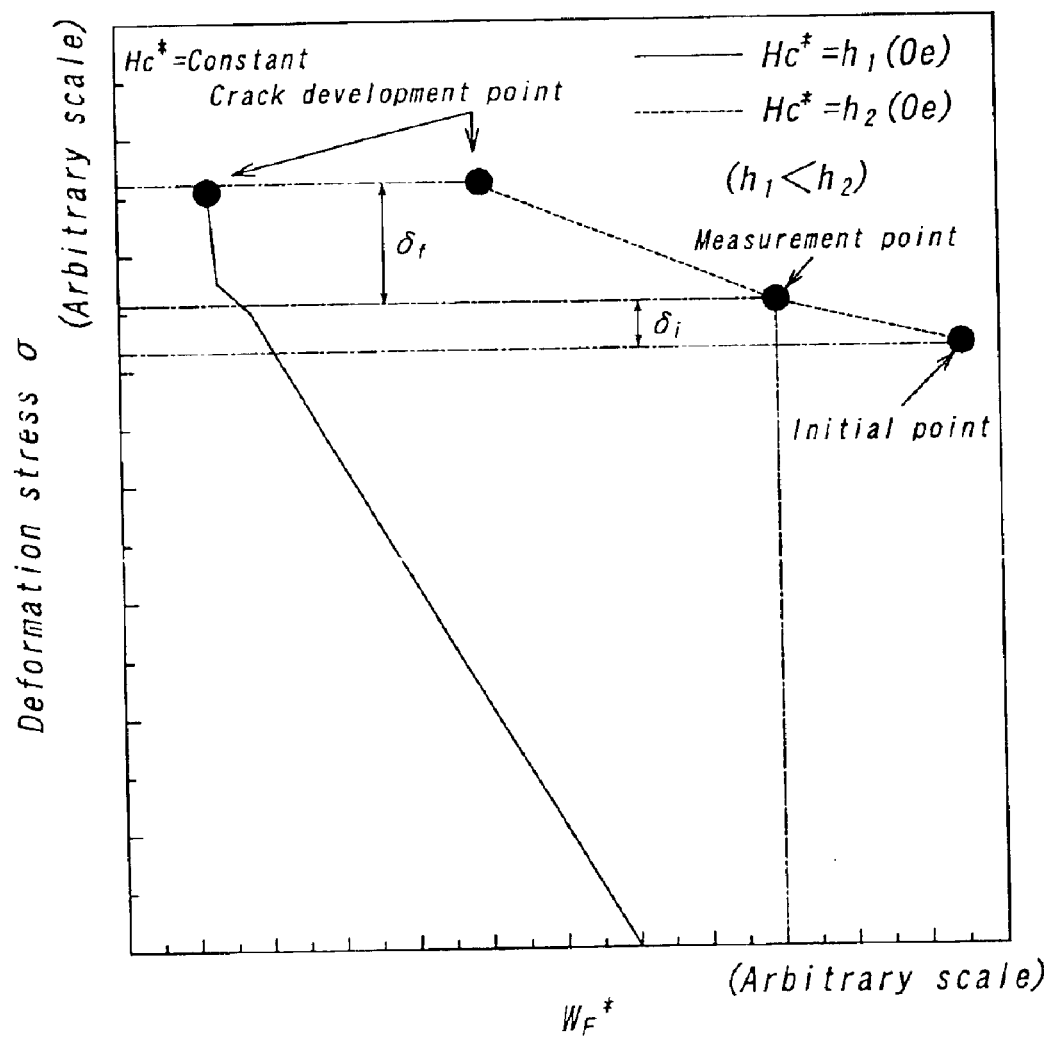
FIG. 17 is a graph for explaining the relation (seventh relation) between the applied stress $\sigma$ (MPa) and the pseudo hysteresis loss $W_F^*$ at the point where the pseudo coercive force $Hc^*$ takes a predetermined value (pseudo coercive force $Hc^*$ is constant), and how to evaluate aged deterioration and expected life of the evaluating material based on the graph.

Using the graphs shown in FIG. 16, similar graphs (pilot data from a magnetization test for obtaining minor hysteresis loops) shown in FIG. 17 relating the applied stress with the pseudo hysteresis loss $W_F^*$ are depicted with initial points and crack development points placed thereon. It is possible to predict aged deterioration and expected life of an evaluating material by evaluating distances $\delta_i$ (the extent of the aged deterioration) and $\delta_f$ (the expected life) based on the graph of FIG. 17, respectively. According to the graphs shown here, the extent of aged deterioration (distance $\delta_i$) of an evaluating material will be more sensitively determined by resorting to the curve obtained in the range where the pseudo coercive force Hc* is the lower (in FIG. 17, curve obtained at pseudo coercive force Hc*=$h_1$ (Oe)) at an initial stage of aged deterioration of the evaluating material. Also, at an advanced stage of aged deterioration of the evaluating material, the expected life (distance $\delta_f$) of an evaluating material will be more sensitively determined by resorting to the curve obtained in the range where the pseudo coercive force Hc* is the higher (in FIG. 17, curve obtained at pseudo coercive force Hc*=$h_2$ (Oe)).

In view of this, the evaluation information acquiring step comprises performing a minor hysteresis loop measurement on a test piece which is made of the same evaluating ferromagnetic construction material (evaluating material) for obtaining minor hysteresis loops (reference minor loops), and deriving the first and fifth relations (see FIGS. 4 and 11 respectively) from the reference minor loops. The measurement step comprises performing a minor hysteresis loop measurement on the evaluating material for obtaining subject minor hysteresis loops, and deriving pseudo hysteresis losses $W_F^*$ under the pseudo coercive force Hc* taking a predetermined value from the subject minor hysteresis loops. The evaluation step comprises evaluating aged deterioration and the dislocation density of the evaluating material from the first and fifth relations. The method allows one to reliably evaluate aged deterioration of an evaluating material using data obtained from a magnetization test where only comparatively low field intensities are used.

Generally, as the metal aged deterioration advances, the dislocation density increases. Domain walls become reluctant to move with increase of the dislocation density. The pseudo coercive force Hc* is the magnetic field intensity H obtained at the point where the pseudo susceptibility $\chi_H^*$ at pseudo coercive force Hc* becomes maximum. The pseudo hysteresis loss $W_F^*$ represents the amount of energy converted into heat occurring in association with the irreversible movements of domain walls, that is, a quantity representing the extent of dislocations which hinder the movements of domain walls. Thus, it is possible to obtain an overview of the potential energy of domain wall movements by evaluating aged deterioration of an evaluating material based on the relation between pseudo coercive force Hc* and pseudo hysteresis loss $W_F^*$.

According to the evaluating method of the present invention, the evaluation information acquiring step comprises obtaining the first relation (e.g., graph of FIG. 4) of the relation between pseudo coercive force Hc* and magnetic field amplitude $H_a$, and the fifth relation (e.g., graphs of FIG. 11) of the relation between pseudo hysteresis loss $W_F^*$ and magnetic field amplitude $H_a$. As it is possible to obtain the magnitude of forces imposed on domain walls, and their distribution based on the data obtained via the evaluation information acquiring step, it is possible to distinguish various lattice defects of the material responsible for its aged deterioration, and to separately quantify involved individual defects.

Thus, it is possible to specify individual lattice defects responsible for the aged deterioration of an evaluating ferromagnetic material used for constructing a reactor pressure vessel and to separately quantify the involvement of individual factors, by evaluating the pseudo coercive force Hc* and pseudo hysteresis loss $W_F^*$ together with the first and fifth relations and using those data for evaluating aged deterioration of the evaluating material. It is possible according to the evaluating method of the present invention to evaluate aged deterioration of an evaluating material more minutely, precisely and comprehensively than it is possible with conventional methods.

According to the evaluating method of the present invention, the evaluation information acquiring step may comprise obtaining the sixth relation of the relation between pseudo hysteresis loss $W_F^*$ and pseudo coercive force Hc* (for example, graphs of FIGS. 14 and 15) from the first and fifth relations as described above, and the evaluation step may comprise evaluating aged deterioration of an evaluating material from the sixth relation. According to this method, it is possible to more precisely and easily evaluate aged deterioration of the evaluating material based on the graphs as represented, for example, in FIGS. 12 to 15 than it is possible with conventional methods.

According to the evaluating method of the present invention, the evaluation information acquiring step may comprise obtaining the seventh relation of the relation between applied stress σ and pseudo hysteresis loss $W_F^*$ at a predetermined value of pseudo coercive force Hc* from the first and fifth relations or from the six relation as described above, and the evaluation step may comprise evaluating aged deterioration of an evaluating material from the seventh relation.

Then, it is possible, as seen from the graphs shown in FIG. 15, to quantitatively determine the values of deformation stress between a state prior to aged deterioration and a state at initiation of cracks, by obtaining the pseudo remanence work $W_R^*$ of the evaluating material, and plotting the results as shown in FIG. 17. Accordingly, it is possible to more precisely predict the extent of aged deterioration and expected life of the evaluating material than it is possible with conventional methods. The aforementioned evaluation information acquiring step provides information of change of the dislocation density according to values of the deformation stress.

The graphs of FIG. 11 show that the pseudo hysteresis loss $W_F^*$ decreases with the increase of applied stresses σ at the points where maximum value of magnetic field amplitude $H_a$ exceeds 40 Oe. This may be ascribed to a following reason: In the range where maximum value of magnetic field amplitude $H_a$ becomes 40 Oe or lower, the dislocation density increases and the potential energy hindering the movements of domain walls increases, the extent of domain wall movements becomes restricted, and thus the loss of energy is limited. On the other hand, from the curves of FIG. 11, it is obvious that the pseudo hysteresis loss $W_F^*$ increases with the increase of applied stresses σ at the points where maximum value of magnetic field amplitude $H_a$ becomes 40 Oe or higher. This may be ascribed to a following reason: In the range where maximum value of magnetic field amplitude $H_a$ becomes 40 Oe or higher, the extent of domain wall movements is extended, barriers hindering the domain wall movements increase, and thus energy loss is enhanced.

According to the evaluating method of the present invention, the evaluation information acquiring step may comprise obtaining the first relation of the relation between the pseudo coercive force Hc* and magnetic field amplitude $H_a$, the pseudo coercive force Hc* being the magnetic field intensity H at the point where the magnetic flux density B is zero, the eighth relation of the relation between the pseudo residual flux density Br* and magnetic field amplitude $H_a$, the pseudo residual flux density Br* being the magnetic flux density B at the point where the magnetic field intensity H is zero, and the ninth relation of the relation between the reciprocal $1/\chi_R^*$ of pseudo remanence susceptibility $\chi_R^*$ and magnetic field amplitude $H_a$, the pseudo remanence susceptibility $\chi_R^*$ being the gradient of a reference minor hysteresis loop at the pseudo remanence Br*, and the measurement step may comprise measuring the pseudo coercive force Hc* being magnetic field intensity H at the point where the magnetic flux density B is zero, pseudo remanence Br* being the magnetic flux density B at the point where the magnetic field intensity H is zero, and the reciprocal $1/\chi_R^*$ of pseudo remanence susceptibility $\chi_R^*$ being the gradient of a subject minor hysteresis loop at the pseudo remanence Br*.

Figure 18:
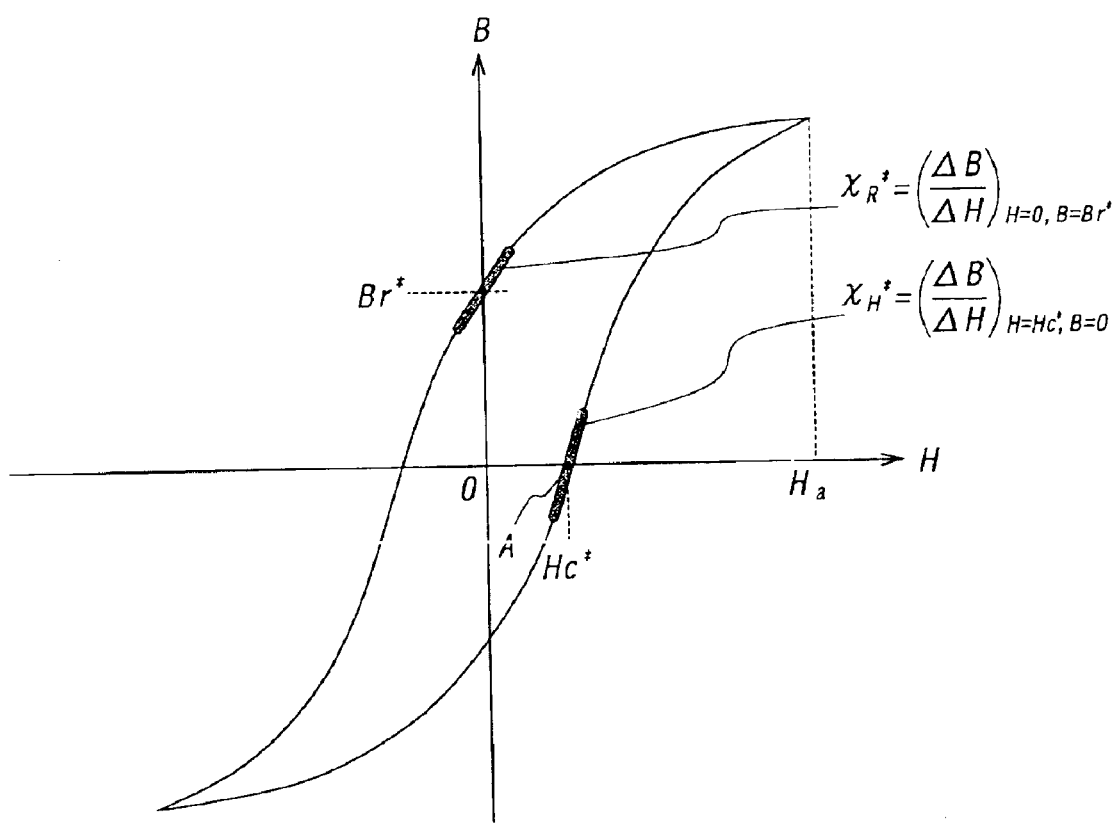
FIG. 18 is a minor hysteresis loop exemplifying how the pseudo remanence $Br^*$ and pseudo remanence susceptibility $\chi_R^*$.

In this specification, to distinguish, from the pseudo remanence (residual magnetization) and susceptibility obtained from a conventional hysteresis loop, corresponding physical quantities of the present invention, a magnetic flux density B obtained from a minor hysteresis loop at the point where the magnetic field intensity H is zero is called pseudo remanence Br*, susceptibility obtained from the minor hysteresis loop at the pseudo remanence Br*, that is, the gradient of the loop at the pseudo remanence Br* is called pseudo remanence susceptibility $\chi_R^*$ (=($\Delta B/\Delta H$) H=0, B=Br*) as shown in FIG. 18. The pseudo coercive force Hc*, pseudo remanence Br*, and pseudo remanence susceptibility $\chi_R^*$ are expressed as a function of magnetic field amplitude $H_a$, and, when magnetic field amplitude $H_a$ is sufficiently high, they correspond to the coercive force, pseudo remanence, and residual susceptibility (susceptibility at the pseudo remanence) obtained from a conventional hysteresis loop (major hysteresis loop).

Similarly to the foregoing methods, the evaluating method of the present invention comprises choosing appropriate stresses depending on a preliminary tensile test, applying the stresses to an evaluating material to deform the material, after removing the stress exposing the deformed material to a magnetic field whose maximum value of magnetic field amplitude is varied in a stepwise manner, to obtain a series of minor hysteresis loops. The method further comprises obtaining, from the minor hysteresis loops, the pseudo remanence Br*, pseudo remanence susceptibility $\chi_R^*$ and its reciprocal $1/\chi_R^*$, plotting those data into graphs, and evaluating the first relation of the relation between pseudo coercive force Hc* and magnetic field amplitude $H_a$ (as represented by the graphs of FIG. 4), the eighth relation of the relation between the pseudo remanence Br* and magnetic field amplitude $H_a$, and the ninth relation of the relation between the reciprocal $1/\chi_R^*$ of pseudo remanence susceptibility $\chi_R^*$ and magnetic field amplitude $H_a$, the pseudo remanence susceptibility $\chi_R^*$ being the gradient of a reference minor loop at the pseudo remanence Br*.

Effects and advantages obtained from the evaluating method as described above will be described below with reference to minor hysteresis loop data obtained from a test sample made of low-alloy steel A533B.

Figure 19:
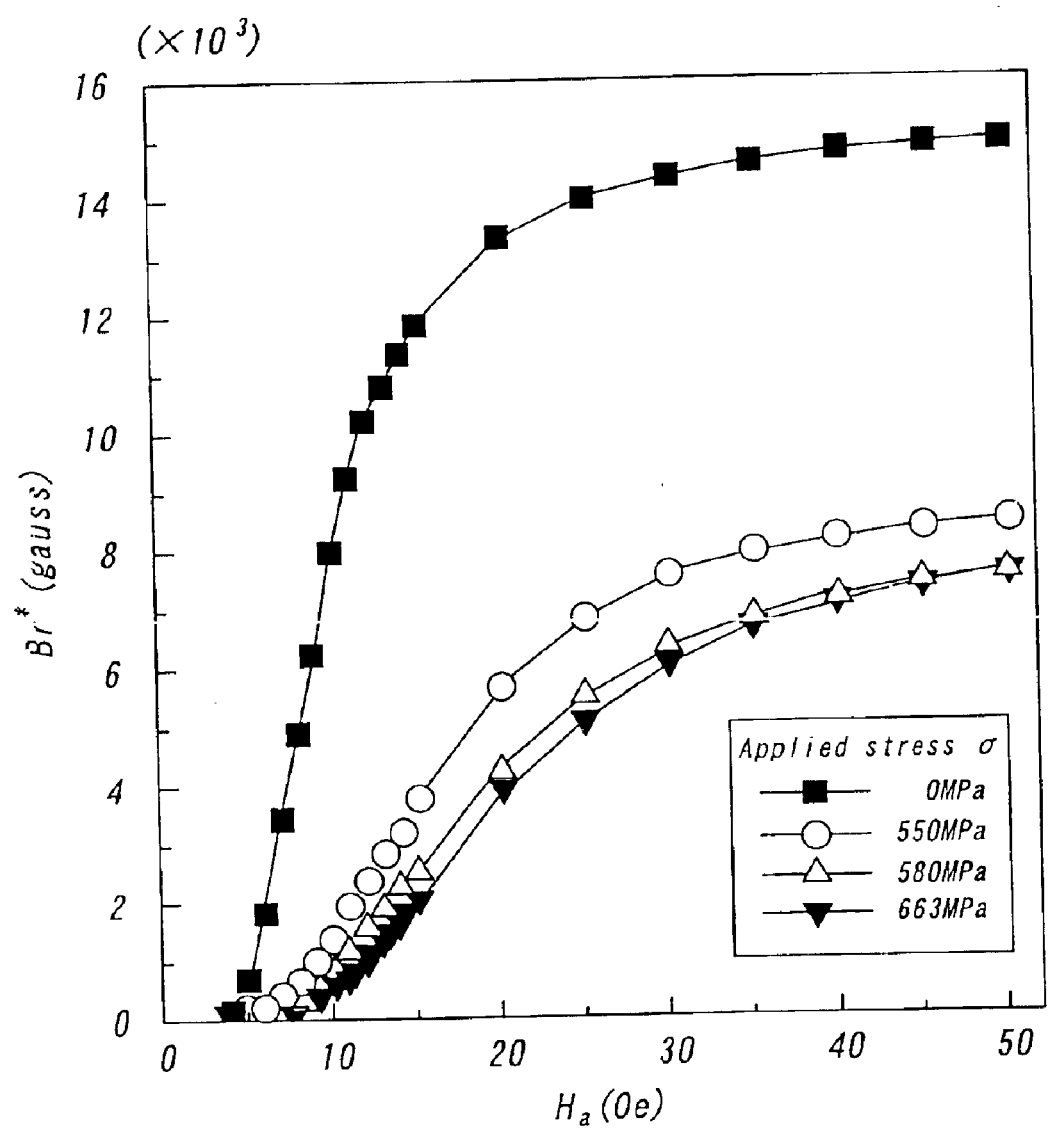
FIG. 19 is graphs exemplifying the dependence of the relation (eighth relation) between pseudo remanence $Br^*$ and magnetic field amplitude $H_a$ on stresses concomitantly applied, obtained from minor hysteresis loops of low-alloy steel A533B samples.
Figure 20:
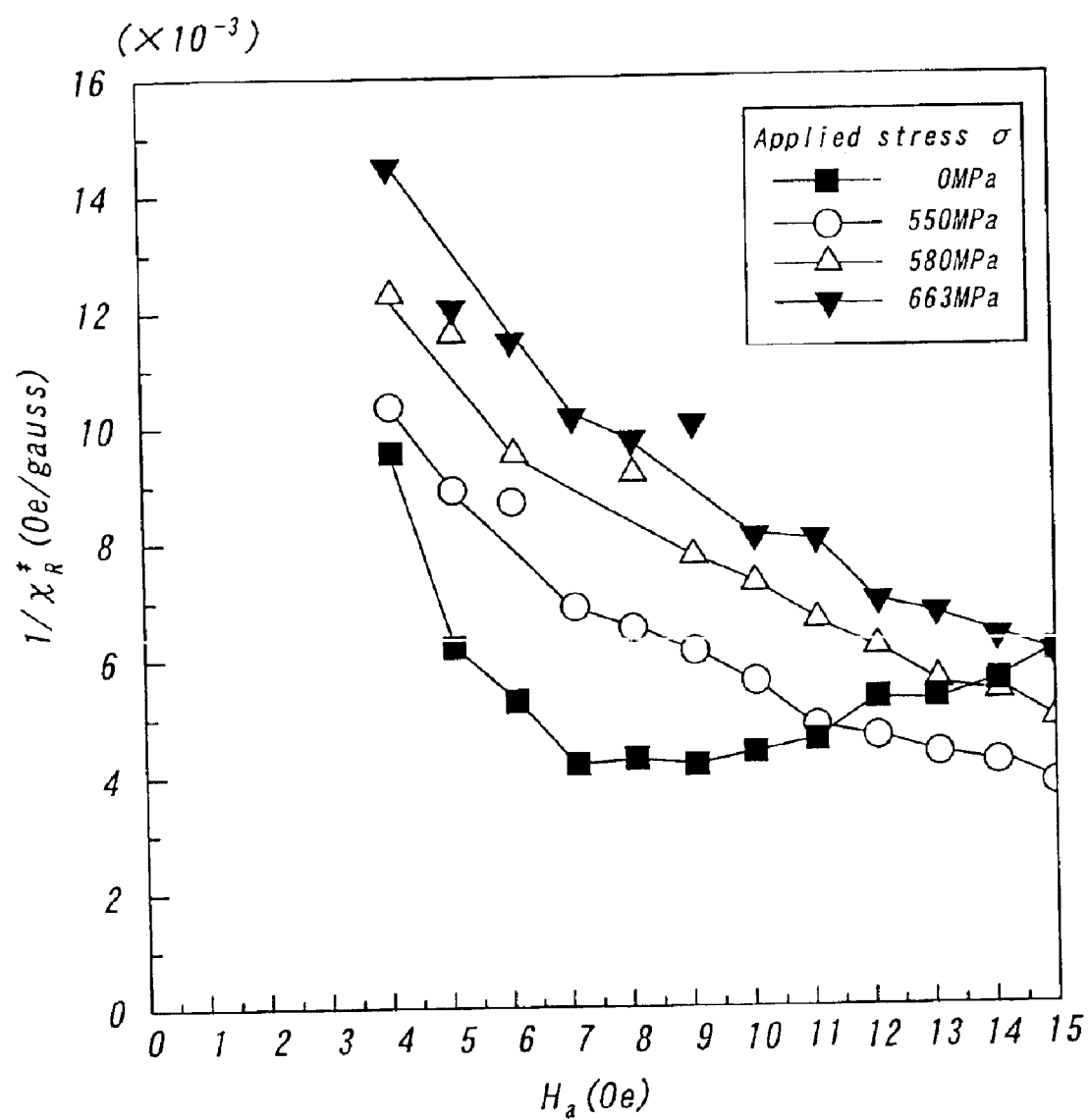
FIG. 20 is graphs exemplifying the dependence of the relation (ninth relation) between the reciprocal $1/\chi_R^*$ of pseudo remanence susceptibility $\chi_R^*$ and magnetic field amplitude $H_a$ on stresses concomitantly applied, obtained from minor hysteresis loops of low-alloy steel A533B samples.

The first relation (as represented by the graphs of FIG. 4) of the relation between the pseudo coercive force Hc* and magnetic field amplitude $H_a$, and the eighth relation of the relation between pseudo remanence Br* and magnetic field amplitude $H_a$ are obtained from minor hysteresis loop data. FIG. 4 shows the dependence of the relation between pseudo coercive force Hc* and magnetic field amplitude $H_a$ (first relation) on applied stresses. FIG. 19 shows the dependence of the relation (eighth relation) between pseudo remanence Br* and magnetic field amplitude $H_a$ on applied stresses. FIG. 20 shows the dependence of the relation (ninth relation) between the reciprocal $1/\chi_R^*$ of pseudo remanence susceptibility $\chi_R^*$ and magnetic field amplitude $H_a$ on applied stresses. Stresses chosen for the graphs of FIGS. 19 and 20 include, based on the results of a preliminary tensile test, the applied stress σ=0 (MPa) and stress at the threshold of breaking point (σ=663 MPa), and intermediate values between the two extreme values, i.e., σ=550, 580 MPa. The results obtained at the points where the applied stresses σ=0, 550, 580 and 663 MPa are plotted by solid squares, open circles, open triangles, and solid triangles respectively in FIGS. 19 and 20.

Figure 21:
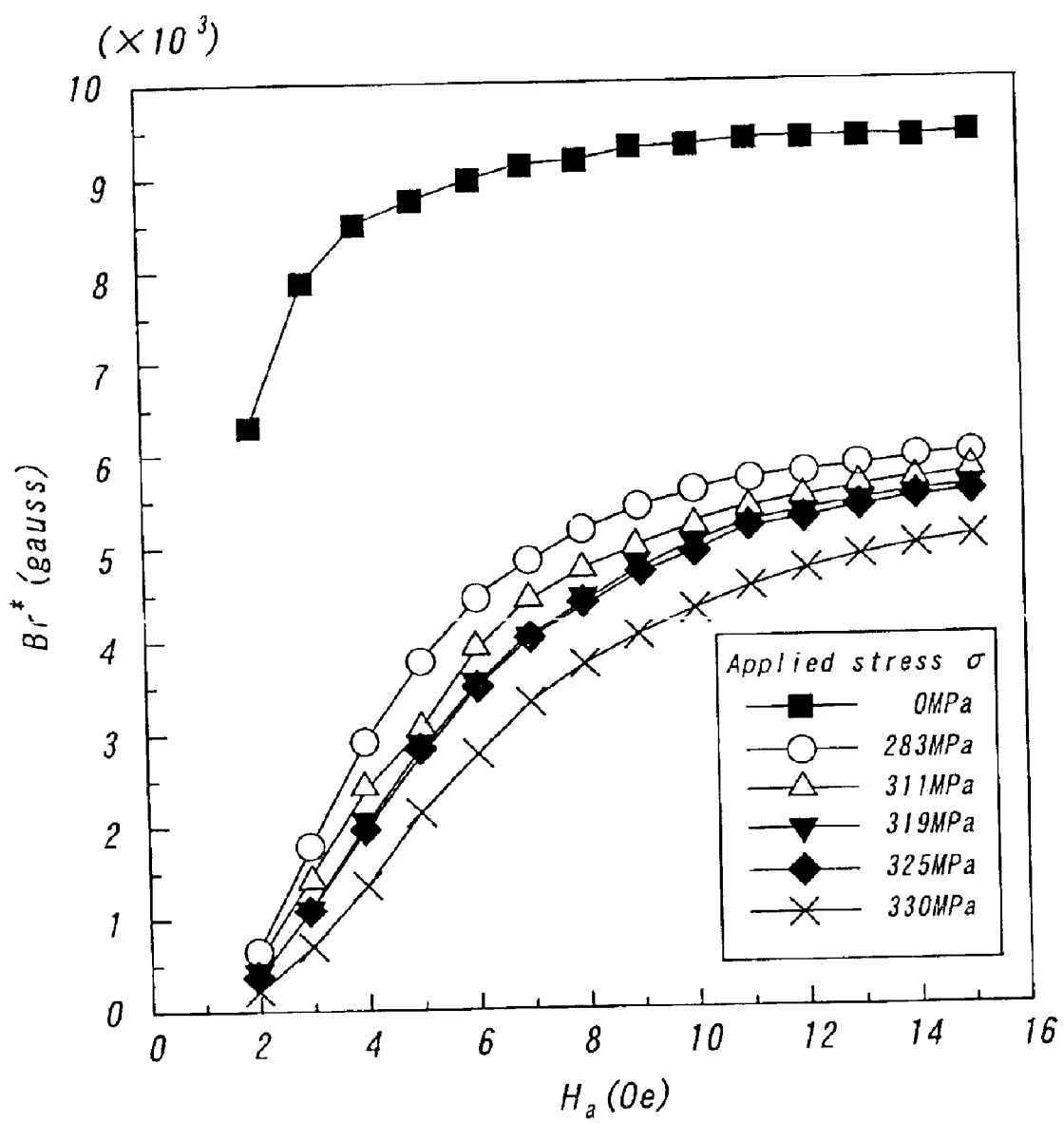
FIG. 21 is graphs exemplifying the dependence of the relation (eighth relation) between pseudo remanence $Br^*$ and magnetic field amplitude $H_a$ on stresses concomitantly applied, obtained from minor hysteresis loops of polycrystalline pure iron samples (average grain diameter of 37 $\mu$m)
Figure 22:
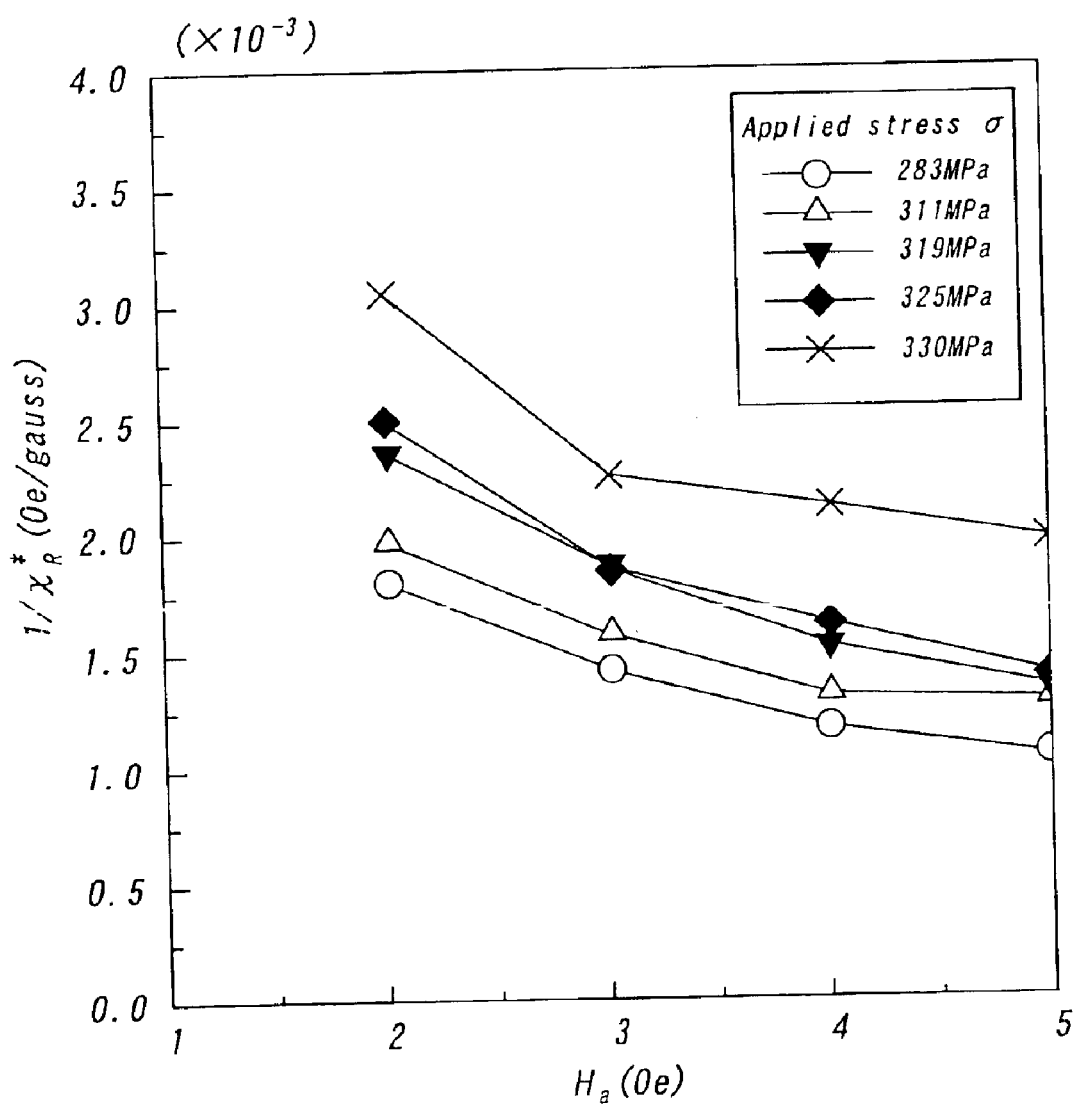
FIG. 22 is graphs exemplifying the dependence of the relation (ninth relation) between the reciprocal $1/\chi_R^*$ of pseudo remanence susceptibility $\chi_R^*$ and magnetic field amplitude $H_a$ on stresses concomitantly applied, obtained from minor hysteresis loops of polycrystalline pure iron samples (average grain diameter of 37 $\mu$m)

FIGS. 21 and 22 show the dependence of the relation between pseudo remanence Br* and magnetic field amplitude $H_a$ (eighth relation) and relation between the reciprocal $1/\chi_R^*$ of pseudo remanence susceptibility $\chi_R^*$ and magnetic field amplitude $H_a$ (ninth relation) on applied stresses, respectively, both relations obtained from a minor hysteresis loop measurement performed on an evaluating material of poly-crystalline pure iron (average grain diameter of 37 μm). The relation between pseudo coercive force Hc* and magnetic field amplitude $H_a$ (first relation) is the same as that observed in the graphs of FIG. 12. The applied stress σ used for the production of graphs of FIGS. 21 and 22 fell in the range between 0 and 283 to 330 MPa based on the results of a preliminary tensile test. In FIG. 21, the results obtained at the points where the applied stresses σ=0, 283, 311, 319, 325 and 330 MPa are plotted by solid squares, open circles, open triangles, solid triangles, solid diamonds, and crosses, respectively.

The minor hysteresis loops responsible for the production of graphs of FIG. 19 were obtained at the point where maximum value of magnetic field amplitude $H_a$ was varied from 0 to 50 Oe. However, according to the evaluating method of the present invention, to obtain information sufficiently reliable to evaluate aged deterioration of an evaluating material, it is only necessary to vary maximum value of magnetic field amplitude at most up to 20 Oe. The reason for this will be described later. In this example, the stepwise increment of maximum value of magnetic field amplitude $H_a$ was chosen to be 1 Oe, but needless to say, a finer stepwise increment will bring more detailed information.

Figure 23:
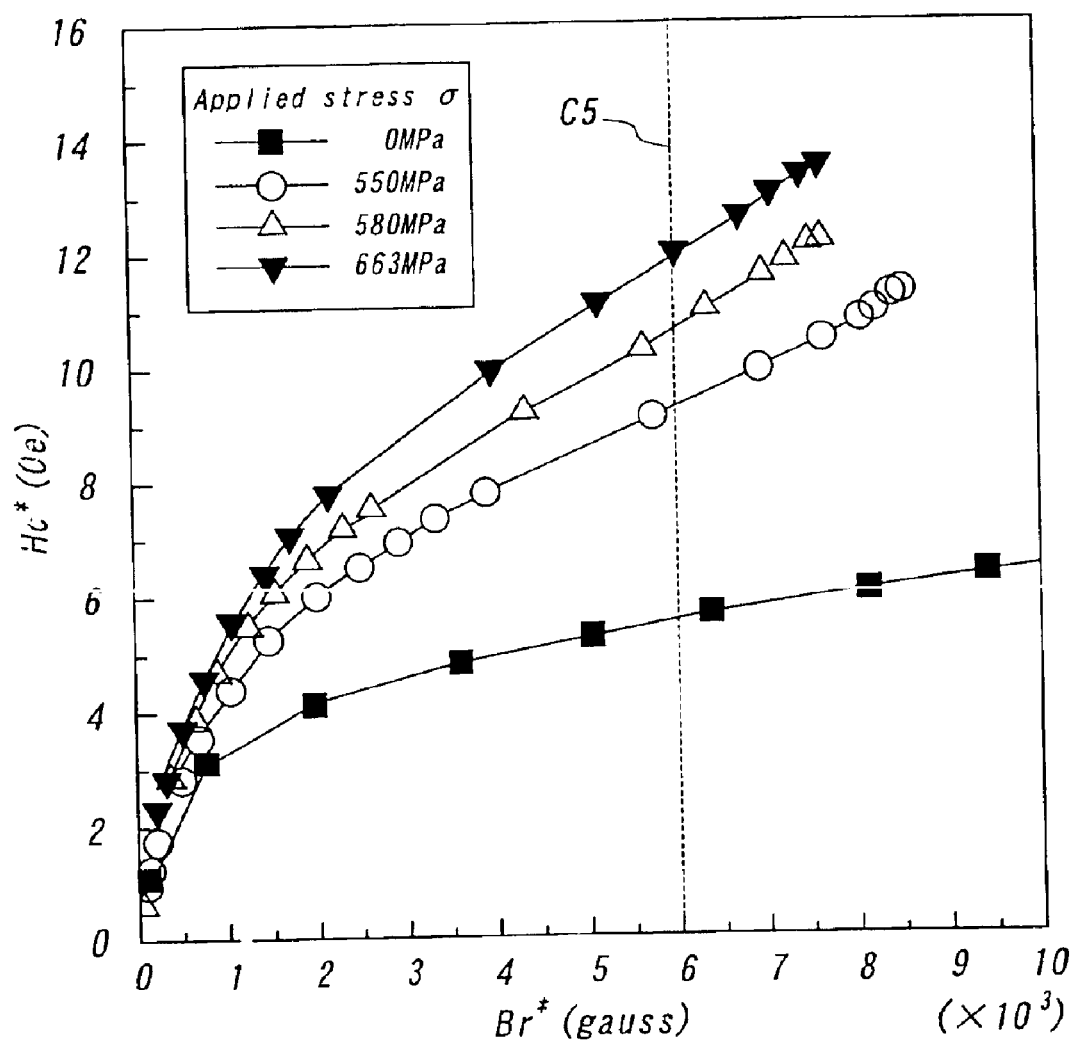
FIG. 23 is graphs exemplifying the dependence of the relation (tenth relation) between the pseudo coercive force $Hc^*$ and the pseudo remanence $Br^*$ obtained from minor hysteresis loops of low-alloy steel A533B samples.
Figure 24:
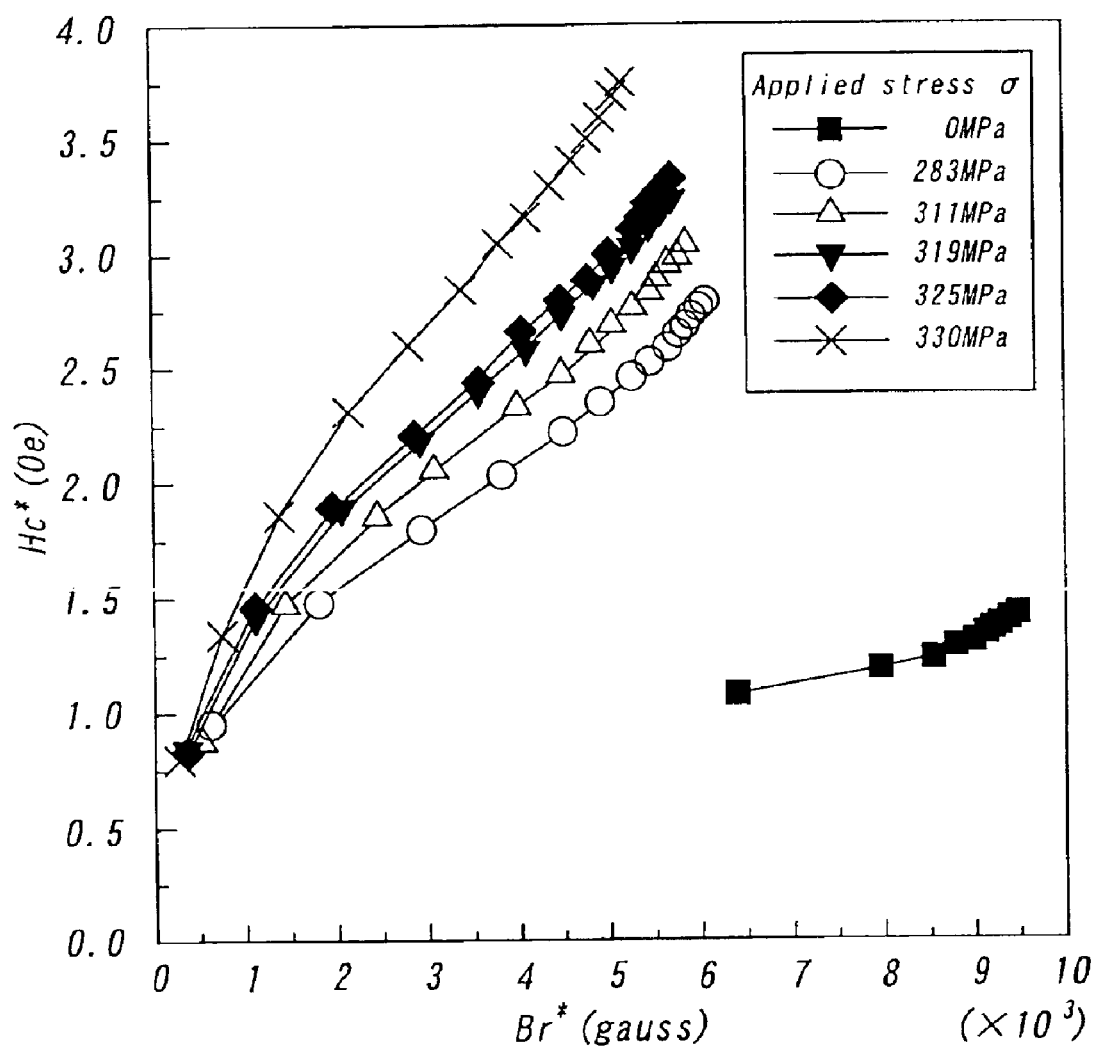
FIG. 24 is graphs exemplifying the dependence of the relation (tenth relation) between the pseudo coercive force $Hc^*$ and the pseudo remanence $Br^*$ obtained from minor hysteresis loops of polycrystalline pure iron samples (average grain diameter of 37 $\mu$m)

FIG. 23 illustrates the relation (tenth relation) between pseudo coercive force Hc* and pseudo remanence Br* derived from the relation (first relation) between pseudo coercive force Hc* and magnetic field amplitude $H_a$ as shown in FIG. 4 and the relation (eighth relation) between pseudo remanence Br* and pseudo coercive force Hc* as shown in FIG. 19, obtained from an evaluating material of low-alloy steel A533B. FIG. 24 illustrates the relation (tenth relation) between pseudo coercive force Hc* and pseudo remanence Br* obtained from an evaluating material of polycrystalline pure iron.

It is obvious from FIGS. 23 and 24 that the relation between pseudo coercive force Hc* and pseudo remanence Br* increases with the increase of applied stresses σ. In FIG. 23, the results obtained at the points where applied stresses σ=0, 550, 580 and 663 MPa are plotted by solid squares, open circles, open triangles, and solid triangles, respectively. In FIG. 24, the results obtained at the points where the applied stresses σ=0, 283, 311, 319, 325, and 330 MPa are plotted by solid squares, open circles, open triangles, solid triangles, solid diamonds, and crosses, respectively. The curves plotted by solid triangles in FIG. 23 obtained under an applied stress σ=663 MPa and the curves plotted by crosses in FIG. 24 obtained under an applied stress σ=330 MPa are derived from an evaluating material just at the threshold of breakage.

Based on this observation, the Inventor demonstrated that deformation stresses (may be replaced with internal stresses) have an intimate correlation with the relation between pseudo remanence Br* and pseudo coercive force Hc*. Moreover, because the relation between pseudo remanence Br* and pseudo coercive force Hc* varies depending on the type of evaluating materials, it is possible to identify a given evaluating material by evaluating the relation in question for that material.

Figure 25:
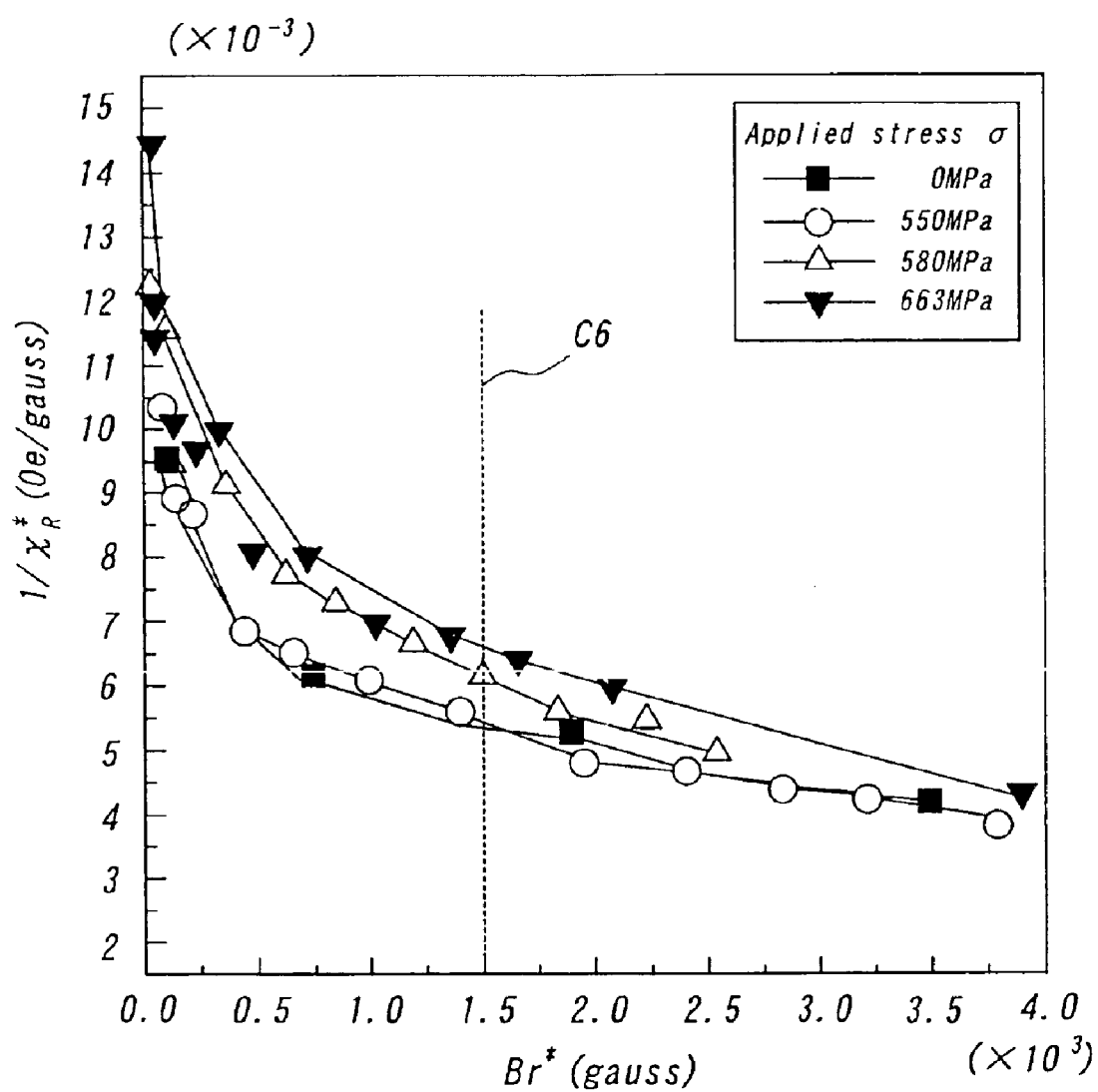
FIG. 25 is graphs exemplifying the dependence of the relation (eleventh relation) between the reciprocal $1/\chi_R^*$ of pseudo remanence susceptibility $\chi_R^*$ and the pseudo remanence $Br^*$ obtained from minor hysteresis loops of low-alloy steel A533B samples.
Figure 26:
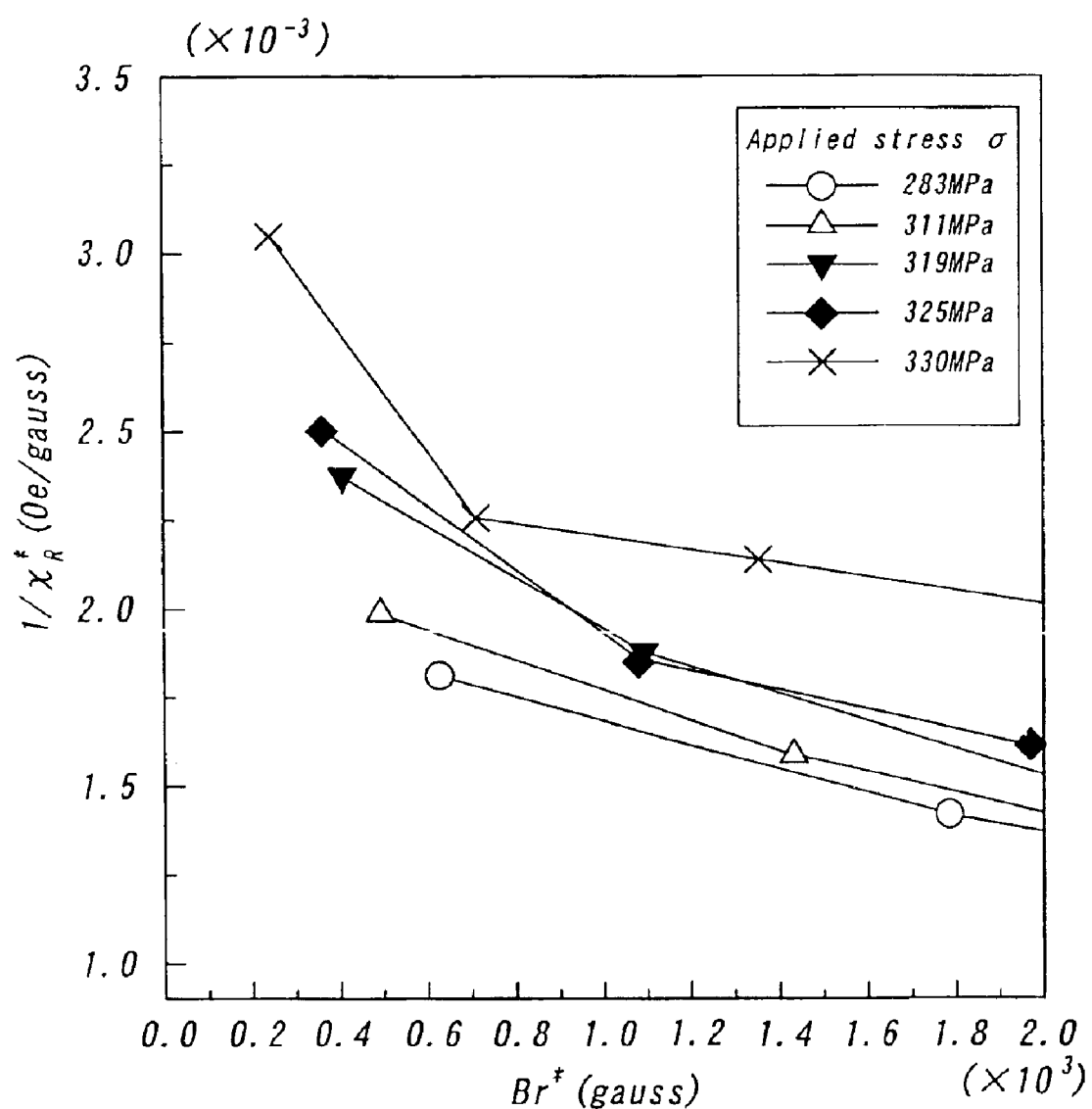
FIG. 26 is graphs exemplifying the dependence of the relation (eleventh relation) between the reciprocal $1/\chi_R^*$ of pseudo remanence susceptibility $\chi_R^*$ and the pseudo remanence $Br^*$ obtained from minor hysteresis loops of polycrystalline pure iron samples (average grain diameter of 37 $\mu$m)

FIG. 25 illustrates the relation (twelfth relation) between the reciprocal of pseudo remanence susceptibility $1/\chi_R^*$ and pseudo remanence Br* derived from the relations shown in FIGS. 19 and 20, obtained from an evaluating material of low-alloy steel A533B. FIG. 26 illustrates the relation (twelfth relation) between the reciprocal $1/\chi_R^*$ of pseudo remanence susceptibility $\chi_R^*$ and pseudo remanence Br* obtained from an evaluating material of polycrystalline pure iron.

It is obvious from FIGS. 25 and 26 that the relation (twelfth relation) between the reciprocal $1/\chi_R^*$ of pseudo remanence susceptibility $\chi_R^*$ and pseudo remanence $Br^*$ changes separately with the increase of applied stresses σ. In FIG. 25, the results obtained at the points where the applied stresses σ=0, 550, 580 and 663 MPa are plotted by solid squares, open circles, open triangles, and solid triangles, respectively. In FIG. 25, the results obtained at the points where σ=0, 550, 580, and 663 MPa are plotted by solid squares, open circles, open triangles, and solid triangles, respectively. In FIG. 26, the results obtained at the points where the applied stresses σ=283, 311, 319, 325, and 330 MPa are plotted by solid squares, open circles, open triangles, solid triangles, solid diamonds, and crosses, respectively. The curve plotted by solid triangles in FIG. 25 obtained after an applied stress σ=663 MPa and the curve plotted by crosses in FIG. 26 obtained after an applied stress σ=330 MPa are derived from an evaluating material just at the threshold of breakage.

Based on this observation, the Inventor demonstrated that deformation stresses (may be replaced with internal stresses) have an intimate correlation with the relation between the reciprocal $1/\chi_R^*$ of pseudo remanence susceptibility $\chi_R^*$ and pseudo remanence $Br^*$. Moreover, because the relation between the reciprocal $1/\chi_R^*$ of pseudo remanence susceptibility $\chi_R^*$ and pseudo remanence $Br^*$ varies depending on the type of evaluating materials, it is possible to identify a given evaluating material by evaluating the relation in question for that material.

It is possible to follow the aged deterioration of an evaluating material and thus to evaluate aged deterioration of the material by comparing graphs at the range where the pseudo remanence $Br^*$ is comparatively low without resorting to graphs extending over a full range as shown FIG. 23. Namely, as for FIG. 23, it is possible to evaluate aged deterioration of an evaluating material by taking pseudo coercive forces $Hc^*$ of applied stresses σ corresponding to, for example, the pseudo remanence $Br^*$=6 gauss (dashed line C5 in the FIG. 23), and by comparing them.

Figure 27:
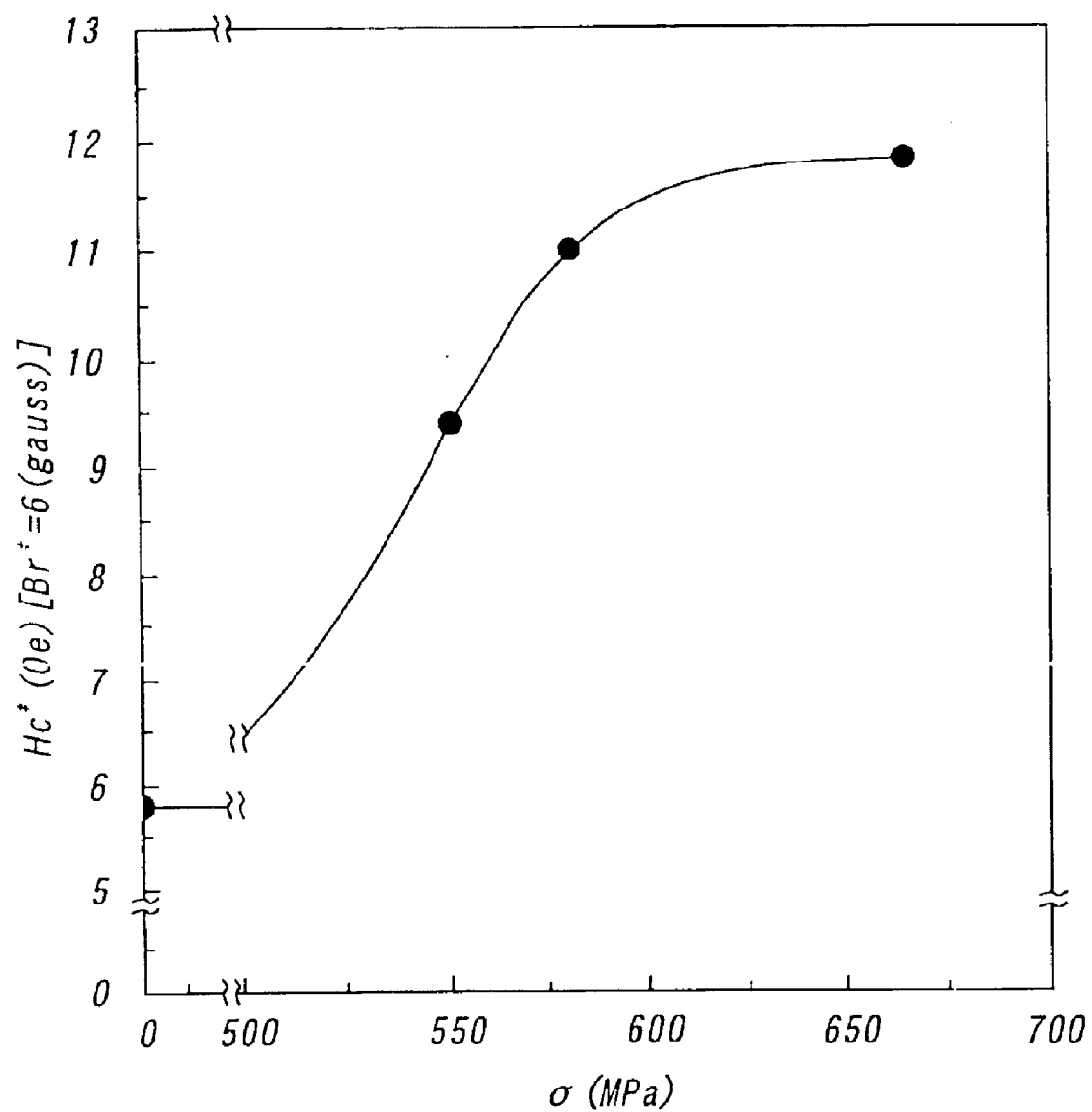
FIG. 27 is a graph exemplifying the relation between the pseudo coercive force $Hc^*$ and applied stresses $\sigma$ at the pseudo remanence $Br^*=6$ gauss, obtained from the curves shown in FIG. 23.

FIG. 27 illustrates the relation between the pseudo coercive force $Hc^*$ and applied stresses σ at the pseudo remanence $Br^*$=6 gauss, derived from the curves shown in FIG. 23. It is obvious from inspection of the graphs of the figure that the pseudo coercive force $Hc^*$ increases with the increase of applied stresses σ. Thus, it is possible to quantitatively evaluate aged deterioration of an evaluating material using the relation.

Moreover, according to the previous observation where reliable data can be obtained even under a magnetic field whose magnetic field amplitude is rather low, it is possible to evaluate the extent of aged deterioration of an evaluating material and to appreciate the dislocation density, by performing a minor hysteresis loop measurement on the evaluating material and obtaining a pseudo coercive force $Hc^*$ corresponding with a pseudo remanence $Br^*$ having a predetermined value from the graphs as shown in FIG. 27. Namely, it is possible to reliably evaluate aged deterioration of an evaluating material by resorting to information obtained from a minor hysteresis loop measurement where rather low magnetic field intensity is used.

Figure 28:
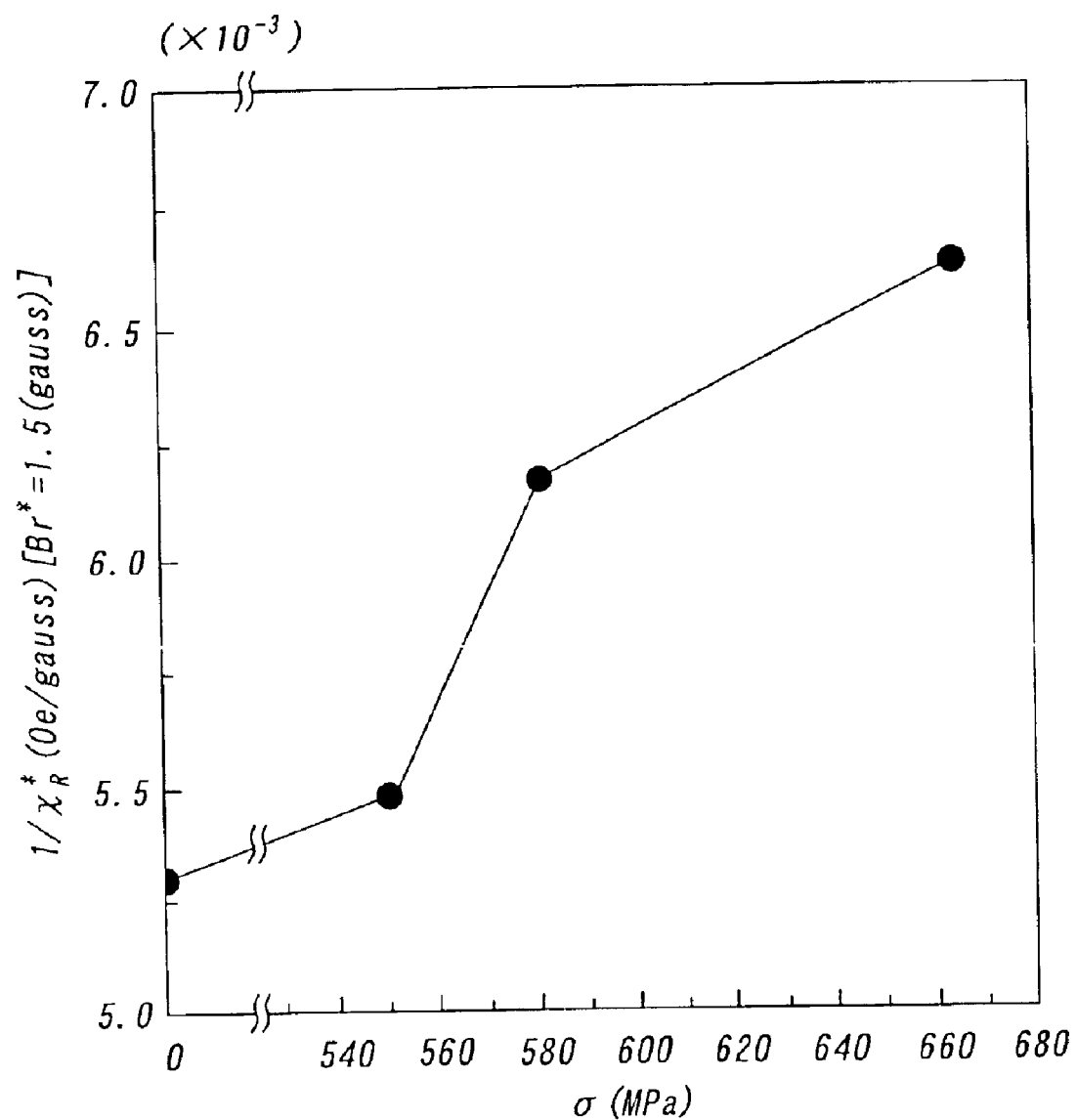
FIG. 28 is a graph exemplifying the relation between the reciprocal $1/\chi_R^*$ of pseudo remanence susceptibility $\chi_R^*$ and applied stresses $\sigma$ at the pseudo remanence $Br^*=1.5$ gauss, obtained from the curves shown in FIG. 25.

FIG. 28 illustrates the relation between the reciprocal $1/\chi_R^*$ of pseudo remanence susceptibility $\chi_R^*$ and applied stresses σ at the pseudo remanence $Br^*$=1.5 gauss, derived from the curves shown in FIG. 25 (dashed line C6 of FIG. 25). It is possible to quantitatively determine the values of deformation stress between a state prior to aged deterioration and a state at initiation of cracks, by evaluating the reciprocal $1/\chi_R^*$ of pseudo remanence susceptibility $\chi_R^*$ using the graphs of FIG. 28. Therefore, it is possible to more precisely predict aged deterioration of an evaluating material and its expected life than it is otherwise possible. It is also possible to predict the change of the dislocation density in a test sample by resorting to data of deformation stresses.

Generally, as the metal aged deterioration advances, the dislocation density increases. Domain walls become reluctant to move with increase of the dislocation density. The pseudo remanence $Br^*$ is the magnitude of magnetization which results from domain walls hindered in their movements at the range where the magnetic field intensity is returned from the maximum to zero. The reciprocal $1/\chi_R^*$ of pseudo remanence susceptibility $\chi_R^*$ corresponds to a resistance that domain walls receive in the presence of barriers. Thus, both the pseudo remanence $Br^*$ and the reciprocal of pseudo remanence susceptibility $1/\chi_R^*$ are quantities representative of lattice defects such as dislocations which act as a barrier against domain wall movement. Therefore it is possible to obtain an overall view of the potential energy of domain wall movement by changing magnetic field amplitude $H_a$.

According to the evaluating method of the present invention, it is possible to determine the magnitude of forces imposed on domain walls and their distribution, by using the relation (eighth relation) between pseudo remanence $Br^*$ and magnetic field amplitude $H_a$ (as shown in FIG. 19) and the relation (ninth relation) between the reciprocal $1/\chi_R^*$ of pseudo remanence susceptibility $\chi_R^*$ and magnetic field amplitude $H_a$ (as shown in FIG. 20) obtained via the evaluation information acquiring step. Therefore, it is possible to distinguish various lattice defects of the material responsible for its aged deterioration, and to separately quantify involved individual defects.

It is possible to discriminate individual lattice defects responsible for aged deterioration of ferromagnetic construction materials used for constructing the reactor pressure vessel, and to precisely quantify the involvement of individual factors by using the reciprocal $1/\chi_R^*$ of pseudo remanence susceptibility $\chi_R^*$, pseudo remanence $Br^*$, and the eighth to eleventh relations obtained via the evaluation information acquiring step. Thus, according to the evaluating method of the present invention it is possible to evaluate aged deterioration of an evaluating material more minutely, precisely and comprehensively than it is possible with conventional methods.

According to the evaluating method of the present invention, as the graphs of FIG. 23 are obtained from the graphs of FIGS. 4 and 19, the evaluation information acquiring step may comprise obtaining the tenth relation of the relation between pseudo remanence $Br^*$ and pseudo coercive force $Hc^*$ from the first to eighth relations, and the evaluation step may comprise evaluating aged deterioration of an evaluating material using the tenth relation. According to this evaluating method, it is possible to identify the type of evaluating material, because there is an intimate correlation between stresses and the relation between pseudo remanence $Br^*$ and pseudo coercive force $Hc^*$. It is possible using the tenth relation to evaluate aged deterioration of an evaluating material more minutely, precisely and comprehensively than it is possible with conventional methods.

According to the evaluating method of the present invention, as the graphs of FIG. 27 are obtained from the graphs of FIG. 23, the evaluation information acquiring step may comprise obtaining the eleventh relation of the relation between pseudo coercive force Hc* and applied stresses σ at the point where the pseudo remanence Br* takes a predetermined value, from the tenth relation, and the evaluation step may comprise evaluating texture deterioration of an evaluating material as a result of aged deterioration using the eleventh relation. According to this evaluating method, it is possible to evaluate aged deterioration of an evaluating material more precisely and easily than it is possible with conventional methods, based on graphs representing the eleventh relation as described later.

Figure 29:
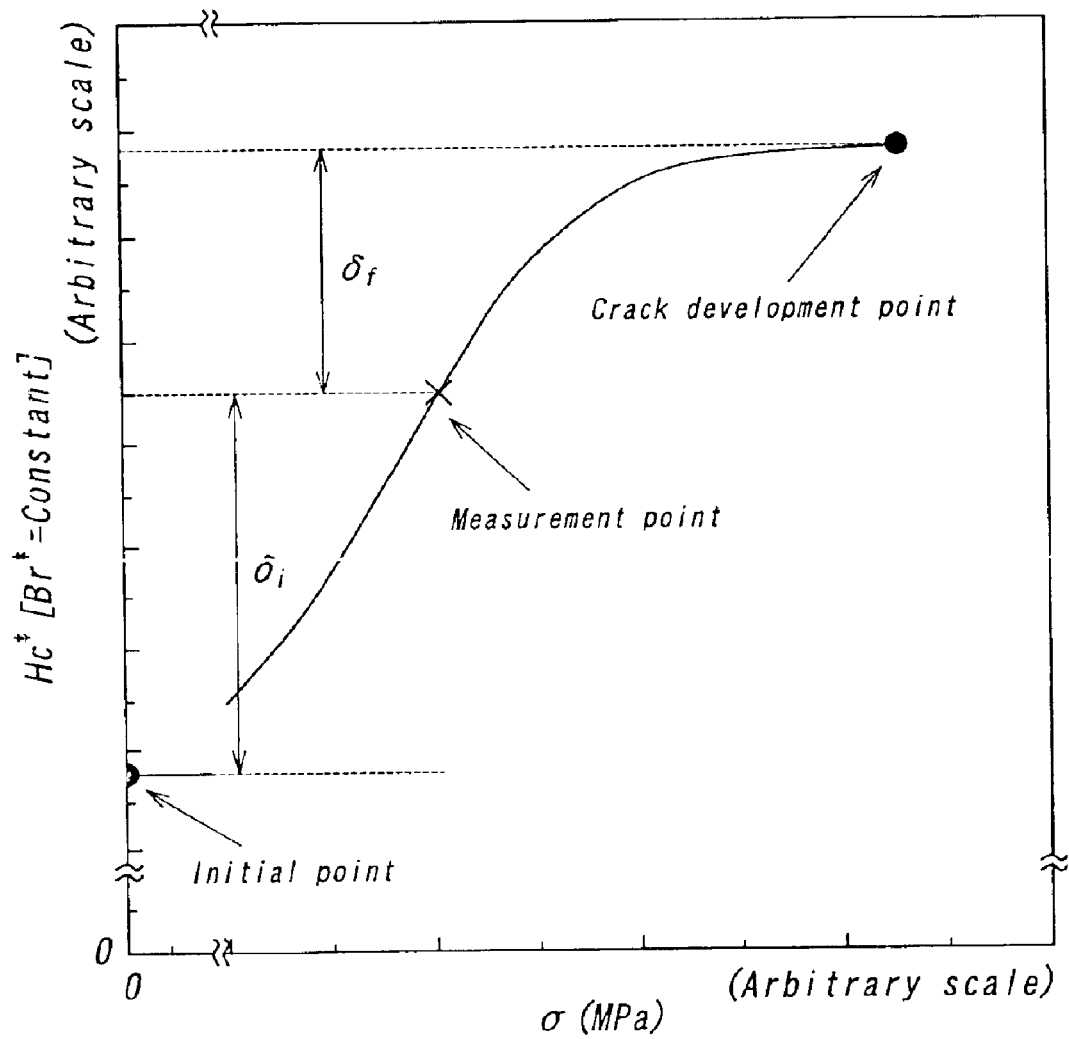
FIG. 29 is a conceptual graph showing the relation (eleventh relation) between the pseudo coercive force $Hc^*$ and applied stresses $\sigma$ at the point where the pseudo remanence $Br^*$ takes a predetermined value (pseudo remanence $Br^*$ is constant)

FIG. 29 is a conceptual graph (eleventh relation) relating the pseudo coercive force Hc* with applied stresses σ at the point where the pseudo remanence Br* takes a predetermined value. This conceptual graph represents the relation (e.g., as shown in FIG. 27) between pseudo coercive force Hc* and applied stresses σ at the point where the pseudo remanence Br* takes a predetermined value, with an initial point, a measurement point and an initiation point of crack plotted on the graph. As it is evident from the graph representing the eleventh relation shown in FIG. 29, it is possible to predict aged deterioration ($\delta_i$ in FIG. 29) of an evaluating material and its expected life ($\delta_f$ in FIG. 29) based on difference between the pseudo coercive force Hc* at the initial point and that at the measurement point, and on difference between the pseudo coercive force Hc* at the measurement point and that at the initiation point of crack. Thus, it is possible to easily evaluate aged deterioration of the material using $\delta_i$ and $\delta_f$ values.

According to the evaluating method of the present invention, as the graphs of FIG. 25 are obtained from the graphs of FIGS. 19 and 20, the evaluation information acquiring step may comprise obtaining the twelfth relation of the relation between pseudo remanence Br* and the reciprocal $1/\chi_R^*$ of pseudo remanence susceptibility $\chi_R^*$ from the eighth and ninth relations, the pseudo remanence Br* being the magnetic flux density B at the point where the magnetic field intensity H is zero, and pseudo remanence susceptibility $\chi_R^*$ being the gradient of a reference hysteresis loop at the pseudo remanence Br*, and the evaluation step may comprise evaluating texture deterioration of an evaluating material as a result of aged deterioration using the twelfth relation. According to this evaluating method, it is possible to evaluate aged deterioration of an evaluating material more precisely and easily than with conventional methods, based on graphs representing the twelfth relation like the ones shown in FIGS. 25 and 26.

According to the evaluating method of the present invention, as the graph of FIG. 28 are obtained from the graphs of FIG. 25, the evaluation information acquiring step may comprise obtaining the thirteenth relation of the relation between the reciprocal $1/\chi_R^*$ of pseudo remanence susceptibility $\chi_R^*$ and applied stresses σ from the eighth and ninth relations or from the twelfth relation, the pseudo remanence susceptibility $\chi_R^*$ being the gradient of a reference minor hysteresis loop at the pseudo remanence Br*, and the evaluation step may comprise evaluating texture deterioration of an evaluating material as a result of aged deterioration using the thirteenth relation. According to this evaluating method, it is possible as described above to evaluate aged deterioration of an evaluating material more precisely than with conventional methods, based on graphs representing the thirteenth relation like the ones shown in FIG. 28. Thus, it is possible to evaluate aged deterioration of an evaluating material more precisely and easily than with conventional methods.

According to the evaluating method of the present invention, the evaluation information acquiring step may comprise obtaining the first relation of the relation between the pseudo coercive force Hc* and magnetic field amplitude $H_a$, the pseudo coercive force Hc* being the magnetic field intensity H at the point where the magnetic flux density B is zero, and the fourteenth relation of the relation between pseudo remanence work $W_R^*$ and magnetic field amplitude $H_a$, the pseudo remanence work $W_R^*$ being a fraction of the area enclosed by a reference minor hysteresis loop, and the measurement step may comprise obtaining the pseudo coercive force Hc* which is the magnetic field intensity H at the point where the magnetic flux density B is zero, and pseudo remanence work $W_R^*$ obtained form a fraction of the area enclosed by a subject minor hysteresis loop.

According to this version of the evaluating method of the present invention, similarly to the foregoing methods, stresses appropriately chosen according to the results of a previous tensile test are applied to an evaluating ferromagnetic material; the stresses are removed and the deformed evaluating material is exposed to a magnetic field whose maximum value of magnetic field amplitude is varied in a stepwise manner to obtain thereby minor hysteresis loops.

Effects and advantages obtained from the evaluating method as described above will be described below with reference to minor hysteresis loop data obtained from a test sample made of low-alloy steel A533B.

Figure 30:
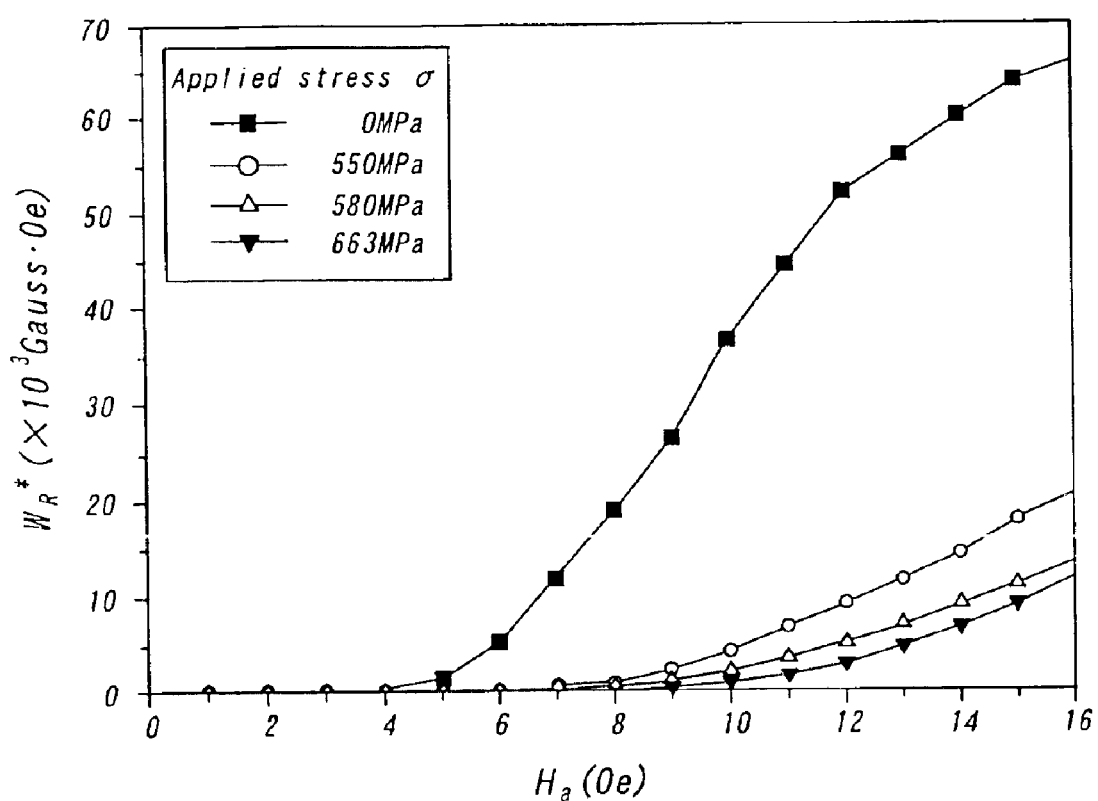
FIG. 30 is graphs exemplifying the dependence of the relation (fourteenth relation) between pseudo remanence work $W_R^*$ and magnetic field amplitude $H_a$ on stresses concomitantly applied.

The first relation (as represented by the graphs of FIG. 4) of the relation between the pseudo coercive force Hc* and magnetic field amplitude $H_a$ and the fourteenth relation of the relation between pseudo remanence work $W_R^*$ (see FIG. 10) and magnetic field amplitude $H_a$ are obtained from minor hysteresis loop data. FIG. 4 shows the dependence of the relation between pseudo coercive force Hc* and magnetic field amplitude $H_a$ (first relation) on applied stresses. FIG. 30 shows the dependence of the relation (fourteenth relation) between pseudo remanence work $W_R^*$ and magnetic field amplitude $H_a$ on applied stresses. Stresses chosen for the graphs of FIG. 30 include, based on the results of a preliminary tensile test, the applied stress σ=0 (MPa) and the stress at the threshold of breaking point (σ=663 MPa), and intermediate values between the two extreme values, i.e., the applied stresses σ=550, 580 MPa. The results obtained at the points where the applied stresses σ=0, 550, 580 and 663 MPa are plotted by solid squares, open circles, open triangles, and solid triangles respectively in FIG. 30.

The minor hysteresis loops responsible for the production of graphs of FIG. 30 were obtained at the points where magnetic field amplitude $H_a$ was varied from 0 to 50 Oe. However, according to the evaluating method of the present invention, to obtain information sufficiently reliable to evaluate aged deterioration of an evaluating material, it is only necessary to vary magnetic field amplitude $H_a$ at most up to 20 Oe. The reason will be described later. In this example, the stepwise increment of magnetic field amplitude $H_a$ was chosen to be 1 Oe, but needless to say, a finer stepwise increment will bring more detailed information.

Figure 31:
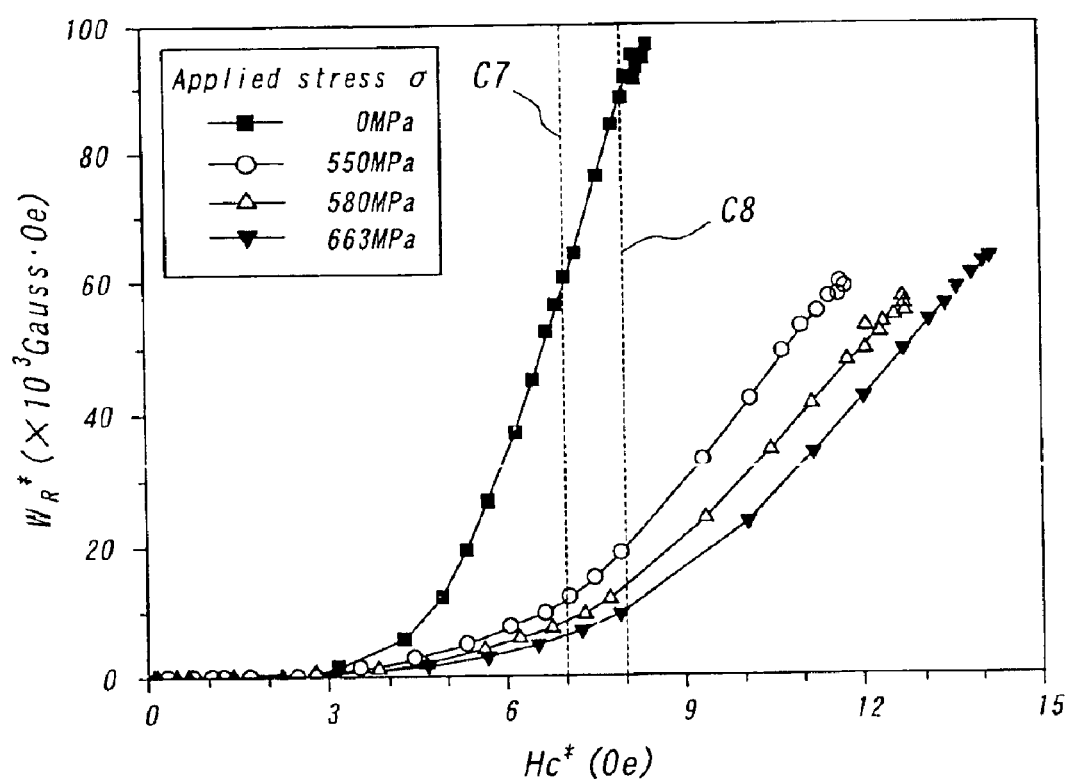
FIG. 31 is graphs exemplifying the dependence of the relation (fifteenth relation) between pseudo remanence work $W_R^*$ and the pseudo coercive force $Hc^*$ on stresses concomitantly applied, obtained from minor hysteresis loops of low-alloy steel A533B samples.

FIG. 31 illustrates the relation (fifteenth relation) between pseudo remanence work $W_R^*$ and the pseudo coercive force Hc* derived from the first relation as shown in FIG. 4 and the fourteenth relation as shown in FIG. 30, obtained from an evaluating material of a low-alloy steel A533B. In FIG. 31 as in FIG. 4, the results obtained at the points where the applied stresses σ=0, 550, 580 and 663 MPa are plotted by solid squares, open circles, open triangles, and solid triangles, respectively.

It is obvious from FIG. 31 that the relation between pseudo remanence work $W_R^*$ and pseudo coercive force Hc* changes separately with the increase of applied stresses σ. The curve plotted by solid triangles in FIG. 31 obtained under an applied stress σ=663 MPa is derived from an evaluating material just at the threshold of breakage.

Based on this observation, the Inventor demonstrated that deformation stresses σ (may be replaced with internal stresses) have an intimate correlation with the relation (fifteenth relation) between pseudo remanence work $W_R^*$ and pseudo coercive force Hc*. Moreover, because the relation between pseudo remanence work $W_R^*$ and pseudo coercive force Hc* varies depending on the type of evaluating materials, it is possible to identify a given evaluating material by evaluating the relation in question for that material.

As seen from the relation between the reciprocal $1/\chi_R^*$ of pseudo remanence susceptibility $\chi_R^*$ and pseudo remanence Br* shown in FIG. 25, it is possible to evaluate aged deterioration of an evaluating material by the following method without resorting to graphs extending over a full range.

It is possible to follow the aged deterioration of an evaluating material by comparing graphs in the range where the pseudo coercive force Hc* is comparatively low. Namely, as for FIG. 31, it is possible to evaluate aged deterioration of an evaluating material by taking pseudo remanence works $W_R^*$ corresponding to, for example, the pseudo coercive force Hc*=7 Oe (dashed line C7 in the figure) or 8 Oe (dashed line C8 in the figure), and by comparing them. Specifically, with regard to the curves obtained from data at the lower coercive force Hc* (dashed line C7 of FIG. 31), the pseudo remanence work $W_R^*$ changes markedly in the range where the applied stress σ is low, suggesting the material is very sensitive to plastic deformation at its initial stage of deformation. In contrast, with regard to the curve obtained from data at the higher coercive force Hc (dashed line C8 of FIG. 31), the pseudo remanence work $W_R^*$ changes considerably in the range where the applied stress σ is high, suggesting the material is sensitive to plastic deformation at the advanced stage of its deformation.

Figure 32:
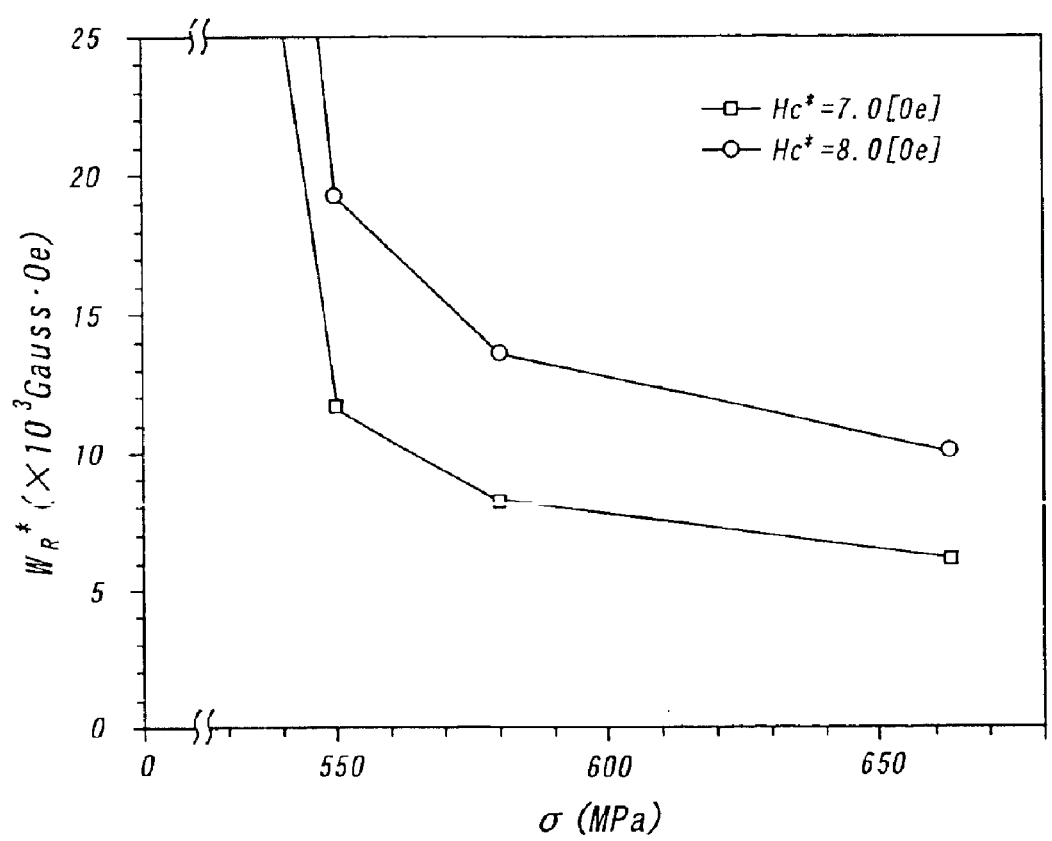
FIG. 32 is graphs showing the relation (sixteenth relation) between the pseudo remanence work $W_R^*$ and applied stresses $\sigma$ concomitantly applied at the pseudo coercive force $Hc^*=7$ and 8 Oe in a low-alloy steel A533B sample.

FIG. 32 gives graphs illustrating the relation (sixteenth relation) between the pseudo remanence work $W_R^*$ and stresses concomitantly applied at the point where the pseudo coercive forces Hc*=7 Oe (corresponding to dashed line C7 in FIG. 31) and 8 Oe (corresponding to dashed line C8 in FIG. 31). In FIG. 32, the results obtained at the point where the pseudo coercive forces Hc*=7 and 8 Oe are plotted by open squares and open circles, respectively.

According to the graphs shown in FIG. 32 for which data is extracted under a magnetic field whose magnetic field amplitude is rather low, it is possible to evaluate aged deterioration of an evaluating material and to appreciate the dislocation density, by performing a minor hysteresis loop measurement on the evaluating material and plotting pseudo remanence work $W_R^*$ corresponding to a pseudo coercive force Hc* with a predetermined value. Namely, it is possible to reliably evaluate aged deterioration of an evaluating material by resorting to data obtained from a minor hysteresis loop measurement where a maximum value of magnetic field amplitude having rather low magnetic field intensity is used.

The pseudo coercive force Hc* is the magnetic field intensity H obtained at the point where the pseudo susceptibility at pseudo coercive force $\chi_H^*$ becomes maximum as mentioned earlier. The pseudo remanence work $W_R^*$ represents the amount of energy converted into heat occurring in association with the irreversible movements of domain walls. Namely, the pseudo remanence work $W_R^*$ also represents a quantity exhibiting the extent of dislocations which hinder the movements of domain walls. Thus, it is possible to obtain an overview of the potential energy of domain wall movements by changing magnetic field amplitude $H_a$.

Thus, according to the evaluating method of the present invention, it is possible to determine the magnitude of forces imposed on domain walls and their distribution, by using the first relation (e.g., relation as shown in FIG. 4) of the relation between pseudo coercive force Hc* and magnetic field amplitude $H_a$, and fourteenth relation (e.g., relation as shown in FIG. 30) of the relation between pseudo remanence work $W_R^*$ and the magnetic field amplitude $H_a$. Therefore, it is possible to distinguish various lattice defects of the material responsible for its aged deterioration, and to separately quantify involved individual defects.

Thus, it is possible to specify individual lattice defects responsible for the aged deterioration of evaluating ferromagnetic materials used for constructing a reactor pressure vessel and to separately quantify the involvement of individual factors, by obtaining the pseudo coercive force Hc* and pseudo remanence work $W_R^*$ via the measurement step as well as the first and fourteenth relations and using those data for evaluating aged deterioration of the evaluating material. It is possible according to the evaluating method of the present invention to evaluate aged deterioration of evaluating materials more minutely, precisely and comprehensively than it is possible with conventional methods.

According to the evaluating method of the present invention, for example, as the graphs of FIG. 31 are obtained from the graphs of FIGS. 4 and 30, the evaluation information acquiring step may comprise obtaining the fifteenth relation of the relation between pseudo remanence work $W_R^*$ and pseudo coercive force Hc* from the first and fourteenth relations, and the evaluation step may comprise evaluating texture deterioration of an evaluating material as a result of aged deterioration using the fifteenth relation. According to this evaluating method, it is possible to evaluate aged deterioration of an evaluating material more precisely and easily than it is possible with conventional methods, based on the graphs described above.

Figure 33:
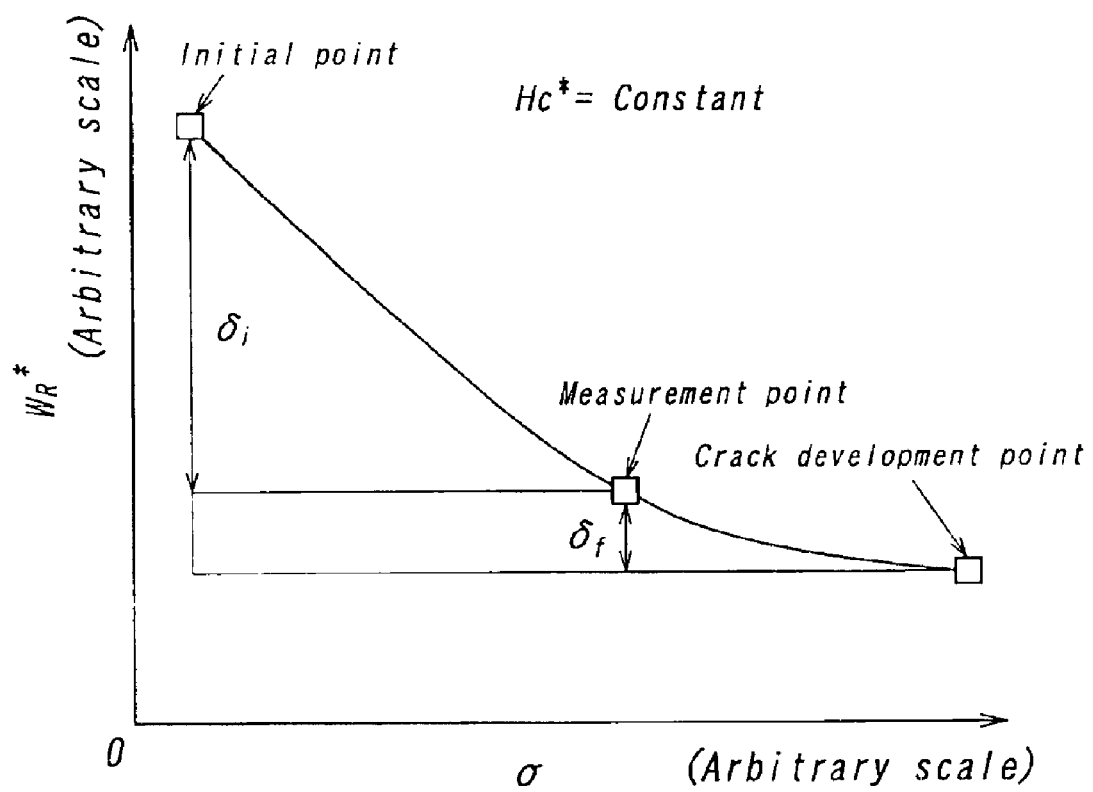
FIG. 33 is a graph for explaining the relation (sixteenth relation) between the applied stress $\sigma$ (MPa) and the pseudo remanence work $W_R^*$ at the point where the pseudo coercive force $Hc^*$ takes a predetermined value (pseudo coercive force $Hc^*$ is constant), and how to evaluate aged deterioration and expected life of the evaluating material based on the graph.

According to the evaluating method of the present invention, the evaluation information acquiring step may comprise obtaining the sixteenth relation of the relation between pseudo remanence work $W_R^*$ and the applied stress σ at a predetermined level of pseudo coercive force Hc* from the first and fourteenth relations or from the fifteenth relation, and the evaluation step may comprise evaluating texture deterioration of an evaluating material as a result of aged deterioration using the sixteenth relation. According to this method, as seen from the graph of FIG. 33 prepared from the graphs of FIG. 32, it is possible to quantitatively determine the applied stress σ at any desired point between the initial point and the crack initiation point. Thus, it is possible to predict aged deterioration ($\delta_i$ in FIG. 33) of an evaluating material and its expected life ($\delta_f$ in FIG. 33). Moreover, based on information provided via the evaluation information acquiring step, it is possible to appreciate change of the dislocation density.

Figure 34:
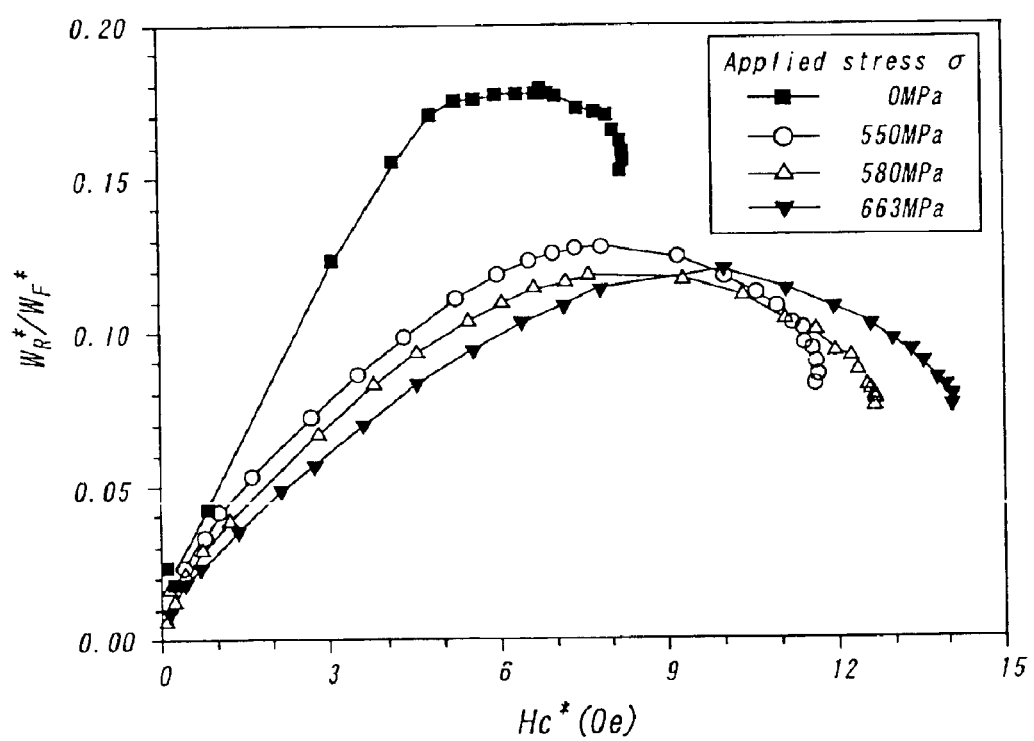
FIG. 34 is graphs for explaining the relation between the pseudo remanence work $W_R^*$ and the pseudo hysteresis loss $W_F^*$, obtained from minor hysteresis loops of low-alloy steel A533B samples.

Incidentally, it seems from the graphs of FIG. 34 that the pseudo remanence work $W_R^*$ may have a correlation with the pseudo hysteresis loss $W_F^*$ used in the foregoing method. However, obtainment of one does not always lead to obtainment of the other. Thus, for evaluating aged deterioration of evaluating materials, it is necessary to determine the pseudo remanence work $W_R^*$ and pseudo hysteresis loss $W_F^*$ independently of each other.

According to the evaluating method of the present invention, the evaluation information acquiring step may comprise obtaining the first relation of the relation between pseudo coercive force Hc* and magnetic field amplitude $H_a$, the pseudo coercive force Hc* being the magnetic field intensity H at the point where the magnetic flux density B is zero, and the seventeenth relation of the relation between the reciprocal $1/\chi_a^*$ of pseudo remanence susceptibility $\chi_a^*$ at magnetic field amplitude $H_a$ and magnetic field amplitude $H_a$, the pseudo remanence susceptibility at magnetic field amplitude $H_a$ being the gradient of a reference minor hysteresis loop at magnetic field amplitude $H_a$, and the measurement step may comprise measuring the pseudo coercive force Hc* being the magnetic field intensity H at magnetic field amplitude $H_a$, and the reciprocal $1/\chi_a^*$ of pseudo remanence susceptibility $\chi_a^*$ being the gradient of a subject minor hysteresis loop at magnetic field amplitude $H_a$.

As used herein, as described above with reference to the minor hysteresis loop of FIG. 10, out of the gradients of a reference minor hysteresis loop obtained at magnetic field amplitude $H_a$, the higher one is taken as the pseudo susceptibility at magnetic field amplitude $\chi_a^*$.

According to this version of the evaluating method of the present invention, similarly to the foregoing methods, stresses appropriately chosen according to the results of a previous tensile test are applied to an evaluating ferromagnetic material; the stresses are removed and the deformed evaluating material is exposed to a magnetic field whose maximum value of magnetic field amplitude is varied in a stepwise manner to obtain thereby minor hysteresis loops. From the minor hysteresis loops, as in the foregoing methods, the pseudo coercive force Hc*, pseudo remanence Br*, and pseudo susceptibility $\chi_a^*$ at magnetic field amplitude $H_a$ and its reciprocal are obtained, and the results are plotted as graphs, and from the graphs the first relation (as shown in FIG. 4) of the relation between pseudo coercive force Hc* and magnetic field amplitude $H_a$, and the seventeenth relation of the relation between the reciprocal $1/\chi_a^*$ of pseudo remanence susceptibility $\chi_a^*$ at magnetic field amplitude $H_a$ and magnetic field amplitude $H_a$ are obtained.

The present evaluating method will be described below with reference to minor hysteresis loop data obtained from a test sample made of low-alloy steel A533B.

Figure 35:
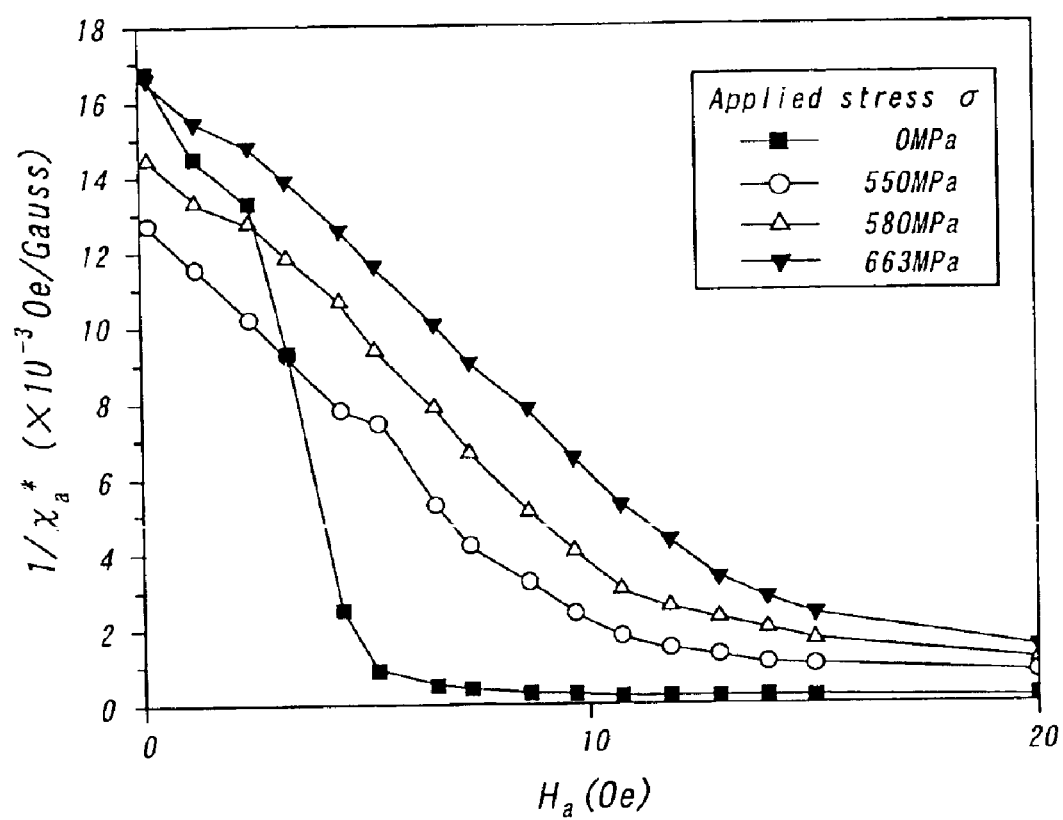
FIG. 35 is graphs exemplifying the dependence of the relation (seventeenth relation) between the reciprocal $1/\chi_a^*$ of susceptibility $\chi_a^*$ at magnetic field amplitude $H_a$ and magnetic field amplitude $H_a$ on stresses concomitantly applied, obtained from minor hysteresis loops of low-alloy steel A533B samples.

The first relation (as represented by the graphs of FIG. 4) of the relation between the pseudo coercive force Hc* and magnetic field amplitude $H_a$ and the seventeenth relation of the relation between the reciprocal $1/\chi_a^*$ of pseudo remanence susceptibility $\chi_a^*$ at magnetic field amplitude $H_a$ and magnetic field amplitude $H_a$ are obtained from minor hysteresis loop data. FIG. 4 shows the dependence of the relation between pseudo coercive force Hc* and magnetic field amplitude $H_a$ (first relation) on applied stresses. FIG. 35 shows the dependence of the relation (seventeenth relation) between the reciprocal $1/\chi_a^*$ of pseudo remanence susceptibility $\chi_a^*$ at magnetic field amplitude $H_a$ and magnetic field amplitude $H_a$ on applied stresses. Stresses chosen for the graphs of FIG. 35 include, based on the results of a preliminary tensile test similar with the graphs shown in FIG. 4, σ=0 (MPa) and stress at the threshold of breaking point (σ=663 MPa), and intermediate values between the two extreme values, i.e., the applied stresses σ=550, 580 MPa. The results obtained at the points where the applied stresses σ=0, 550, 580 and 663 MPa are plotted by solid squares, open circles, open triangles, and solid triangles respectively in FIG. 30.

The minor hysteresis loops responsible for the production of graphs of FIG. 35 and FIG. 4 were obtained at the points where magnetic field amplitude $H_a$ was varied from 0 to 40 Oe. However, according to the evaluating method of the present invention, to obtain information sufficiently reliable to evaluate aged deterioration of an evaluating material, it is only necessary to vary magnetic field amplitude $H_a$ at most up to 15 Oe. The reason will be described later. In this example, the stepwise increment of magnetic field amplitude $H_a$ was chosen to be 1 Oe, but needless to say, a finer stepwise increment will bring more detailed information.

According to the evaluating method of the present invention, the evaluation information acquiring step may comprise obtaining the eighteenth relation of the relation between the reciprocal $1/\chi_a^*$ of pseudo remanence susceptibility $\chi_a^*$ at magnetic field amplitude $H_a$ and pseudo coercive force Hc* from the first and seventeenth relations, and the evaluation step may comprise evaluating aged deterioration of an evaluating material using the eighteenth relation. According to this evaluating method, it is possible to evaluate aged deterioration of an evaluating material more minutely than it is possible with conventional methods as described later.

Figure 36:
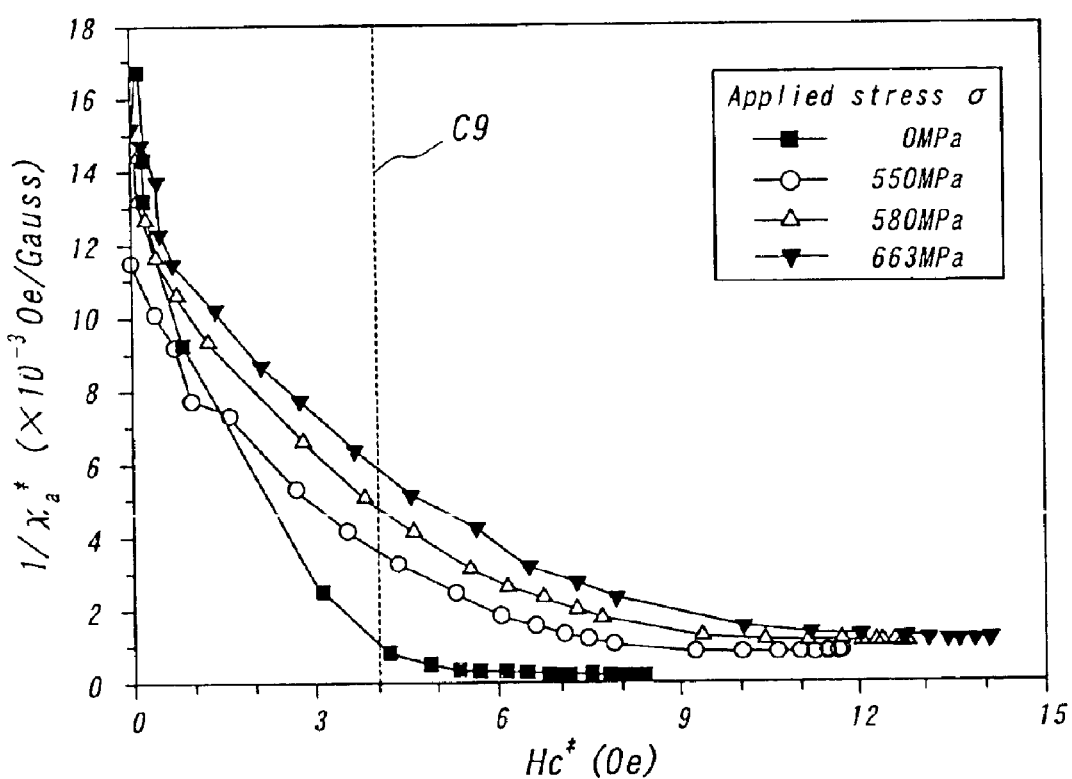
FIG. 36 is graphs exemplifying the relation (eighteenth relation) between the reciprocal $1/\chi_a^*$ of susceptibility $\chi_a^*$ at magnetic field amplitude $H_a$ and the pseudo coercive force $Hc^*$, obtained from minor hysteresis loops of low-alloy steel A533B samples.

FIG. 36 illustrates the relation (seventeenth relation) between the reciprocal $1/\chi_a^*$ of susceptibility $\chi_a^*$ at magnetic field amplitude $H_a$ and the pseudo coercive force Hc* derived from the relation (first relation) between pseudo coercive force Hc* and magnetic field amplitude $H_a$ as shown in FIG. 4, and relation (seventeenth relation) between the reciprocal $1/\chi_a^*$ of susceptibility $\chi_a^*$ at magnetic field amplitude $H_a$ and magnetic field amplitude $H_a$ as shown in FIG. 35, obtained from an evaluating material of low-alloy steel A533B. Stresses chosen for the graphs of FIG. 36 include, based on the results of a preliminary tensile test as in the graphs shown in FIGS. 4 and 35, σ=0, 550, 580, and 663 MPa. The results obtained at the points where σ=0, 550, 580 and 663 MPa are plotted by solid squares, open circles, open triangles, and solid triangles respectively. In FIG. 36, the reciprocal $1/\chi_a^*$ of susceptibility $\chi_a^*$ varies in the range of 0 to $18 \times 10^{-3}$ Oe/gauss.

As seen from FIG. 36, the relation between the reciprocal $1/\chi_a^*$ of susceptibility $\chi_a^*$ at magnetic field amplitude $H_a$ and pseudo coercive force Hc* changes with the increase of applied stresses (deformation stresses) σ. It is obvious from inspection of those graphs that deformation stresses (internal stresses) σ have an intimate correlation with the relation between the reciprocal $1/\chi_a^*$ of susceptibility $\chi_a^*$ at magnetic field amplitude $H_a$ and pseudo coercive force Hc*.

Although the conventional method for evaluating aged deterioration of an evaluating material depends on the measurement of the coercive force Hc of the material, the present method may use the relation between the reciprocal $1/\chi_a^*$ of susceptibility $\chi_a^*$ at magnetic field amplitude $H_a$ and pseudo coercive force Hc* for the same purpose, and the relation may exhibit a definite change even when the coercive force Hc does not show any notable change. In other words, although the conventional method evaluates aged deterioration of an evaluating material dependent on a single measurement of coercive force Hc, the present evaluating method achieves the same purpose dependent on the measurement covering a certain extent of the relation between the reciprocal $1/\chi_a^*$ of susceptibility $\chi_a^*$ at magnetic field amplitude $H_a$ and pseudo coercive force Hc* corresponding to the single coercive force measurement of the conventional method. Therefore, it is possible according to this method to evaluate aged deterioration of an evaluating material more minutely than it is possible with the conventional method.

It was further confirmed via the experiments performed by the Inventor that the relation between the reciprocal $1/\chi_a^*$ of susceptibility $\chi_a^*$ at magnetic field amplitude $H_a$ and pseudo coercive force Hc* changes in the same manner as above described with increase of the dislocation density, even when other ferromagnetic construction materials than those made of low-alloy steel A533B were used as test samples, and that the relation in question also changes depending on the grain size constituting the test steel material, other crystallizing substances, and added trace elements.

As is obvious from inspection of the relation between the reciprocal $1/\chi_a^*$ of susceptibility $\chi_a^*$ at magnetic field amplitude $H_a$ and pseudo coercive force Hc* shown in FIG. 36, it is possible to obtain information sufficiently reliable to evaluate aged deterioration of an evaluating material without tracing the relation over a full range as described below. For example, the minor hysteresis loops responsible for the production of graphs of FIG. 36 were obtained at the points where magnetic field amplitude $H_a$ was varied from 0 to 15 Oe. However, according to the evaluating method of the present invention, to obtain information sufficiently reliable to evaluate aged deterioration of an evaluating material, it is only necessary to vary magnetic field amplitude $H_a$ at most up to 6 Oe. This means according to this method, it is possible to evaluate aged deterioration of an evaluating material sufficiently reliably using data obtained from minor hysteresis loops which are obtained under a magnetic field whose maximum value of magnetic field amplitude $H_a$ remains rather low.

The aforementioned evaluating method consists of nondestructively evaluating the dislocation density in a test sample and following change of their distribution during aging leading to the initiation of cracks, and depends on the use of deformation stresses (strains). It has been known there is an intimate correlation between the applied stress and the dislocation density. Generally, at the initial stage of deformation, the dislocation density increases in proportion with the stress, while at the intermediate and later stage of aging the dislocation density increases in proportion with the square root of the stress. Therefore, it is possible to follow the change of the dislocation density via the relation between the reciprocal $1/\chi_a^*$ of susceptibility $\chi_a^*$ at magnetic field amplitude $H_a$ and pseudo coercive force Hc*. The applied stress may be replaced with the internal stress as described earlier. At the point where the dislocation density reaches a bearable maximum at a certain location, a crack will develop there which leads to the breakage of the sample. Therefore, it is possible to predict the time when cracks develop in the sample or the sample is broken, by resorting to the relation between the reciprocal $1/\chi_a^*$ of susceptibility $\chi_a^*$ at magnetic field amplitude $H_a$ and pseudo coercive force Hc*.

According to the evaluating method of the present invention, the evaluation information acquiring step may comprise obtaining the nineteenth relation of the relation between the reciprocal $1/\chi_a^*$ of susceptibility $\chi_a^*$ at magnetic field amplitude $H_a$ and applied stresses σ from the first and seventeenth relations, or the eighteenth relation, and the evaluation step may comprise evaluating aged deterioration of an evaluating material using the nineteenth relation. According to this evaluating method, it is possible to evaluate aged deterioration of an evaluating material more precisely and easily than it is possible with conventional methods as described later.

Figure 37:
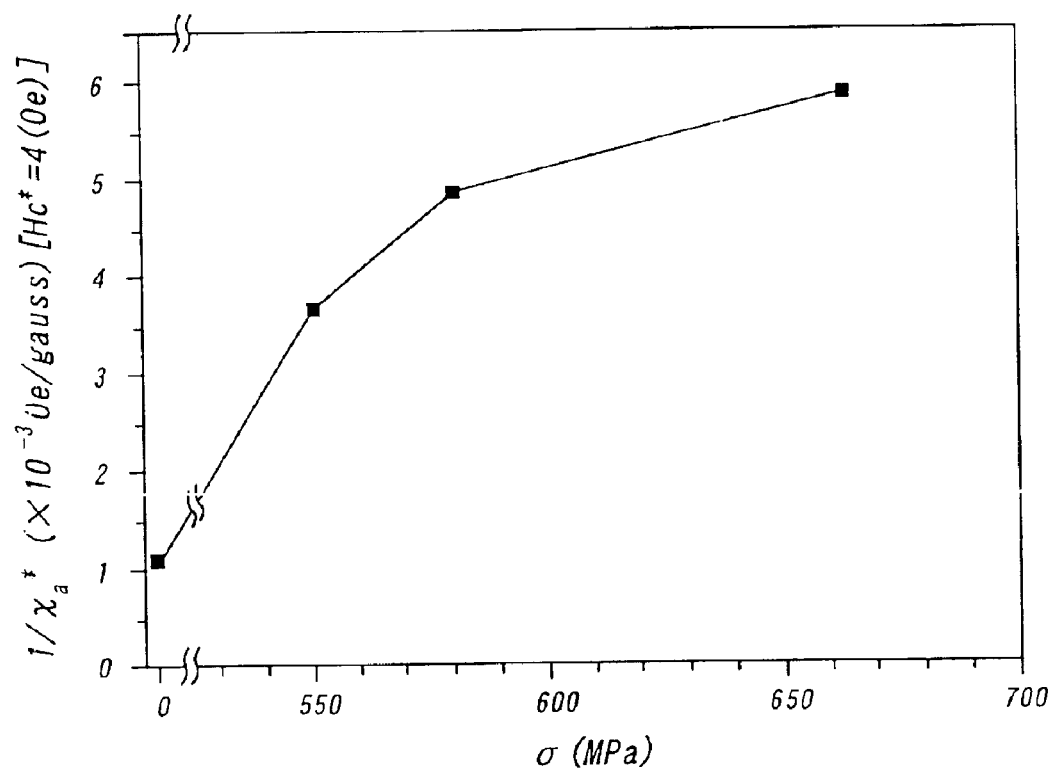
FIG. 37 is a graph showing the relation between the reciprocal $1/\chi_a^*$ of susceptibility $\chi_a^*$ at magnetic field amplitude $H_a$ and applied stresses $\sigma$ concomitantly applied at the pseudo coercive force $Hc^*=4$ Oe which is represented by the dashed line in FIG. 36.

FIG. 37 gives a graph illustrating the relation (nineteenth relation) between the reciprocal of pseudo remanence susceptibility at magnetic field amplitude $1/\chi_a^*$ and applied stresses σ at the point where the pseudo coercive force Hc*=4 Oe (corresponding to dashed line C9 in FIG. 36). According to the graph shown in FIG. 37, at the point where the state (χ=0 MPa) prior to plastic deformation is compared with the state (σ=663 MPa) at the threshold of breakage, the reciprocal $1/\chi_a^*$ of susceptibility $\chi_a^*$ at magnetic field amplitude $H_a$ increases from $1 \times 10^{-3}$ to $6 \times 10^{-3}$ Oe/gauss. In correspondence with this increase, the coercive force Hc or the maximum of pseudo coercive force Hc* shown in FIG. 36 (corresponds to coercive force obtained from a conventional hysteresis loop) increases from 8.5 to 14.2 Oe. Thus, in response to the same increase of applied stresses σ, the reciprocal $1/\chi_a^*$ of susceptibility $\chi_a^*$ at magnetic field amplitude $H_a$ employed by the present method increases by about six times while the coercive force employed in the conventional method increases by about 1.7 times. Thus, the present evaluating method is more sensitive than the conventional method due to the measurement of coercive force.

Figure 38:
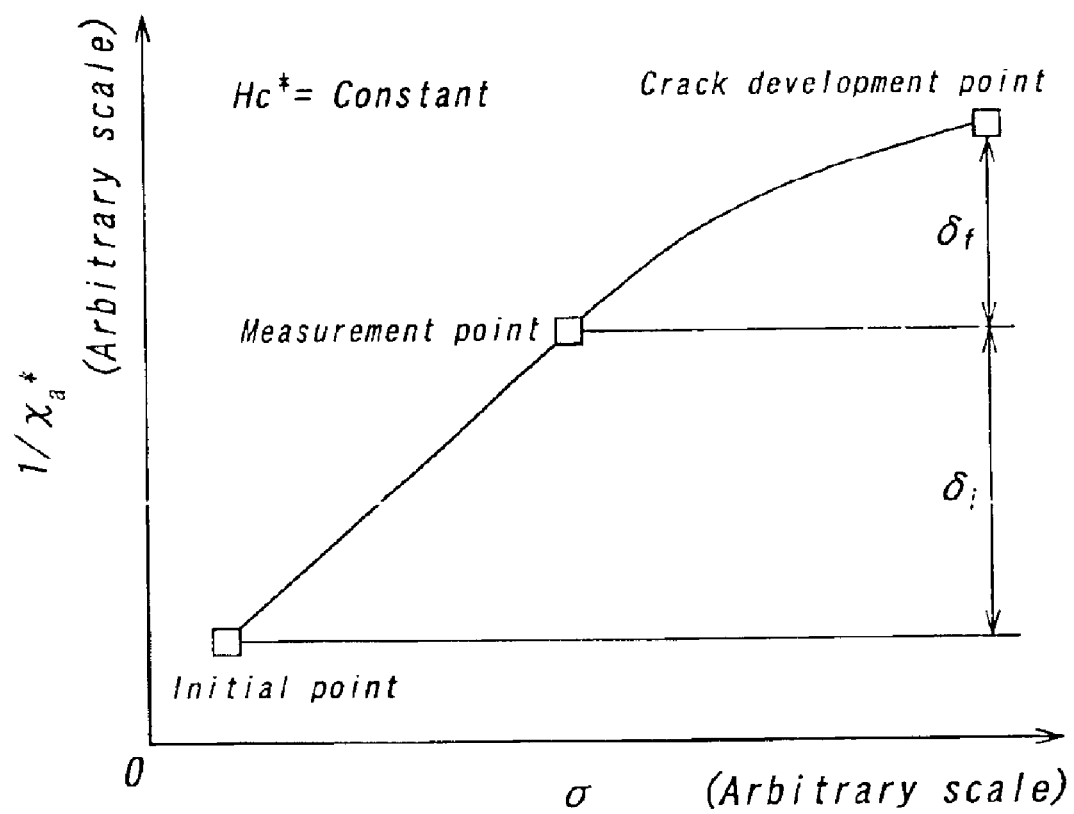
FIG. 38 is a conceptual graph showing the relation (nineteenth relation) between the reciprocal $1/\chi_a^*$ of susceptibility $\chi_a^*$ at magnetic field amplitude $H_a$ and applied stresses $\sigma$ at the point where the pseudo coercive force $Hc^*$ takes a predetermined value (pseudo coercive force is constant)

FIG. 38 is a conceptual graph (nineteenth relation) relating the reciprocal $1/\chi_a^*$ of susceptibility $\chi_a^*$ at magnetic field amplitude $H_a$ with applied stresses σ at the point where the coercive force Hc* takes a predetermined value. This conceptual graph is obtained by plotting the initial point and the crack initiation point on the graph (e.g., as shown in FIG. 37) relating the reciprocal $1/\chi_a^*$ of susceptibility $\chi_a^*$ at magnetic field amplitude $H_a$ with applied stresses σ. Thus, according to this graph illustrating the nineteenth relation, it is possible to easily predict aged deterioration ($\delta_i$ in FIG. 38) of an evaluating material and its expected life ($\delta_f$ in FIG. 38).

The pseudo coercive force Hc*, the reciprocal $1/\chi_H^*$ of pseudo susceptibility $\chi_H^*$ at pseudo coercive force Hc*, pseudo hysteresis loss $W_F^*$, the reciprocal $1/\chi_R^*$ of pseudo remanence susceptibility $\chi_R^*$, pseudo remanence work $W_R^*$, and the reciprocal $1/\chi_a^*$ of pseudo susceptibility $\chi_a^*$ at magnetic field amplitude $H_a$ which are used for evaluating aged deterioration of an evaluating material according to the invention are all very sensitive to the change of the dislocation density. Thus, the present method is superior in sensitivity and precision to the conventional method dependent on physical properties of an evaluating material such as coercive force. The present method can give more detailed information about aged deterioration of an evaluating material than the conventional method.

The physical quantities used in the present method for evaluating aged deterioration of an evaluating material can be derived from a minor hysteresis loop. Obtainment of a conventional hysteresis loop requires application of a magnetic field whose maximum value of magnetic field amplitude $H_a$ is sufficiently high to magnetize an evaluating material to a saturation level. In contrast, according to the present method, application of a magnetic field having a saturation magnetic field intensity is not needed, but magnetization by a magnetic field having a rather low magnetic field intensity can give sufficient data from which a minor hysteresis loop is prepared. In terms of preparing equipment for the test, the evaluating method of this invention dependent on the usage of a minor hysteresis loop is more advantageous than the conventional method using a conventional hysteresis loop, because the former will help the structure of equipment to be simplified.

To obtain a major hysteresis loop, it is necessary to apply a magnetic field to an evaluating material until the material is magnetized to complete saturation. Thus, the physical quantities derived from the major hysteresis loop are independent of the externally applied magnetic field. In contrast, according to the evaluating method of the present invention, a minor hysteresis loop is obtained which varies in association with change of the externally applied magnetic field. Thus, the physical quantities derived from the minor hysteresis loop change in association with change of the magnetic field. Therefore, it is necessary to precisely determine the physical quantities involved in the formation of the internal magnetism, paying due consideration to contributions by such factors as demagnetization and magnetic leak, when the physical quantities are derived from the minor hysteresis loop. However, the relation between the physical quantities used in the present method derive solely from the factors intrinsic to the evaluating material and are independent of the externally applied magnetic field. Therefore, as long as relations among those physical quantities are used for evaluating aged deterioration of an evaluating material as in the present method, it is not always necessary to precisely determine the applied magnetic field connected with the formation of the internal magnetism.

The pseudo hysteresis loss $W_F^*$, pseudo coercive force Hc*, the reciprocal of pseudo remanence susceptibility $1/\chi_R^*$, pseudo remanence Br*, and pseudo remanence work $W_R^*$ which are used for evaluating aged deterioration of an evaluating material according to the invention are all magnetic properties defining the magnetism intrinsic to an evaluating material, and the relations between above pseudo properties do not include any external factors. Accordingly, correlations between those magnetic properties will give information about the structural properties of an evaluating material including lattice defects, independent of external factors.

DESCRIPTION OF THE PREFERRED EMBODIMENTS

Figure 39:
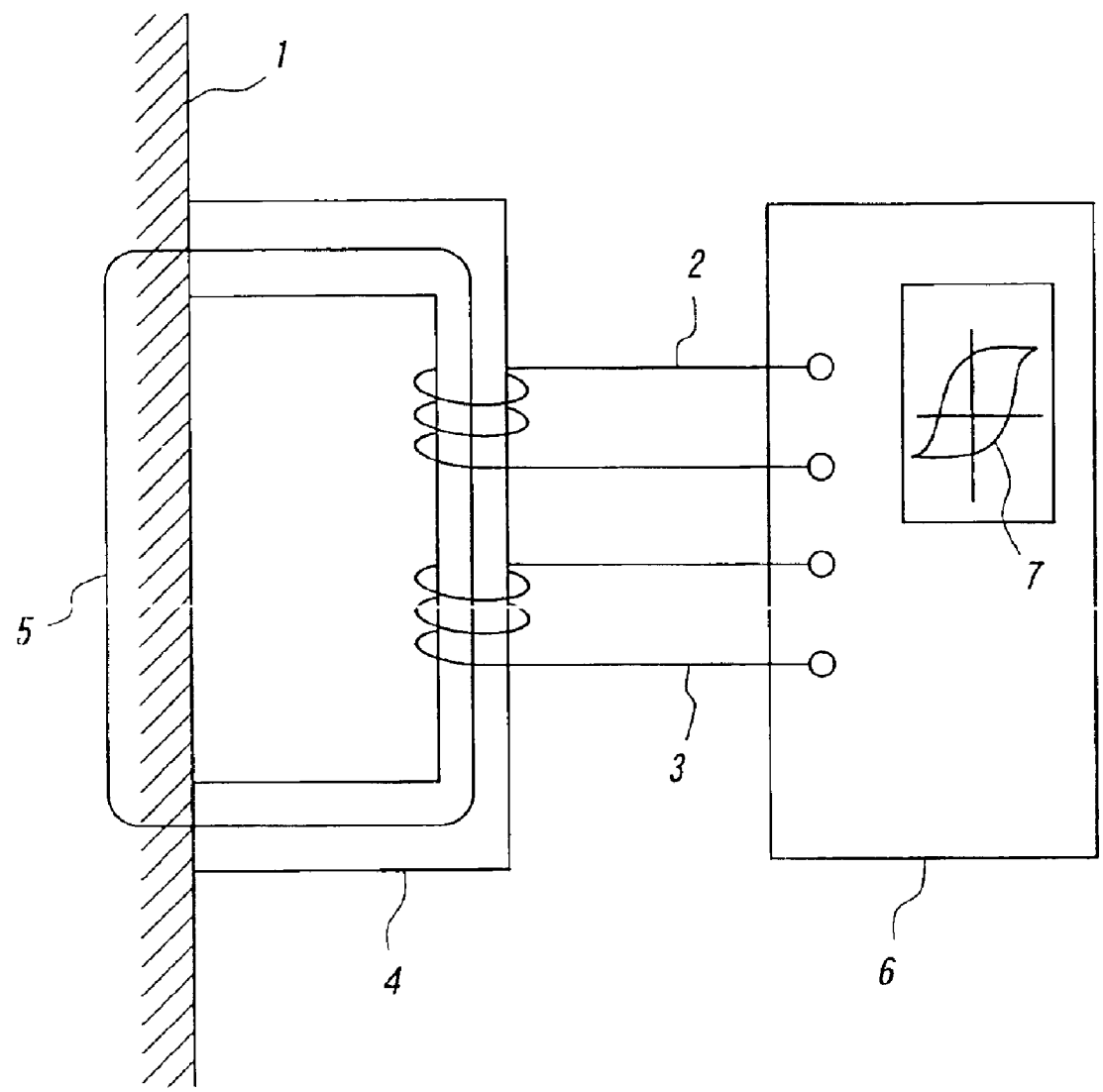
FIG. 39 is a schematic view showing the first embodiment of the method for nondestructively evaluating aged deterioration of ferromagnetic construction materials of the present invention.

The present invention will be described below by means of examples with reference to attached drawings. FIG. 39 illustrates a first embodiment of the method for nondestructively evaluating aged deterioration of ferromagnetic construction materials according to the present invention, wherein reference numeral 1 denotes a test structure comprised of a ferromagnetic construction material and exposed to external and/or internal forces; 2 a magnetizing coil; 3 a flux detecting coil; and 4 a magnetic yoke on which these coils 2 and 3 are wound. As shown in FIG. 39, the test structure 1 has a shape for which a direct winding of the coils 2 and 3 is impossible. Thus, the magnetic yoke 4 incorporating the magnetizing coil 2 and flux detecting coil 3 is tightly applied onto the test structure 1 to form a closed magnetic circuit 5. The magnetizing coil 2 and flux detecting coil 3 are connected to a magnetization measuring device 6. The magnetization measuring device 6 may be one which is commercially available in the market. A curve 7 represents the magnetization or hysteresis loop of the test structure 1 which is determined by, and displayed on the magnetization measuring device 6.

In the evaluating method according to the present invention, in order to perform a nondestructive aged deterioration test of the structure 1, the magnetization measuring device 6 supplies the magnetizing coil 2 with a magnetizing current. As a result, a voltage is induced in the flux detecting coil 3 and transmitted to the magnetization measuring device 6. The voltage is amplified and integrated by the measuring device 6 to determine a minor hysteresis loop 7 of the test structure 1. Then, it is possible to derive a pseudo coercive force Hc*, and pseudo susceptibility at the pseudo coercive force $\chi_H^*$ from the minor hysteresis loop (see FIG. 3). It is also possible to derive a pseudo coercive force Hc*, the reciprocal of pseudo susceptibility at the pseudo coercive force $1/\chi_H^*$, pseudo hysteresis loss $W_F^*$, the reciprocal of pseudo remanence susceptibility $1/\chi_R^*$, pseudo remanence work $W_R^*$, and the reciprocal of pseudo susceptibility at magnetic field amplitude $1/\chi_a^*$ from the minor hysteresis loop (see FIGS. 3 and 10).

The minor hysteresis loop 7 obtained from the test structure 1 exposed to a magnetic field may contain errors due to the three dimensional expanse of the flux pathways in the ferromagnetic material of the test structure 1 and also due to the demagnetizing factor. To obtain the hysteresis loop characteristic free from such errors, it is necessary to determine a correction factor. Such a correction factor might be obtained by a computer experiment based on a known static magnetic field analysis, or by a mock-up experiment simulating the measurement system.

In this embodiment, a magnetic field whose maximum value of magnetic field amplitude $H_a$ is lower than the saturation intensity or in the range of 0 to 60 Oe was applied to a test sample made of a steel material, and the same operation was repeated a number of times with magnetic field amplitude $H_a$ being varied in a stepwise manner, and a series of minor hysteresis loops were obtained. Magnetic field amplitude $H_a$ may be lower than the above value depending on a given test sample: For example, for a test sample made of pure iron, a magnetic field whose maximum value of magnetic field amplitude $H_a$ is at the most 15 Oe is sufficiently effective.

From the minor hysteresis loops 7 thus obtained, pseudo coercive forces Hc* and pseudo susceptibility at the pseudo coercive force $1/\chi_H^*$ can be obtained which are then used for evaluating aged deterioration of a test steel material.

To obtain the pseudo coercive force Hc* and pseudo susceptibility at the pseudo coercive force $\chi_H^*$ and its reciprocal $1/\chi_H^*$ of a test steel material in order to use those quantities for evaluating aged deterioration of the material, it is necessary to subject another material (reference material) similar to the evaluating material to a tensile test to determine a stress-strain relation. Appropriate applied stresses σ are chosen according to the stress-strain relation, and applied to a reference material while the material is magnetized. Magnetic field amplitude $H_a$ is varied between 0 and 60 Oe in a stepwise manner with a stepwise increment of 1 Oe, and a minor hysteresis loop is obtained each time magnetic field amplitude $H_a$ is altered. A series of minor hysteresis loops thus obtained are called reference minor hysteresis loops. From these minor hysteresis loops are derived pseudo coercive forces Hc* and pseudo susceptibilities at the pseudo coercive force $\chi_H^*$ and its reciprocals $1/\chi_H^*$, and the third relation of the relation between the reciprocal $1/\chi_H^*$ of pseudo susceptibility $\chi_H^*$ and pseudo coercive force Hc* is plotted as in FIG. 40.

Figure 40:
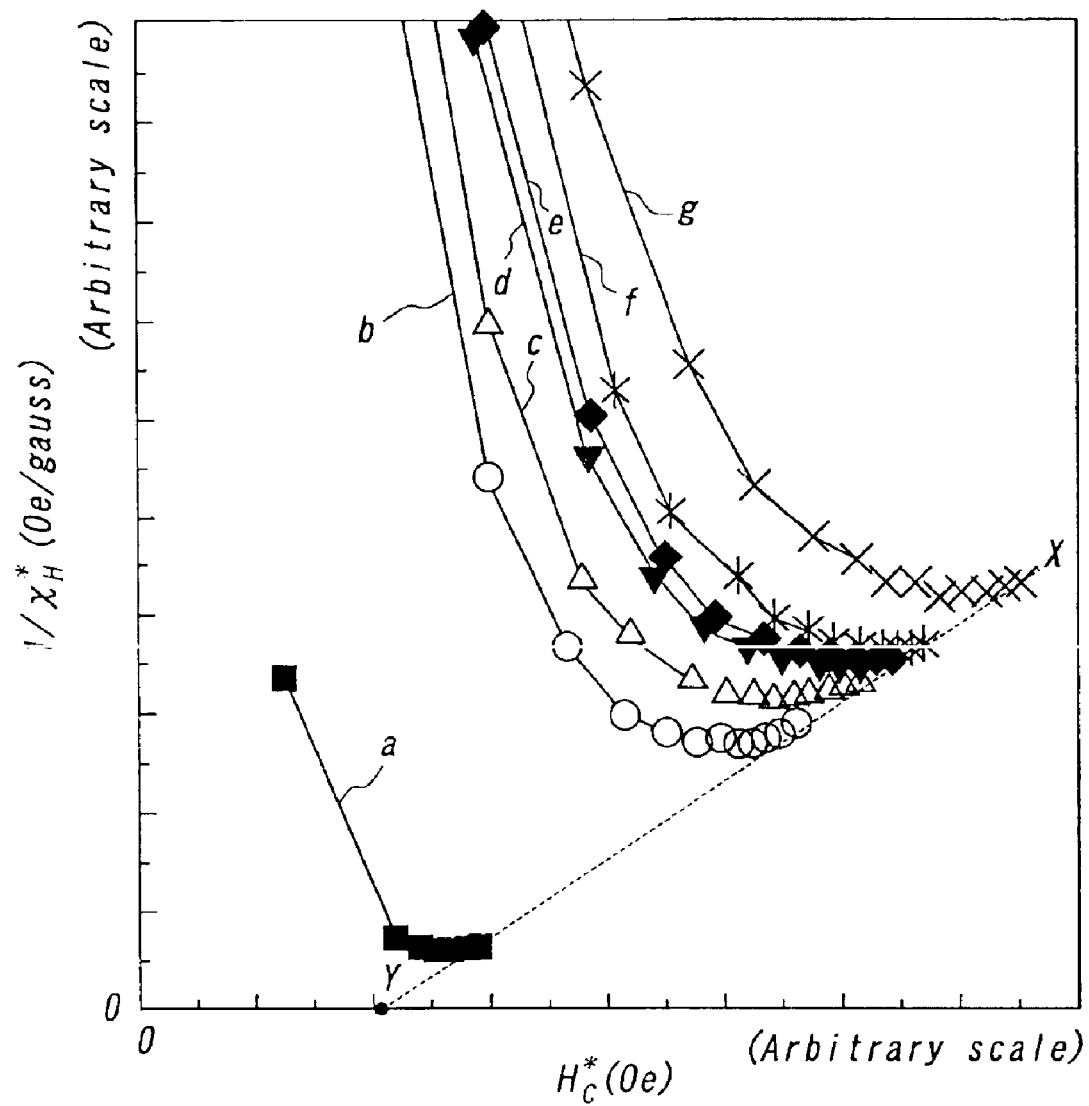
FIG. 40 is graphs exemplifying the relation (third relation) between the reciprocal $1/\chi_H^*$ of pseudo susceptibility $\chi_H^*$ at pseudo coercive force $Hc^*$ and the pseudo coercive force $Hc^*$ obtained via the first embodiment.

The evaluation step consists of obtaining the pseudo coercive force Hc* and the reciprocal of pseudo susceptibility at the pseudo coercive force $1/\chi_H^*$ via the measurement step (physical quantities actually measured), and comparing the actually measured physical quantities with the third relation (correlation between the two physical quantities), and evaluate aged deterioration of the evaluating material based on the comparison result. The curves of FIG. 40 represent the stress state of the evaluating material: with the progress of stress, curve a is followed by curve b which is then followed by curve c, and this process is repeated until curve g appears which represents the evaluating material at the threshold of breakage.

Figure 41:
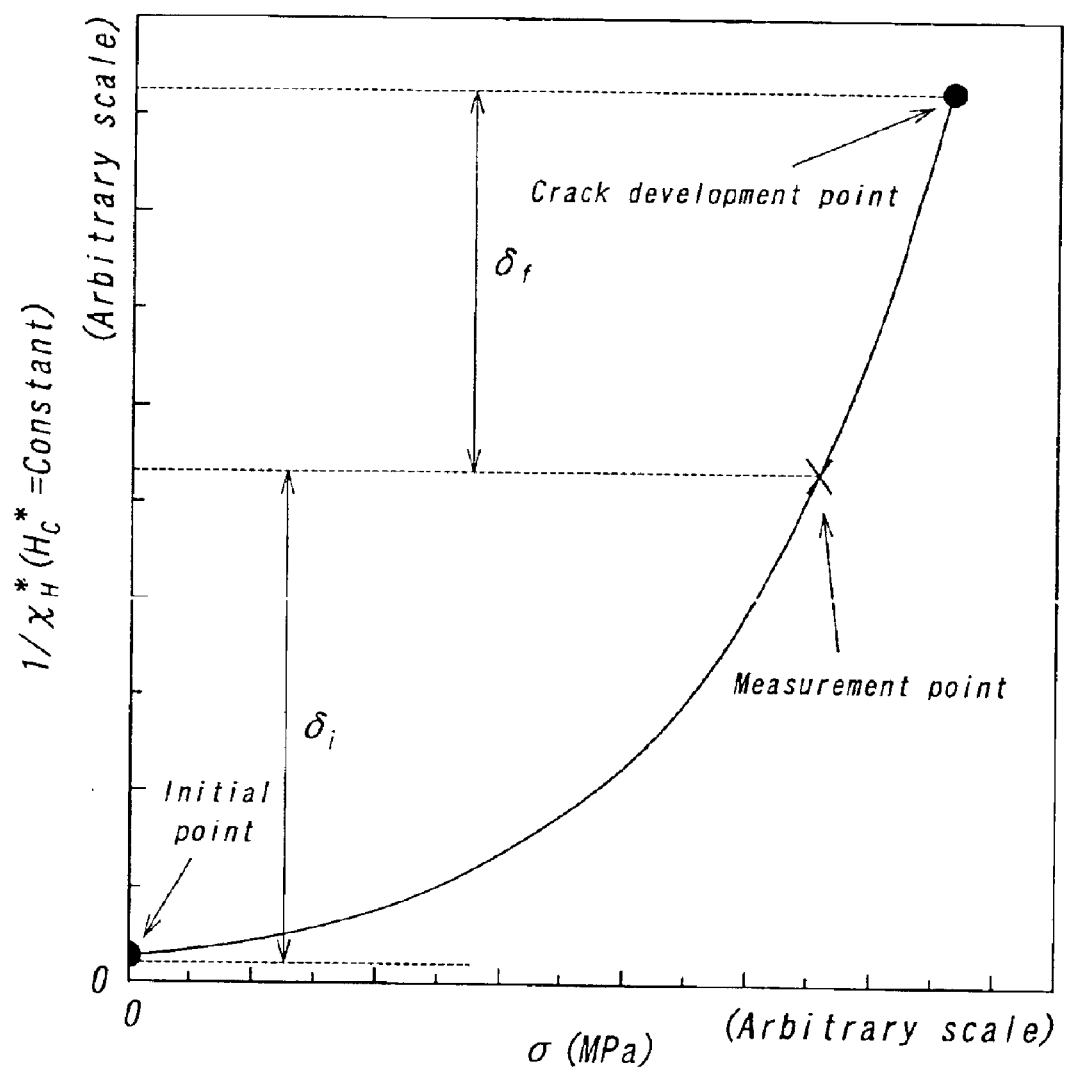
FIG. 41 is a conceptual graph showing the relation between the reciprocal $1/\chi_H^*$ of pseudo susceptibility $\chi_H^*$ at pseudo coercive force Hc* and applied stresses σ concomitantly applied at the point where the pseudo coercive force Hc* takes a predetermined value (pseudo coercive force is constant)

To compare the pseudo coercive force Hc* and the reciprocal of pseudo susceptibility at the pseudo coercive force $1/\chi_H{}^*$ obtained from a test steel material with the corresponding pseudo coercive force Hc* and the reciprocal of pseudo susceptibility at the pseudo coercive force $1/\chi_H{}^*$ obtained from a reference material at the aging start point, and the crack development point or breakage point on the latter's curve, applied stresses σ and the reciprocals of pseudo susceptibility $1/\chi_H{}^*$ at a certain pseudo coercive force Hc* (Hc*=8 Oe for the graph of FIG. 9) are determined. The relations between two quantities are plotted on a graph as shown in FIG. 41. By this means it is possible to determine an effective internal stress developed in a test structure having undergone aged deterioration.

On the graph of FIG. 41, $\delta_i$, $\delta_f$, or the difference between the aging start point (initial state) and crack initiation point is determined. In terms of the graph of FIG. 41, $\delta_i$ indicates the change of the reciprocal of pseudo susceptibility at the pseudo coercive force $1/\chi_H{}^*$ from the initial state to the measurement point, while $\delta_f$ indicates the change of the reciprocal of pseudo susceptibility at the pseudo coercive force $1/\chi_H{}^*$ will undergo before the material develops cracks. Thus, $\delta_i$ and $\delta_f$ are the parameters representing the aged deterioration of the evaluating material, and it is possible to evaluate aged deterioration of the evaluating material using those parameters: $\delta_i$ indicates aged deterioration the evaluating material has undergone and $\delta_f$ indicates expected life of the evaluating material or the period ahead which will elapse before the initiation of material cracks.

Evaluation of aged deterioration of an evaluating material may be achieved depending on a graph relating the pseudo coercive force Hc* with the reciprocal of pseudo susceptibility at the pseudo coercive force $1/\chi_H{}^*$. However, at the point where a certain pseudo coercive force Hc* is determined, it will then determine a reciprocal of pseudo susceptibility at the pseudo coercive force $1/\chi_H{}^*$, and the relation between the two parameters may be sufficient for evaluating aged deterioration of an evaluating material. In such a case, it is possible to easily and quantitatively evaluate aged deterioration of an evaluating material.

Referring to FIG. 9, the reciprocal of pseudo susceptibility at the pseudo coercive force $1/\chi_H{}^*$ increases from 0.2 Oe/gauss before plastic deformation (σ=0 MPa) to 2.4 Oe/gauss at the threshold of breakage (σ=663 MPa) at Hc*=8 Oe. On the other hand, the coercive force Hc* increases from 8.5 to 14.2 Oe as shown in FIG. 7. From this, with the same increase of applied stresses, the increment observed in the coercive force Hc is 1.7 time while the corresponding increment observed in the reciprocal of pseudo susceptibility at the pseudo coercive force $1/\chi_H{}^*$ is 12 times. This comparison demonstrates that the present method is more sensitive than the conventional method dependent on the measurement of coercive force. Therefore, according to the present evaluating method it is possible to evaluate aged deterioration of an evaluating material more sensitively.

According to the evaluating method of this invention for evaluating aged deterioration of ferromagnetic construction materials, it is possible to derive the pseudo coercive force Hc* and the reciprocal of pseudo susceptibility at the pseudo coercive force $1/\chi_H{}^*$ from a minor hysteresis loop obtained from an evaluating material, to relate the former with the latter (correlation between the two physical quantities), and to apply the result for precisely evaluating aged deterioration of the evaluating material. Moreover, the evaluating method can compare the state of the material occurring aged deterioration with a state prior to aged deterioration or a state at initiation of cracks. Therefore it is possible to evaluate nondestructively the extent of the aged deterioration of the evaluating material and its expected life. Thus, this evaluating method can be applied not only to polycrystalline ferromagnetic construction materials but also to various low-alloy steels including the materials used for the construction of a reactor pressure vessel. According to this evaluating method, it is possible to precisely determine aged deterioration of ferromagnetic materials and to precisely predict expected life of the material by appreciating the dislocation density and their distribution which will result in the breakage of the material. Moreover, the evaluating method of the invention can be achieved by a simple test device incorporating a magnetizing yoke and magnetizing power source.

Physical quantities obtained by the nondestructive aged deterioration evaluating method of the first embodiment and correlations among them, and physical quantities obtained via the measurement step will be described below. According to first to fourth variations, it is possible to convert some physical quantities and relations among them into other physical quantities and relations.

The first variation involving some physical quantities and relations among them, and physical quantities obtained via the measurement step concerns with two relations, that is, the first relation of the relation between the pseudo coercive force Hc* and magnetic field amplitude $H_a$, the fifth relation of the relation between the pseudo hysteresis loss $W_F{}^*$ and magnetic field amplitude $H_a$ the pseudo hysteresis loss $W_F{}^*$ being defined as an area enclosed by a reference minor hysteresis loop, and with a physical quantity obtained via the measurement step, that is, the pseudo hysteresis loss $W_F{}^*$ which is defined as an area enclosed by a subject minor hysteresis loop.

According to the first variant, it is possible to determine the pseudo coercive force Hc* and pseudo hysteresis loss $W_F{}^*$ of a test steel material from the minor hysteresis loop (subject minor hysteresis loop) obtained via the measurement step (see FIG. 10).

To evaluate aged deterioration of a test steel material based on the pseudo coercive force Hc* and pseudo hysteresis loss $W_F{}^*$, pseudo hysteresis losses $W_F{}^*$ at a certain pseudo coercive force Hc* and applied stresses σ are derived from reference minor hysteresis loops obtained in advance in the above example 1, the relation (seventh relation) between the two quantities are plotted on graphs as in FIG. 16. The seventh relation can also be derived from the relation between pseudo coercive force Hc* and magnetic field amplitude $H_a$ (first relation) as shown in FIG. 4, or from the relation between pseudo hysteresis loss $W_F{}^*$ and magnetic field amplitude $H_a$ (fifth relation) as shown in FIGS. 11 and 13, or from the relation between hysteresis loss $W_F{}^*$ and pseudo coercive force Hc* (sixth relation) as shown in FIGS. 14 and 15.

To compare the pseudo hysteresis loss $W_F{}^*$ obtained at the measurement step from a minor hysteresis loop of an evaluating material with the fifth relation at the evaluation step, the pseudo hysteresis loss $W_F{}^*$ actually measured at the measurement step is put as a measurement on the graph of FIG. 17. Through this operation, it is possible to determine an effective internal stress σ (deformation stress) developed within the test ferromagnetic structure 1 which has undergone aging, and thus to quantitatively evaluate aging of the test ferromagnetic structure 1.

According to the first variant, the evaluation step depends on the seventh relation. However, the seventh relation may be substituted for the first or fifth relation, or for the sixth relation derived from the first and fifth relations. Namely, the sixth relation may be applied to the relation between pseudo coercive force Hc* and pseudo hysteresis loss $W_F^*$ actually determined at the measurement step, to thereby evaluate the texture deterioration of the test ferromagnetic structure 1 occurring as a result of aged deterioration.

A second variant involves some physical quantities and relations among them, and physical quantities obtained via the measurement step. The relations in question include three relations, that is, the first relation of the relation between pseudo coercive force Hc* and magnetic field amplitude $H_a$, the eighth relation of the relation between pseudo remanence Br* (see FIG. 18) and magnetic field amplitude $H_a$, and the ninth relation of the relation between the reciprocal of differential susceptibility at pseudo remanence susceptibility $1/\chi_R^*$ and magnetic field amplitude $H_a$, the pseudo remanence susceptibility $\chi_R^*$ being the gradient of a reference minor hysteresis loop at the pseudo remanence Br*. The physical quantity in question includes pseudo coercive force Hc*, pseudo remanence Br*, and the reciprocal of pseudo remanence susceptibility $1/\chi_R^*$, the pseudo remanence susceptibility $\chi_R^*$ being the gradient of a subject minor hysteresis loop at the pseudo remanence Br*.

According to the second variant, it is possible to determine the pseudo coercive force Hc* and pseudo remanence Br* (see FIG. 18) and the reciprocal $1/\chi_R^*$ of pseudo remanence susceptibility $\chi_R^*$ of a test steel material from the minor hysteresis loop (subject minor hysteresis loop) obtained in the first embodiment via the measurement step.

To evaluate aged deterioration of a test steel material based on physical quantities determined via the measurement step of this variant, the relation between pseudo coercive force Hc* and magnetic field amplitude $H_a$ as shown in FIG. 4 (first relation), relation between pseudo remanence Br* and magnetic field amplitude $H_a$ as shown in FIGS. 12 and 21 (eighth relation), the and relation between the reciprocal of pseudo remanence susceptibility $1/\chi_R^*$ (see FIG. 18) and magnetic field amplitude (ninth relation) are plotted on graphs.

The evaluation step may consist of quantitatively evaluating aged deterioration of a test ferromagnetic structure 1 using the pseudo coercive force Hc*, pseudo remanence Br* and the reciprocal of pseudo remanence susceptibility $1/\chi_R^*$ derived from subject minor hysteresis loops in accordance with the first relation and the eighth and the ninth relations. If the evaluating material is made of low-alloy steel A533B, graphs of FIG. 4 and of FIGS. 19 and 20 are compared which enable aged deterioration of the evaluating material to be quantitatively determined. On the other hand, if the evaluating material is made of polycrystalline pure iron, graphs of FIG. 12 and of FIGS. 21 and 22 are compared which enable aged deterioration of the test ferromagnetic structure 1 to be quantitatively determined.

According to the second variant, the evaluation step depends on the first, eighth and ninth relations. However, those relations may be substituted for the relation between pseudo remanence Br* and pseudo coercive force Hc* (tenth relation) as shown in FIGS. 23 and 24, derived from the first and eighth relations. Namely, the tenth relation may be applied to the relation between pseudo remanence Br* and pseudo coercive force Hc* actually determined at the measurement step, to thereby evaluate the texture deterioration of the test ferromagnetic structure 1 occurring as a result of aged deterioration.

It is further possible to evaluate aged deterioration of an evaluating material by evaluating the relation (eleventh relation) of pseudo coercive force Hc* with applied stress σ at a certain pseudo remanence Br* as shown in FIG. 27.

It is further possible to evaluate aged deterioration of an evaluating material by evaluating the relation (twelfth relation) of pseudo remanence Br* with the reciprocal of pseudo remanence susceptibility $1/\chi_R^*$ as shown in FIGS. 25 and 26. It is still further possible to evaluate aged deterioration of an evaluating material by evaluating the thirteenth relation of the relation between the reciprocal $1/\chi_R^*$ of pseudo remanence susceptibility $\chi_R^*$ at a certain pseudo remanence Br* and applied stress σ.

A third variant involves some physical quantities and relations among them, and physical quantities obtained via the measurement step. The relations in question include two relations, that is, the first relation of the relation between pseudo coercive force Hc* and magnetic field amplitude $H_a$, and the fourteenth relation of the relation between pseudo remanence work $W_R^*$ (see FIG. 10) and magnetic field amplitude $H_a$, the pseudo remanence work $W_R^*$ being a fraction of the area enclosed by a reference minor hysteresis loop. The physical quantity in question includes the pseudo coercive force Hc*, and pseudo remanence work $W_R^*$ or a fraction of the area enclosed by a subject minor hysteresis loop.

According to the third variant, it is possible to determine the pseudo coercive force Hc* and pseudo remanence work $W_R^*$ (see FIG. 10) of a test steel material from the minor hysteresis loop (subject minor hysteresis loop) obtained in the first embodiment via the measurement step.

To evaluate aged deterioration of a test steel material based on the pseudo coercive force Hc* and pseudo remanence work $W_R^*$ determined for the test steel material, the relation between pseudo coercive force Hc* and magnetic field amplitude $H_a$ as shown in FIG. 4 (first relation), and the relation between pseudo remanence work $W_R^*$ and magnetic field amplitude $H_a$ as shown in FIG. 30 (fourteenth relation) derived at the evaluation information acquiring step from reference minor hysteresis loops are plotted on graphs.

The evaluation step may consist of quantitatively evaluating aged deterioration of a test ferromagnetic structure 1 using the pseudo coercive force Hc* and pseudo remanence work $W_R^*$ derived from subject minor hysteresis loops in accordance with the first and fourteenth relations.

According to the third variant, the evaluation step depends on the first and fourteenth relations. However, those relations may be substituted for the fifteenth relation of the relation between pseudo remanence work $W_R^*$ and pseudo coercive force Hc* as shown in FIG. 31 derived from the first and fourteenth relations. Namely, the relation may be applied to the relation between pseudo remanence work $W_R^*$ and pseudo coercive force Hc* actually determined at the measurement step, to thereby evaluate the texture deterioration of the test ferromagnetic structure 1 occurring as a result of aged deterioration. Alternatively, the sixteenth relation or the relation (see FIG. 32 and FIG. 33) of pseudo remanence work $W_R^*$ at a certain pseudo coercive force Hc* with applied stress σ derived from the first and fourteenth relations or from the fifteenth relation may be employed for evaluating the texture deterioration of an evaluating material.

A fourth variant involves some physical quantities and relations among them, and physical quantities obtained via the measurement step. The relations in question include two relations, that is, the first relation of the relation between pseudo coercive force Hc* and magnetic field amplitude $H_a$, and the seventeenth relation of the relation between the reciprocal $1/\chi_a^*$ of pseudo susceptibility $\chi_a^*$ at magnetic field amplitude $H_a$ and magnetic field amplitude $H_a$, the pseudo susceptibility at magnetic field amplitude $\chi_a^*$ being the gradient of a reference minor hysteresis loop at magnetic field amplitude. The physical quantity in question includes the pseudo coercive force Hc* at magnetic field amplitude, and pseudo susceptibility at magnetic field amplitude $\chi_a^*$ or the gradient of a minor hysteresis loop at maximum value of magnetic field amplitude.

According to the fourth variant, it is possible to determine the pseudo coercive force Hc* and the reciprocal of pseudo susceptibility at magnetic field amplitude $1/\chi_a^*$ (see FIG. 18) of a test steel material from the minor hysteresis loop (subject minor hysteresis loop) obtained in the first embodiment via the measurement step.

To evaluate aged deterioration of a test steel material based on the pseudo coercive force Hc* and the reciprocal of pseudo susceptibility at magnetic field amplitude $1/\chi_a^*$ (see FIG. 18) determined for the test steel material, the relation between pseudo coercive force Hc* and magnetic field amplitude $H_a$ as shown in FIG. 4 (first relation), and the relation between magnetic field amplitude $H_a$ and the reciprocal $1/\chi_a^*$ of pseudo susceptibility $\chi_a^*$ at magnetic field amplitude $H_a$ as shown in FIG. 35 (seventeenth relation) derived at the evaluation information acquiring step from reference minor hysteresis loops are plotted on graphs.

The evaluation step may consist of quantitatively evaluating aged deterioration of a test ferromagnetic structure 1 using the pseudo coercive force Hc* and the reciprocal $1/\chi_a^*$ of pseudo susceptibility $\chi_a^*$ at magnetic field amplitude $H_a$ derived from subject minor hysteresis loops in accordance with the first and seventeenth relations.

According to the fourth variant, the evaluation step depends on the first and seventeenth relations. However, those relations may be substituted for the relation (eighteenth relation) between the reciprocal $1/\chi_a^*$ of pseudo susceptibility $\chi_a^*$ at magnetic field amplitude $H_a$ and pseudo coercive force Hc* as shown in FIG. 36 derived from the first and seventeen relations. Namely, from the values of pseudo coercive force Hc* and the reciprocal $1/\chi_a^*$ of pseudo susceptibility $\chi_a^*$ at magnetic field amplitude $H_a$ actually determined at the measurement step on the base of the relation (eighteenth relation) between pseudo coercive force Hc* and the reciprocal $1/\chi_a^*$ of pseudo susceptibility $\chi_a^*$ at magnetic field amplitude $H_a$, it is possible to evaluate the change of texture due to aged deterioration of the test ferromagnetic structure 1. Alternatively, the nineteenth relation of the relation between the reciprocal $1/\chi_a^*$ of pseudo susceptibility $\chi_a^*$ at magnetic field amplitude $H_a$ at a certain pseudo coercive force Hc* and applied stress σ as shown in FIGS. 37 and 38 and derived from the first and seventeenth relations or from the eighteenth relation may be employed for evaluating the texture deterioration of an evaluating material.

Figure 42:
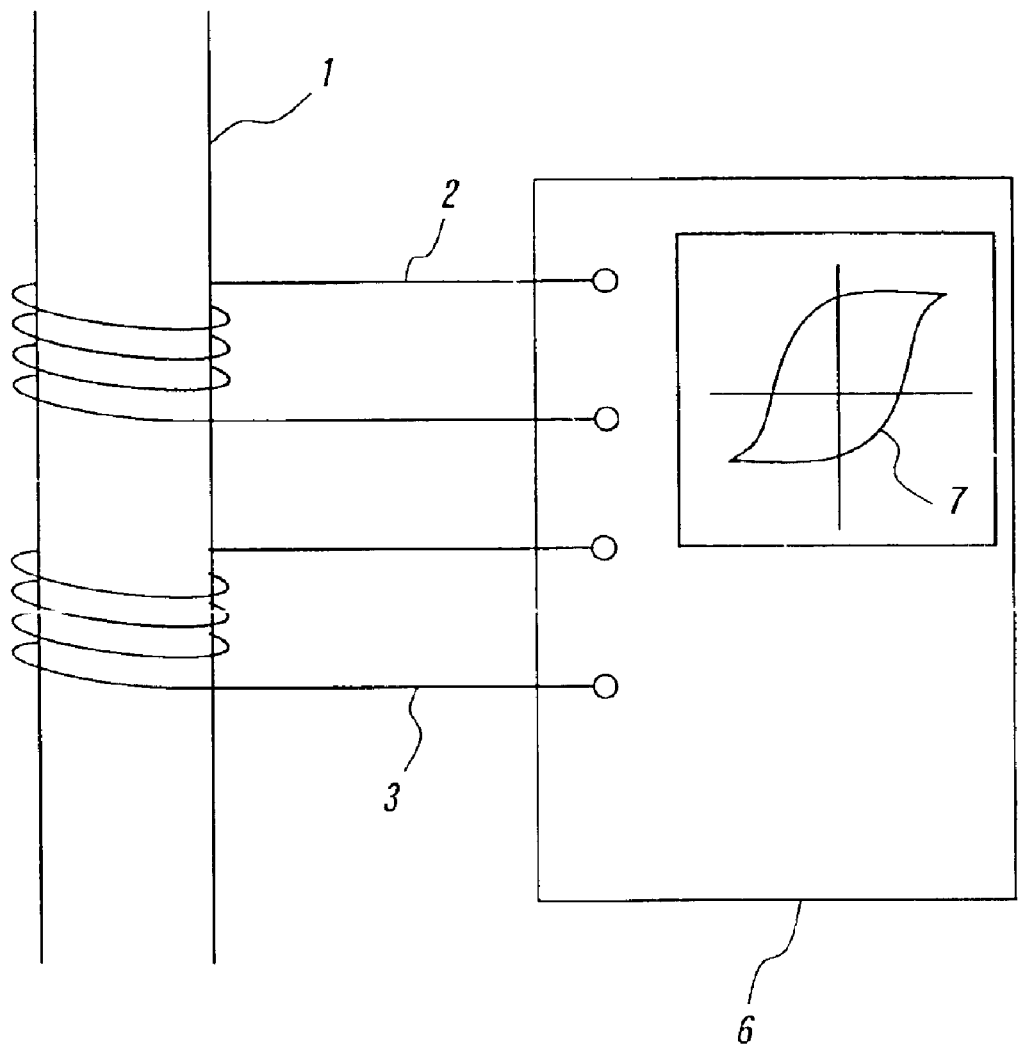
FIG. 42 is a schematic view showing the second embodiment of the method for nondestructively evaluating aged deterioration of ferromagnetic construction materials of the present invention.

FIG. 42 illustrates a second embodiment for executing the evaluating method of the invention for evaluating aged deterioration of ferromagnetic construction materials. In contrast to the above-described the first embodiment, the test structure 1 in the present example has a shape which allows a magnetizing coil 2 and a flux detecting coil 3 to be directly wound thereon. Thus, the magnetizing coil 2 and the flux detecting coil 3 are wound on the test structure 1 and connected to the minor hysteresis loop evaluating device 6 which may be composed of a commercially available products as in the first embodiment. The curve 7 represents the magnetization or the minor hysteresis loop of the test structure which is determined by, and displayed on the minor hysteresis loop evaluating device 6 as a result of the test performed.

In this embodiment, as in the foregoing first embodiment, at the measurement step the pseudo coercive force Hc* and the reciprocal of pseudo susceptibility at the pseudo coercive force $1/\chi_H^*$ are derived from a minor hysteresis loop actually determined. On the other hand, at the evaluation information acquiring step, the relation between pseudo coercive force Hc* and the reciprocal $1/\chi_H^*$ of pseudo susceptibility $\chi_H^*$ at the pseudo coercive force Hc* (third relation) are obtained for a reference material similar to a test ferromagnetic structure 1, and at the evaluation step, the relation between pseudo coercive force Hc* and the reciprocal $1/\chi_H^*$ of pseudo susceptibility $\chi_H^*$ at the pseudo coercive force Hc* actually obtained via the measurement step is compared with the corresponding relation obtained for the reference material, and aged deterioration of the evaluating material is evaluated based on the comparison result.

Needless to say, the relations among physical quantities obtained in the first to fourth variations and the physical quantities actually obtained via the measurement step in those variations can be similarly used in the second embodiment.

Thus, according to the evaluating method of the second embodiment, it is possible to sensitively determine aged deterioration of test ferro-magnetic structures in a nondestructive manner as in the first embodiment without requiring the use of a magnetizing yoke. Therefore, the test device may be simplified and made light.

In the description of the evaluating method of the invention for evaluating aged deterioration of ferromagnetic materials, the relations numbered in the above embodiments for identifying involved physical quantities are listed together with the involved physical quantities which are derived from minor hysteresis loops.

TABLE 2

| Relation No. | Physical quantities obtained from minor hysteresis loop | |
|---|---|---|
| 1st relation | Pseudo coercive force Hc* | Magnetic field amplitude $H_a$ |
| 2nd relation | Reciprocal of pseudo susceptibility at the pseudo coercive force $1/\chi_h^*$ | Magnetic field amplitude $H_a$ |
| 3rd relation | Reciprocal of pseudo susceptibility at the pseudo coercive force $1/\chi_h^*$ | Pseudo coercive force Hc* |
| 4th relation | Reciprocal of pseudo susceptibility at the pseudo coercive force $1/\chi_h^*$ | Applied stress σ(Hc*: predetermined value) |
| 5th relation | Pseudo hysteresis loss $W_F^*$ | Magnetic field amplitude $H_a$ |
| 6th relation | Pseudo hysteresis loss $W_F^*$ | Pseudo coercive force Hc* |
| 7th relation | Pseudo hysteresis loss $W_F^*$ | Applied stress σ(Hc*: predetermined value) |
| 8th relation | Pseudo remanence Br* | Magnetic field amplitude $H_a$ |
| 9th relation | Reciprocal of pseudo remanence susceptibility $1/\chi_R^*$ | Magnetic field amplitude $H_a$ |
| 10th relation | Pseudo remanence Br* | Pseudo coercive force Hc* |
| 11th relation | Pseudo coercive force Hc* | Applied stress σ(Hc*: predetermined value) |
| 12th relation | Reciprocal of pseudo remanence susceptibility $1/\chi_R^*$ | Pseudo remanence Br* |
| 13th relation | Reciprocal of pseudo remanence susceptibility $1/\chi_R^*$ | Applied stress σ (Hc*: predetermined value) |
| 14th relation | Pseudo remanence work $W_R^*$ | Magnetic field amplitude $H_a$ |

TABLE 2-continued

| Relation No. | Physical quantities obtained from minor hysteresis loop | |
| --- | --- | --- |
| 15th relation | Pseudo remanence work $W_R^*$ | Pseudo coercive force $Hc^*$ |
| 16th relation | Pseudo remanence work $W_R^*$ | Applied stress $\sigma(Hc^*$: predetermined value) |
| 17th relation | Reciprocal of pseudo susceptibility at magnetic field amplitude $1/\chi_a^*$ | Magnetic field amplitude $H_a$ |
| 18th relation | Reciprocal of pseudo susceptibility at magnetic field amplitude $1/\chi_a^*$ | Pseudo coercive force $Hc^*$ |
| 19th relation | Reciprocal of pseudo susceptibility at magnetic field amplitude $1/\chi_a^*$ | Applied stress $\sigma$ ($Hc^*$: predetermined value) |

The physical quantities used in the present aged deterioration test method for evaluating aged deterioration of a test ferromagnetic material and listed in Table 2, i.e., pseudo coercive force $Hc^*$, pseudo susceptibility at the pseudo coercive force $\chi_H^*$, pseudo hysteresis loss $W_F^*$, pseudo remanence $Br^*$, pseudo remanence susceptibility $\chi_R^*$, pseudo remanence work $W_R^*$, and pseudo susceptibility at magnetic field amplitude $\chi_a^*$ are all so sensitive to change of lattice defects such as dislocations that the method dependent on such physical quantities is better in sensitivity and precision than the conventional method dependent on coercive force derived from a conventional hysteresis loop. Accordingly, the present method, no matter which factor it depends on among the aforementioned ones, can give more detailed information about aged deterioration of an evaluating material than does the conventional method.

Those physical quantities can be derived from minor hysteresis loops. In the conventional method, it is necessary to apply a magnetic field until magnetization of an evaluating material reaches a saturation level. However according to the present method, application of a magnetic field having a saturation magnetic field intensity is not needed, but magnetization by a magnetic field having a rather low magnetic field intensity can give sufficient data from which a minor hysteresis loop is prepared. In terms of preparing equipment for the test, the evaluating method of this invention dependent on the usage of a minor hysteresis loop is more advantageous than the conventional method using a conventional hysteresis loop, because the former will help the structure of equipment to be simplified.

According to the evaluating method of the first and second embodiments, it is possible to distinguish different lattice defects within a test ferromagnetic material which have been thought, when the material is used for constructing a reactor pressure vessel, to cause the deterioration of the vessel, and to separately quantify those different defects, to thereby evaluating aged deterioration of the evaluating material more minutely, precisely and comprehensively than is possible with the conventional method.

To obtain a major hysteresis loop, it is necessary to apply a magnetic field to an evaluating material until the material is magnetized to complete saturation. Thus, the physical quantities derived from the major hysteresis loop are independent of the externally applied magnetic field. In contrast, according to the evaluating method of the invention, a minor hysteresis loop is obtained which varies in association with change of the externally applied magnetic field. Thus, the physical quantities derived from the minor hysteresis loop change in association with change of the magnetic field. Therefore, it is necessary to precisely determine the physical quantities involved in the formation of the internal magnetism, paying due consideration to contributions by such factors as demagnetization and magnetic leak, when the physical quantities (measurements) are derived from the minor hysteresis loop. However, the relations between physical quantities used in the present method derive solely from the factors intrinsic to the evaluating material and are independent of the externally applied magnetic field. Therefore, as long as relations among those physical quantities are used for evaluating aged deterioration of an evaluating material as in the present method, it is not always necessary to precisely determine the absolute value of magnetic field connected with the formation of the internal magnetism.

The invention has been described with reference to illustrated embodiments, but the invention is not limited only to those embodiments. The above embodiments involve measurements performed on a structure. However, the evaluating method of the invention can be applied not only to structures but also to materials used for the production of those structures. The evaluating methods invented by the Inventor, i.e., the one dependent on susceptibility coefficient c (Japanese Patent Publication No. 158182), one dependent on the ratio of coercive force against susceptibility (Japanese Patent Publication No. 3300810) and the present method dependent on pseudo coercive force $Hc^*$ and the reciprocal of pseudo susceptibility at the pseudo coercive force $1/\chi_H^*$ may be used alone or in combination. The combined method will allow one to evaluate aged deterioration of an evaluating material more precisely than is possible with the method used alone.

Physical quantities derived from minor hysteresis loops and their relations, and physical quantities actually measured at the measurement step to be used for the evaluation of aged deterioration of an evaluating material are not limited to those discussed with reference to the embodiments, but may include any relations chosen as appropriate for a given purpose. In the Specification, the invention has been described on the premise that the evaluating material is made of low-alloy steel A533B or polycrystalline pure iron. However, the present evaluating method can be applied to structures made of other ferromagnetic materials as effectively as to the materials discussed above.

What is claimed is:

1. A method for nondestructively and quantitatively evaluating aged deterioration of evaluating ferromagnetic construction materials, the steps of comprising:

an evaluation information acquiring step of obtaining a stress-strain relation in advance by a tensile test with respect to a test piece which is made of the same evaluating ferromagnetic construction material (evaluating material), evaluating a minor hysteresis loop (reference minor loop) of the test piece while applying an applied stress ($\sigma$) thereto, the applied stress ($\sigma$) being appropriately determined according to the stress-strain relation, and obtaining correlation between physical quantities for evaluating aged deterioration of the evaluating material;

a measurement step of obtaining a subject minor hysteresis loop (subject minor loop) by a tensile test with respect to the evaluating material and obtaining measured values of said physical quantities from the loop;

an evaluation step of evaluating aged deterioration of the evaluating material from said measured values of said physical quantities obtained in the measurement step, according to said correlation between said physical quantities obtained in the foregoing evaluation information acquiring step:

the minor hysteresis loops are obtained with respect to each the magnetic field amplitude ($H_a$) of the intensity (H) of the magnetic field from the relation between said intensity (H) and the magnetic flux density (B), the relation is obtained by measuring said magnetic flux density (B) of a measuring object with changing in stage a magnetic field applying to the measuring object.

2. A method as described in claim 1 for nondestructively evaluating aged deterioration of evaluating ferromagnetic construction materials wherein:

said correlation between physical quantities includes the first relation of the relation between the pseudo coercive force (Hc*) and magnetic field amplitude ($H_a$) applied to the measured object, the pseudo coercive force (Hc*) being the magnetic field intensity (H) at the point where the magnetic flux density (B) is zero, and the second relation of the relation between the reciprocal ($1/\chi_H^*$) of the pseudo susceptibility ($\chi_H^*$) being the gradient of a reference minor hysteresis loop at the point where the magnetic field intensity (H) is equal to the pseudo coercive force (Hc*) and magnetic field amplitude ($H_B$); and the physical quantities obtained via said measurement step comprise the pseudo coercive force (Hc*) being the magnetic field intensity (H) at the point where the magnetic flux density (B) is zero, and the reciprocal ($1/\chi_H^*$) of the pseudo susceptibility ($\chi_H^*$) being the gradient of said subject minor hysteresis loop at the point where the magnetic field intensity (H) is equal to the pseudo coercive force (Hc*).

3. A method as described in claim 2 for nondestructively evaluating aged deterioration of an evaluating ferromagnetic construction material wherein:

in said evaluation data obtaining step, the third relation of the relation between the reciprocal ($1/\chi_H^*$) of pseudo susceptibility ($\chi_H^*$) and the pseudo coercive force (Hc*), is obtained from said first relation and said second relation; and said evaluation step comprises evaluating aged deterioration of said evaluating ferromagnetic construction material from the third relation.

4. A method as described in claim 2 or 3 for nondestructively evaluating aged deterioration of a ferromagnetic construction material wherein:

the evaluation data obtaining step comprises obtaining the fourth relation of the relation between the reciprocal of susceptibility ($1/\chi_H^*$) and the applied stress (σ) at a predetermined pseudo coercive force (Hc*) from the first, second or third relation; and the evaluation step comprises evaluating aged deterioration of the evaluating material based on the fourth relation.

5. A method as described in claim 1 for nondestructively evaluating aged deterioration of an evaluating ferromagnetic construction material wherein:

said correlation between physical quantities includes the first relation of the relation between the pseudo coercive force (Hc*) and magnetic field amplitude ($H_a$) applied to the measured object, the pseudo coercive force (Hc*) being the magnetic field intensity (H) at the point where the magnetic flux density (B) is zero, and the fifth relation of the relation between the pseudo hysteresis loss ($W_F^*$) and magnetic field amplitude ($H_a$), the pseudo hysteresis loss ($W_F^*$) being defined as an area enclosed by a reference minor hysteresis loop; and the physical quantity data obtained via the measurement step includes the pseudo coercive force (Hc*) which is the magnetic field intensity (H) at the point where the magnetic flux density (B) is zero, and the pseudo hysteresis loss ($W_F^*$) which is an area enclosed by said subject minor hysteresis loop.

6. A method as described in claim 5 for nondestructively evaluating aged deterioration of an evaluating ferromagnetic construction material wherein:

the evaluation data obtaining step comprises obtaining the sixth relation of the relation between said pseudo hysteresis loss ($W_F^*$) and said pseudo coercive force (Hc*) from the first and fifth relations; and said evaluation step comprises evaluating aged deterioration of the evaluating material from the sixth relation.

7. A method as described in claim 5 for nondestructively evaluating aged deterioration of an evaluating ferromagnetic construction material wherein:

the evaluation data obtaining step comprises obtaining the seventh relation of the relation between the pseudo hysteresis loss ($W_F^*$) and an applied stress (σ) at a predetermined pseudo coercive force (Hc*) from the first and fifth relations or the sixth relation; and said evaluation step comprises evaluating aged deterioration of the evaluating material from the seventh relation.

8. A method as described in claim 1 for nondestructively evaluating aged deterioration of an evaluating ferromagnetic construction material wherein:

the correlation data between relevant physical quantities includes the first relation of the relation between the pseudo coercive force (Hc*) and magnetic field amplitude ($H_a$) applied to the evaluating material, the pseudo coercive force (Hc*) being the magnetic field intensity (H) at the point where the magnetic flux density (B) is zero, the eighth relation of the relation between the pseudo remanence (Br*) and magnetic field amplitude ($H_a$), the pseudo remanence (Br*) being the magnetic flux density (B) at the point where the magnetic field intensity (H) becomes zero, and the ninth relation of the relation between the reciprocal ($1/\chi_R^*$) of pseudo remanence susceptibility ($\chi_R^*$) and magnetic field amplitude ($H_a$), the pseudo remanence susceptibility ($\chi_R^*$) being the gradient of a reference minor hysteresis loop at the point where the magnetic flux density (B) is equal to the pseudo remanence (Br*); and the physical quantity data obtained via the measurement step includes the pseudo coercive force (Hc*) or the magnetic field intensity (H) at the point where the magnetic flux density (B) is zero, the pseudo remanence (Br*) or the magnetic flux density (B) at the point where the magnetic field intensity (H) becomes zero, and the reciprocal of pseudo remanence susceptibility ($1/\chi_R^*$), the pseudo remanence susceptibility ($\chi_R^*$) being the gradient of a subject minor hysteresis loop at the point where the magnetic flux density (B) is equal to the pseudo remanence (Br*).

9. A method as described in claim 8 for nondestructively evaluating aged deterioration of an evaluating ferromagnetic construction material wherein:

the evaluation data obtaining step comprises obtaining the tenth relation of the relation between the pseudo remanence (Br*) and the pseudo coercive force (Hc*) from the first and eighth relations; and the evaluation step comprises evaluating aged deterioration of the evaluating material from the tenth relation.

10. A method as described in claim 9 for nondestructively evaluating aged deterioration of an evaluating ferromagnetic construction material wherein:

the evaluation data obtaining step comprises obtaining the eleventh relation of the relation between the pseudo coercive force (Hc*) at predetermined pseudo remanence (Br*) and an applied stress from the tenth relation; and the eleventh relation is used for evaluating aged deterioration of the evaluating material.

11. A method as described in any one of claims 7, 8, 9, or 10 for nondestructively evaluating aged deterioration of an evaluating ferromagnetic construction material wherein:

the evaluation data obtaining step comprises obtaining the twelfth relation of the relation between the pseudo remanence (Br*) and the reciprocal ($1/\chi_R^*$) of pseudo remanence susceptibility ($\chi_R^*$) from the eighth and ninth relations, the pseudo remanence (Br*) being the magnetic flux density (B) at the point where the magnetic field intensity (H) being zero, and the pseudo remanence susceptibility ($\chi_R^*$) being the gradient of a reference minor hysteresis loop at the point where the magnetic flux density (B) is equal to the pseudo remanence (Br*); and the evaluation step comprises evaluating aged deterioration of the evaluating material from the twelfth relation.

12. A method as described in claim 8 for nondestructively evaluating aged deterioration of a test ferromagnetic construction material wherein:

the evaluation information acquiring step comprises obtaining the thirteenth relation or the relation between the reciprocal of pseudo remanence susceptibility ($1/\chi_R^*$) at a predetermined pseudo remanence (Br*) with an applied stress (σ) from the eighth and ninth relations or the twelfth relation;

the evaluation step comprises evaluating aged deterioration of the evaluating material from the thirteenth relation.

13. A method as described in claim 1 for nondestructively evaluating aged deterioration of an evaluating ferromagnetic construction material wherein:

the correlation data between relevant physical quantities includes the first relation of the relation between the pseudo coercive force (Hc*) and magnetic field amplitude ($H_a$) applied to the evaluating material, the pseudo coercive force (Hc*) being the magnetic field intensity (H) at the point where the magnetic flux density (B) is zero, and the fourteenth relation of the relation between pseudo remanence work ($W_R^*$) and magnetic field amplitude ($H_a$), the pseudo remanence work ($W_R^*$) being defined as a fraction of an area enclosed by a reference minor hysteresis loop; and the physical quantity data obtained via the measurement step includes the pseudo coercive force (Hc*) and the magnetic field intensity (H) at the point where the magnetic flux density (B) is zero, and the pseudo remanence work ($W_R^*$) and a fraction of an area enclosed by a subject minor hysteresis loop.

14. A method as described in claim 13 for nondestructively evaluating aged deterioration of an evaluating ferromagnetic construction material wherein:

the evaluation data obtaining step comprises obtaining the fifth relation of the relation between the pseudo remanence work ($W_R^*$) and the pseudo coercive force (Hc*) from the first and fourteenth relations; and the evaluation step comprises evaluating aged deterioration of the evaluating material from the fifth relation.

15. A method as described in claim 13 or 14 for nondestructively evaluating aged deterioration of an evaluating ferromagnetic construction material wherein:

the evaluation step comprises obtaining the sixteenth relation of the relation between the pseudo remanence work ($W_R^*$) at a predetermined pseudo coercive force (Hc*) and an applied stress (σ) from the first and fourteenth relations or the fifteenth relation; and the evaluation step comprises evaluating aged deterioration of the evaluating material from the sixteenth relation.

16. A method as described in claim 1 for nondestructively evaluating aged deterioration of an evaluating ferromagnetic construction material wherein:

the correlation data between relevant physical quantities includes the first relation of the relation between the pseudo coercive force (Hc*) and magnetic field amplitude ($H_a$) applied to the material, the pseudo coercive force being the magnetic field intensity (H) at the point where the magnetic flux density (B) is zero, and the seventeenth relation of the relation between the reciprocal ($1/\chi_a^*$) of pseudo susceptibility ($\chi_a^*$) at magnetic field amplitude ($H_a$) and magnetic field amplitude ($H_a$), the pseudo susceptibility at magnetic field amplitude ($\chi_a^*$) being the gradient of a reference minor hysteresis loop at magnetic field amplitude ($H_a$); and the physical quantity data obtained via the measurement step includes the pseudo coercive force (Hc*) and the magnetic field intensity (H) at the point where the magnetic flux density (B) is zero, and the reciprocal of pseudo susceptibility at magnetic field amplitude ($1/\chi_a^*$), the pseudo susceptibility ($\chi_a^*$) being the gradient of a subject minor hysteresis loop at magnetic field amplitude ($H_a$).

17. A method as described in claim 16 for nondestructively evaluating aged deterioration of an evaluating ferromagnetic construction material wherein:

the evaluation data obtaining step comprises obtaining the eighteenth relation of the relation between the reciprocal ($1/\chi_a^*$) of pseudo susceptibility ($\chi_a^*$) at magnetic field amplitude ($H_a$) and the pseudo coercive force (Hc*) from the first and seventeenth relations; and the evaluation step comprises evaluating aged deterioration of the evaluating material from the eighteenth relation.

18. A method as described in claim 16 or 17 for nondestructively evaluating aged deterioration of an evaluating ferromagnetic construction material wherein:

the evaluation data obtaining step comprises obtaining the nineteenth relation of the relation between the reciprocal ($1/\chi_a^*$) of pseudo susceptibility ($\chi_a^*$) at magnetic field amplitude ($H_a$) and an applied stress (σ) from the first and seventeenth relations or the eighteenth relation; and the evaluation step comprises evaluating aged deterioration of the evaluating material from the nineteenth relation.

19. A method as described in claim 6 for nondestructively evaluating aged deterioration of an evaluating ferromagnetic construction material wherein:

the evaluation data obtaining step comprises obtaining the seventh relation of the relation between the pseudo hysteresis loss ($W_F^*$) and an applied stress (σ) at a predetermined pseudo coercive force (Hc*) from the first and fifth relations or the sixth relation; and said evaluation step comprises evaluating aged deterioration of the evaluating material from the seventh relation.

20. A method as described in any one of claims 7, 8, 9, or 19 for nondestructively evaluating aged deterioration of an evaluating ferromagnetic construction material wherein:

the evaluation data obtaining step comprises obtaining the twelfth relation of the relation between the pseudo remanence (Br*) and the reciprocal ($1/\chi_R^*$) of pseudo remanence susceptibility ($\chi_R^*$) from the eighth and ninth relations, the pseudo remanence (Br*) being the magnetic flux density (B) at the point where the magnetic field intensity (H) being zero, and the pseudo remanence susceptibility ($\chi_R^*$) being the gradient of a reference minor hysteresis loop at the point where the magnetic flux density (B) is equal to the pseudo remanence (Br*); and the evaluation step comprises evaluating aged deterioration of the evaluating material from the twelfth relation, wherein:

the evaluation information acquiring step comprises obtaining the thirteenth relation or the relation between the reciprocal of pseudo remanence susceptibility ($1/\chi_R^*$) at a predetermined pseudo remanence (Br*) with an applied stress ($\sigma$) from the eighth and ninth relations or the twelfth relation;

the evaluation step comprises evaluating aged deterioration of the evaluating material from the thirteenth relation.

* * * * *